United States Patent
Shapira et al.

(10) Patent No.: US 12,268,377 B2
(45) Date of Patent: Apr. 8, 2025

(54) TWO-PRONGED APPROACH FOR BRONCHOSCOPY

(71) Applicant: W ENDOLUMINAL ROBOTICS LTD, Ariel (IL)

(72) Inventors: Eli Shapira, Kefar Sava (IL); Nir Shvalb, Bahan (IL); Oded Medina, Ariel (IL); Tsahi Itshak Grimberg, Kefar Sava (IL); Ron Kappel, Petah Tikva (IL)

(73) Assignee: W ENDOLUMINAL ROBOTICS LTD, Ariel (IL)

( * ) Notice: Subject to any disclaimer, the term of this patent is extended or adjusted under 35 U.S.C. 154(b) by 0 days.

(21) Appl. No.: 18/681,980

(22) PCT Filed: Aug. 11, 2022

(86) PCT No.: PCT/IB2022/057505
§ 371 (c)(1),
(2) Date: Feb. 7, 2024

(87) PCT Pub. No.: WO2023/017460
PCT Pub. Date: Feb. 16, 2023

(65) Prior Publication Data
US 2024/0366202 A1    Nov. 7, 2024

Related U.S. Application Data

(60) Provisional application No. 63/231,895, filed on Aug. 11, 2021.

(51) Int. Cl.
  *A61B 17/00* (2006.01)
  *A61B 17/3205* (2006.01)
  (Continued)

(52) U.S. Cl.
  CPC .... *A61B 17/00234* (2013.01); *A61B 17/3205* (2013.01); *A61B 18/00* (2013.01);
  (Continued)

(58) Field of Classification Search
  CPC ..... A61B 1/00087; A61B 1/018; A61B 1/267; A61B 1/2673; A61B 1/2676;
  (Continued)

(56) References Cited

U.S. PATENT DOCUMENTS 6,234,958 B1 *  5/2001  Snoke ................. A61B 1/303
                                                    600/114
6,800,056 B2  10/2004  Tartaglia et al.
  (Continued)

FOREIGN PATENT DOCUMENTS

EP    2754400 B1    3/2017
EP    2796083 B1    3/2017
  (Continued)

OTHER PUBLICATIONS

Yarmus et al. (2019) First-in-Human Use of a Hybrid Real-Time Ultrasound-Guided Fine-Needle Acquisition System for Peripheral Pulmonary Lesions: A Multicenter Pilot Study. Respiration. 2019;98(6):527-533. doi: 10. 1159/000504025. Epub Nov. 8, 2019. PMID: 31707384; PMCID: PMC6940022.
  (Continued)

*Primary Examiner* — Aaron B Fairchild
*Assistant Examiner* — Stephen Floyd London
(74) *Attorney, Agent, or Firm* — The Roy Gross Law Firm, LLC; Roy D. Gross

(57) ABSTRACT

Via a trachea (5) of the subject, an end of a first tube (120) is advanced along a first airway route (127) to an imaging site (20) within the lung (55). Independently of the first tube, an end of a second tube (130) is advanced along a second airway route (130) to a tool site (30) within the lung. While
  (Continued)

the first tube remains extended along the first route and the second tube remains extended along the second route, an imaging device (128), extended from the end of the first tube, is used to image a tool (138) extended from the end of the second tube, and a target (40) within the lung. The tool can be used to perform a procedure on the target, guided by the imaging of the target and the tool. Other embodiments are also described.

21 Claims, 25 Drawing Sheets

(51) Int. Cl.
*A61B 18/00* (2006.01)
*A61B 90/00* (2016.01)
(52) U.S. Cl.
CPC ............ *A61B 90/361* (2016.02); *A61B 90/37* (2016.02); *A61B 2017/003* (2013.01); *A61B 2017/0034* (2013.01); *A61B 2017/00809* (2013.01); *A61B 2018/00577* (2013.01); *A61B 2018/00982* (2013.01); *A61B 2090/373* (2016.02); *A61B 2090/3784* (2016.02)
(58) Field of Classification Search
CPC .......... A61B 17/00234; A61B 17/3205; A61B 17/3415; A61B 18/00; A61B 90/361; A61B 90/37; A61B 2017/003; A61B 2017/0034; A61B 2017/00809; A61B 2017/3445; A61B 2017/3447; A61B 2018/00577; A61B 2018/00982; A61B 2090/371; A61B 2090/373; A61B 2090/3784; A61M 25/0662; A61M 25/0068; A61M 2025/0188
See application file for complete search history.

(56) References Cited

U.S. PATENT DOCUMENTS

| | | | |
|---|---|---|---|
| 7,042,184 B2 | 5/2006 | Oleynikov et al. | |
| 8,002,697 B2 | 8/2011 | Moriyama | |
| 8,114,097 B2 | 2/2012 | Brock et al. | |
| 8,137,264 B2 | 3/2012 | Moriyama | |
| 8,226,546 B2 | 7/2012 | Belson | |
| 8,277,373 B2 | 10/2012 | Maahs et al. | |
| 8,409,234 B2 | 4/2013 | Stahler et al. | |
| 8,414,246 B2 | 4/2013 | Tobey | |
| 8,424,942 B2 | 4/2013 | Park et al. | |
| 8,800,838 B2 | 8/2014 | Shelton, IV | |
| 9,096,033 B2 | 8/2015 | Holop et al. | |
| 9,173,548 B2 | 11/2015 | Omori | |
| 9,221,179 B2 | 12/2015 | Hinman | |
| 9,370,868 B2 | 6/2016 | Danitz et al. | |
| 9,550,299 B2 | 1/2017 | Wolf et al. | |
| 9,687,621 B2 | 6/2017 | Hoftman et al. | |
| 9,763,741 B2 | 9/2017 | Alvarez et al. | |
| 9,962,228 B2 | 5/2018 | Schuh et al. | |
| 9,999,473 B2 | 6/2018 | Madhani et al. | |
| 10,076,235 B2 | 9/2018 | Choset et al. | |
| 10,405,940 B2 | 9/2019 | Romo | |
| 11,135,716 B2 | 10/2021 | Zarrouk | |
| 11,197,720 B2 | 12/2021 | Zarrouk et al. | |
| 2004/0186349 A1 | 9/2004 | Ewers et al. | |
| 2005/0272977 A1 | 12/2005 | Saadat et al. | |
| 2007/0270686 A1 | 11/2007 | Ritter et al. | |
| 2009/0318798 A1* | 12/2009 | Singh | A61B 1/012 604/544 |
| 2011/0137127 A1* | 6/2011 | Schwartz | A61B 1/05 600/188 |
| 2011/0315147 A1* | 12/2011 | Wood | A61M 16/0463 128/207.15 |
| 2013/0304084 A1 | 11/2013 | Beira et al. | |
| 2013/0324798 A1* | 12/2013 | Molnar | A61M 16/042 128/200.26 |
| 2014/0046176 A1 | 2/2014 | Ladtkow et al. | |
| 2014/0163327 A1 | 6/2014 | Swanstrom | |
| 2016/0100900 A1 | 4/2016 | Madhani et al. | |
| 2016/0374541 A1 | 12/2016 | Agrawal et al. | |
| 2017/0055967 A1 | 3/2017 | Raybin et al. | |
| 2017/0281296 A1 | 10/2017 | Cooper et al. | |
| 2018/0279852 A1* | 10/2018 | Rafii-Tari | G16H 40/63 |
| 2018/0338673 A1* | 11/2018 | Krimsky | A61B 34/20 |
| 2019/0133698 A1 | 5/2019 | Beira et al. | |
| 2019/0254649 A1* | 8/2019 | Walters | A61B 1/07 |
| 2020/0093554 A1 | 3/2020 | Schuh et al. | |
| 2020/0113427 A1* | 4/2020 | Molnar | A61M 16/0402 |
| 2020/0405348 A1 | 12/2020 | Kugler et al. | |
| 2021/0000457 A1 | 1/2021 | Raybin et al. | |
| 2021/0093290 A1* | 4/2021 | Finger | A61B 8/085 |
| 2022/0110514 A1* | 4/2022 | Molnar | A61B 1/00082 |

FOREIGN PATENT DOCUMENTS

| | | |
|---|---|---|
| EP | 2907467 B1 | 8/2018 |
| WO | 2012012740 A1 | 1/2012 |
| WO | 2014134031 A2 | 9/2014 |
| WO | 2019051274 A2 | 3/2019 |
| WO | 2020005854 A1 | 1/2020 |

OTHER PUBLICATIONS

PCT International Search Report for International Application No. PCT/IB2022/057505, mailed Jan. 5, 2023, 5pp.
PCT Written Opinion for International Application No. PCT/IB2022/057505, mailed Jan. 5, 2023, 10pp.
PCT International Preliminary Report on Patentability Chapter II for International Application No. PCT/IB2022/057505, completed Aug. 10, 2023, 5pp.
Annex to the International Preliminary Report on Patentability (Chapter II), dated Mar. 21, 2023, 15pp.

* cited by examiner

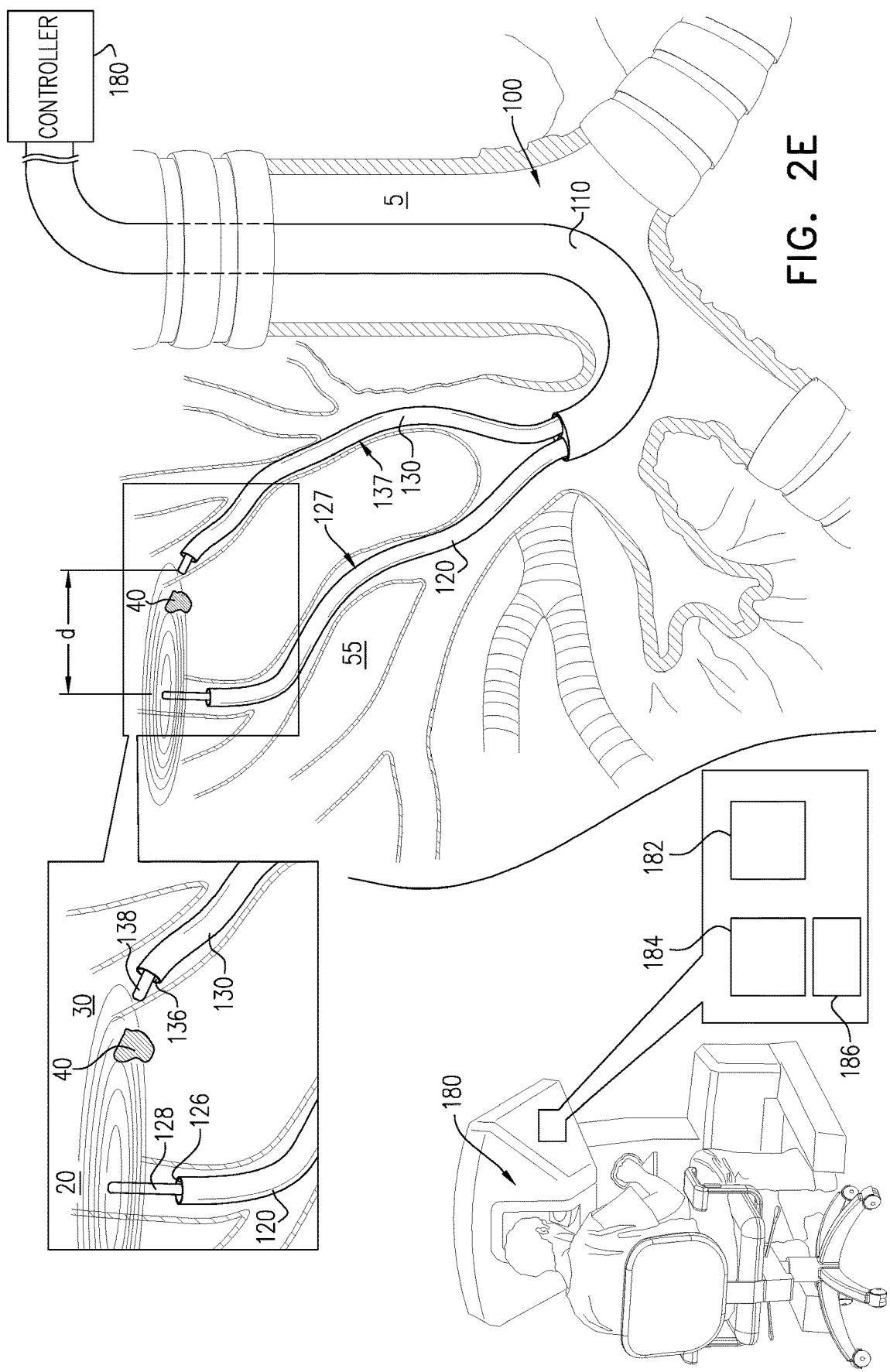

TWO-PRONGED APPROACH FOR BRONCHOSCOPY

This application is a National Phase of PCT Patent Application No. PCT/IB2022/057505 having International filing date of Aug. 11, 2022, which claims priority to Provisional U.S. Patent Application 63/231,895 to Shapira et al., filed Aug. 11, 2021, and entitled "TECHNIQUES FOR ACCESSING LUNG TISSUE," the contents of which is are all incorporated herein by reference in its their entirety for all purposes.

FIELD OF THE INVENTION

Some applications of the present invention relate in general to medical procedures. More specifically, some applications of the present invention relate to performing a bronchoscopic procedure under ultrasound guidance.

BACKGROUND

Bronchoscopic procedures typically involve advancing a tube through a mouth or nose of a subject, down a trachea, and into the airways of a lung of the subject. In some instances, the bronchoscopic procedure may involve removing a foreign object that has become stuck within the lung, or performing a biopsy or treatment on tissue of the lung. In some such instances, a biopsy or treatment tool is used to perform the procedure.

SUMMARY OF THE INVENTION

The present disclosure relates to methods and systems of performing a bronchoscopic procedure guided by real-time imaging of the lungs of the subject. The method comprises using a transbronchial approach to position an imaging device in the lung of the subject, at least partly independently of the positioning of the medical tool used to perform the procedure. These techniques may advantageously allow the imaging device to be positioned optimally for viewing the operation of the medical tool at a target site within the lung. These techniques may also advantageously allow for repositioning of the imaging device (e.g. mid-procedure) without undesirably also repositioning the medical tool.

Typically, prior to the procedure, the target site to be operated on (hereinbelow referred to as "the target") and/or one or more routes to the target are predetermined (e.g. pre-procedurally designated)—e.g. facilitated by pre-procedure imaging such as, but not limited to, CT or MRI. However, the procedure may alternatively be performed as part of an exploratory bronchoscopy procedure—e.g. with the routes and/or target being determined intraoperatively. Examples of targets include tumors, lesions, or foreign objects trapped in the lung. The procedure may involve performing a biopsy on the target, or removing the target.

The method may comprise advancing a sheath into a trachea of a subject. The sheath may be advanced into a bronchus of the lung. The target may be significantly distal to the primary and/or secondary bronchi of the lung, for example, it may be in a fourth, fifth, sixth, or greater generation of the bronchi, or even in the bronchioles of the lung. The target may even be situated outside of the bronchi—e.g. in the parenchyma. Typically, advancement of the sheath is terminated prior to the sheath reaching the target, such that the distal end of the sheath is proximal from (i.e. less deep into the airways) than the target itself. For example, the sheath may be advanced only as far as the trachea, or only as far as a primary bronchus, whereas the target may be situated at, or adjacent to, a third-, fourth-, fifth-, sixth-, or higher-generation bronchus. In some applications, the sheath is not advanced into the trachea or bronchus (e.g. it may be placed into the mouth of the patient but does not reach the trachea).

Two flexible tubes (e.g. two catheters) are then advanced out of the sheath and along alternate routes, branching away from each other as they progress deeper into the lung, such that the ends of the tubes become disposed in different bronchi or bronchioles. For example, the end of the first tube may become disposed in a first sixth-generation bronchus, and the end of the second tube may become disposed in a different sixth-generation bronchus. Alternatively, the first tube may be advanced to a different generation-depth than the second tube, for example the first tube may be advanced only to a fourth-generation bronchus, with the second tube advanced to a seventh-generation bronchus. Advancement of the sheath may be terminated at a fork in the airways that has been predetermined to be appropriate for advancement of both the first and second tubes—e.g. the fork being common to the first and second routes. In some applications, the first tube and the second tube are advanced individually through the trachea and into the airways without use of a sheath.

Although the first and second tubes may initially diverge as each is advanced along a different airway branch, they may subsequently converge as they approach the target. That is, the distal part of the first route, along which the first tube advances, may converge with the distal part of the second route, along which the second tube advances.

In some applications, each of the first and second tubes is guided towards its respective site using a camera disposed at its distal end to provide an operator with a view of the airways. In some such applications, these cameras are additionally used to guide the passage of the sheath down the trachea and into the bronchus, e.g. with the tubes disposed within the sheath and the cameras disposed at the distal ends of the tubes, which themselves are close to or at the distal end of the sheath.

In some applications in which cameras are used to direct the tubes towards their respective sites, once the tubes are positioned at their respective sites, the cameras may be withdrawn through the tubes and out of the subject. In some applications, an ultrasound transceiver is then passed through the first tube and out of the first tube's distal end, and a medical tool is passed through the second tube, and out of the second tube's distal end. In some applications, a camera is disposed at the distal end of the sheath, external to the tubes, such that the camera may remain in place while the tubes are advanced beyond the end of the sheath, or while the tool or the ultrasound transceiver are passed through the tubes.

For some applications, one or both of the cameras may remain at the distal end of the tubes, and an ultrasound transceiver may be delivered through a working channel of the first tube and out of its distal end, and/or a medical tool may similarly be delivered through a working channel of the second tube and out of its distal end.

In some applications, the first tube is advanced to the imaging site with an ultrasound transceiver already disposed at its distal end, and the second tube is advanced to the tool site with the medical tool already at its distal end.

The imaging and tool sites are typically chosen (e.g. designated) such that the target and the tool will be in the field of view of the ultrasound transceiver. For example, the target may be disposed between the ultrasound transceiver and the medical tool—e.g. with the ultrasound transceiver "looking back" or "looking over" at the target and the medical tool. Alternatively, the medical tool may be closer than the target to the ultrasound transceiver—e.g. with the target behind the medical tool, from the perspective of the ultrasound transceiver.

In some applications, the sites and/or routes are pre-procedurally planned (i.e. designated), e.g. in order to provide a viable pair of sites for the transceiver and tool during the procedure. The pre-procedure planning of the sites and/or routes may be performed manually—e.g. by a physician. However, the planning may alternatively be facilitated at least in part by a system, e.g., a data-processing system or a computer processor, running software and/or an algorithm. Route planning may be facilitated by a computer model (e.g. a schematic representation and/or an image) of the lung of the subject, which may be derived from an initial imaging of the lung, such as a three-dimensional (3D) CT or MRI image. The computer model typically includes a representation of the target site and of the airways of the lung. In some applications, the representation may include a volumetric body. In some applications, the representation may include a vector-based map. In some applications, both a volumetric body and vectors may be used to generate the airway representation. The representation of the airways is typically generated by computer-based image processing—e.g. of the 3D image. The representation of the target site may be generated either by such image processing, by identification by a human (e.g. a physician), and/or by a combination of both.

The generation of the computer model may be performed by a model-generation module—e.g. a data-processing system or a component thereof.

The route planning may be performed by a map-generation module (e.g. a data-processing system or a component thereof) that, utilizing the computer model, generates a map that includes the pair of routes.

The designation of the sites and/or the routes may be based on one or more parameters of input data, which are typically parameters of the lung/airways and/or characteristics of the system to be used. Parameters of the lung/airways may, e.g., be derived from the computer model, and/or may include, e.g., anatomical features in the target vicinity; distances among tool site, imaging site, and target; airway diameters and branching patterns; distance from the trachea to the target along the airways; and size of the target. Characteristics of the system may include, e.g., features of the ultrasound transducer and/or the tool; details of the tube (e.g. catheter) model; and type of system and/or controller. Typically, site and/or route designations are generated by a data-processing system (e.g. running programs and/or algorithms) that uses one or more such parameters as inputs. In an exemplary application, input data may be grouped into two or more clusters of related parameters, e.g., imaging-route parameters, tool-route parameters, and route-pairing parameters. In other applications, input data may be grouped into other clusters, e.g., hardware parameters, operator preferences, subject parameters, target, and 3D imaging information.

Because the imaging and tool sites are typically designated such that the target and the tool will appear in the field of view of the ultrasound transceiver, the imaging and tool sites and/or routes are typically designated as pairs. That is, rather than merely assessing a quality of a given potential imaging site/route in isolation, or a quality of a given potential tool site/route in isolation, the designation techniques/algorithms disclosed herein typically assess these sites/routes as potential pairs—each potential pair including a potential imaging site/route and a potential tool site/route. For example, a potential pair may only be considered suitable if (i) the target and the tool site of the pair are within the effective imaging range of the imaging site, and (ii) both the imaging site and the tool site are accessible by their respective tubes.

In some applications, the system includes a robotic controller (e.g. including a robotic-control module) used to advance the sheath and/or tubes towards their respective sites—e.g. by controlling a robotic manipulator that is couplable to the tubes. The robotic manipulator may be a component of the robotic controller, or may be electronically connectable to the robotic controller.

For some such applications, the computer model of the lung/airways may be used to determine the position of the first and second tubes as they are advanced within the airways, e.g. by mapping, onto the computer model, real-time positioning data—e.g. imaging data generated from ultrasound transceiver(s) and/or camera(s) at the end of the tubes, and/or data (e.g. electromechanical data) from sensors on the tubes and/or the robotic manipulator. Such route tracking may be performed by a route-tracking module (e.g. a data-processing system or a component thereof) that, utilizing the map and the real-time positioning data, tracks the advancement of the tubes along the routes. The imaging and tool sites are typically present in (e.g. pre-entered into) the map, such that the route-tracking module can assess whether the tubes are correctly positioned at their respective sites.

The robotic-control module and the route-tracking module may be components of the same data-processing system (e.g. computer) via which the operator advances the tubes. For example, these modules may both be components of the robotic controller.

In some applications, after positioning the ultrasound transceiver at the imaging site and the tool at the tool site, positioning (e.g. alignment) of the ultrasound transceiver and the tool may be further refined by driving an electromagnetic signal through the tool and sensing the electromagnetic signal via the ultrasound transceiver. The signal may be used to facilitate reduction of the distance between the ultrasound transceiver and the tool. For example, the distance-reduction may be guided by a strength of the signal increasing with reduction of the distance. Reducing the distance may be achieved moving the ultrasound transceiver toward the tool, and/or moving the tool toward the ultrasound transceiver. For some applications, the signal may be observed as interference on the ultrasound image obtained from the ultrasound transceiver. For some applications, a computer-generated estimate of the distance between the ultrasound transceiver and the tool may be generated responsively to the intensity of the signal.

In some applications, the ultrasound transceiver acquires multiple two-dimensional (2D) images of the target and its proximity. These two-dimensional images may be stacked by a data-processing device during the procedure to provide near real-time, updateable 3D image of the target. In applications in which the tool appears in the 2D images, the data-processing device may be configured to refine the 3D image by aligning the 2D images according to a known shape of the tool.

There is therefore provided, in accordance with an application of the present invention, a method for use with a lung of a subject, the method including, a method for use with a lung of a subject, the method including:

via a trachea of the subject, advancing an end of a first tube along a first airway route to an imaging site within the lung; and/or via the trachea of the subject, and independently of advancing the end of the first tube, advancing an end of a second tube along a second airway route to a tool site within the lung.

For some applications, the method further includes, while the first tube remains extended along the first route and the second tube remains extended along the second route:

using an imaging device extended from the end of the first tube, imaging (i) a tool extended from the end of the second tube, and (ii) a target within the lung; and/or guided by the imaging of the target and the tool, performing a procedure on the target using the tool.

For some applications:

the method further includes advancing a sheath via the trachea toward the lung;

advancing the end of the first tube includes extending the first tube out of the sheath; and/or advancing the end of the second tube includes extending the second tube out of the sheath independently of extending the first tube out of the sheath.

For some applications, the sheath defines a first lumen and a second lumen.

For some applications, advancing the end of the first tube along the first route includes advancing the end of the first tube along the first route while the first tube is extended through the first lumen.

For some applications, advancing the end of the second tube along the second route includes advancing the end of the second tube along the second route while the second tube is extended through the second lumen.

For some applications, advancing the distal part of the sheath includes actively steering the distal part of the sheath using an extracorporeal sheath controller.

For some applications, performing the procedure on the tissue includes performing the procedure while the tissue is disposed between the imaging device and the tool.

For some applications, performing the procedure on the tissue includes performing the procedure while the tool is closer than the tissue to the imaging device.

For some applications, performing the procedure on the tissue includes performing the procedure while the tissue is behind the tool, in a field of view of the imaging device.

For some applications, advancing the first tube along the first route to the imaging site includes advancing the first tube along the first route to the imaging site while the imaging device is disposed at the end of the first tube.

For some applications, advancing the second tube along the second route to the tool site includes advancing the second tube along the second route to the tool site while the tool is disposed at the end of the second tube.

For some applications, the method further includes, subsequently to advancing the end of the first tube to the imaging site, advancing the imaging device through the first tube, and out of the end of the first tube.

For some applications, the method further includes, subsequently to advancing the end of the second tube to the tool site, advancing the tool through the second tube, and out of the end of the second tube.

For some applications, the sheath defines a first lumen and a second lumen, and:

advancing the end of the first tube along the first route includes advancing the end of the first tube along the first route while the first tube is extended through the first lumen, and advancing the end of the second tube along the second route includes advancing the end of the second tube along the second route while the second tube is extended through the second lumen.

For some applications, advancing the distal part of the sheath includes actively steering the distal part of the sheath using an extracorporeal sheath controller.

For some applications, advancing the end of the first tube includes actively steering the first tube using an extracorporeal first-tube controller.

For some applications, advancing the end of the second tube includes actively steering the second tube using an extracorporeal second-tube controller.

For some applications, performing the procedure includes performing the procedure while continuing to image the tissue using the imaging device.

For some applications, imaging the tissue includes acquiring one or more images that include the tool.

For some applications, the imaging device includes an ultrasound transceiver, and imaging the tissue includes imaging the tissue using the ultrasound transceiver.

For some applications, the imaging device is a LIDAR device, and imaging the tissue includes imaging the tissue using the LIDAR device.

For some applications, the tissue is located within a target bronchus of the lung, and advancing the end of the second tube along the second route to the tool site includes advancing the end of the second tube intrabronchially along the second route to the target bronchus.

For some applications:

the tool site is within a target bronchus of the lung, the tissue is parenchyma of the lung and situated outside the target bronchus of the lung, advancing the end of the second tube along the second route to the tool site includes advancing the end of the second tube along the second route to the tool site that is within the target bronchus, and performing the procedure on the tissue using the tool extended from the end of the second tube includes extending the tool, from the end of the second tube, through a wall of the target bronchus and towards the parenchyma.

For some applications:

the tool includes a tool element selected from the group consisting of: a needle, a blade, scissors, a suction device, jaws, a grasper, an ablation device, and an energy applicator; and performing the procedure on the tissue using the tool includes performing the procedure on the tissue using the tool that includes the selected tool element.

For some applications, performing the procedure includes ablating the tissue.

For some applications, performing the procedure includes excising a foreign body from the lung.

For some applications, the procedure is a close-up imaging procedure, the tool is a close-up imaging device, and performing the procedure includes performing the close-up imaging procedure.

For some applications, the procedure is an exploratory procedure, and performing the procedure includes performing the exploratory procedure on the tissue.

For some applications:

the tissue is situated outside of an airway of the lung, the tool site is within the airway, advancing the end of the second tube along the second route to the tool site includes advancing the end of the second tube along the second route to the tool site that is within the airway, and performing the procedure on the tissue using the tool extended from the end of the second tube includes extending the tool through a wall of the airway and into the tissue.

For some applications:

performing the procedure on the tissue using the tool extended from the end of the second tube includes performing a first part of the procedure on the tissue using the tool extended from the end of the second tube, and the method further includes, subsequently to performing the first part of the procedure, and while the end of the first tube remains at the imaging site:
  withdrawing the imaging device from the first tube;
  withdrawing the tool from the second tube;
  subsequently, advancing the tool through the first tube; and
  subsequently, performing a second part of the procedure on the tissue using the tool extended from the end of the first tube.

For some applications:

the method further includes, subsequently to withdrawing the imaging device from the first tube and the tool from the second tube, and while the end of the second tube remains at the tool site, advancing the imaging device through the second tube, and performing the second part of the procedure includes performing the second part of the procedure, guided by imaging of the tissue by the imaging device at the end of the second tube.

For some applications, the method further includes extracorporeally imaging the tissue while advancing the end of the first tube, and advancing the end of the first tube includes advancing the end of the first tube guided by the extracorporeal imaging of the tissue.

For some applications, extracorporeally imaging the tissue includes extracorporeally imaging the tissue ultrasonically.

For some applications, extracorporeally imaging the tissue includes extracorporeally imaging the tissue using electromagnetic radiation.

For some applications, extracorporeally imaging the tissue includes extracorporeally imaging the tissue magnetically.

For some applications, performing the procedure includes excising the tissue.

For some applications, excising the tissue includes excising a lesion.

For some applications, excising the tissue includes excising a tumor.

For some applications, excising the tissue includes acquiring a biopsy.

For some applications:

the bronchus is a bronchus of a given bronchus generation, at a fork, the bronchus forks distally into a first branch and a second branch, advancing the distal part of the sheath into the bronchus includes advancing the distal part of the sheath into the bronchus, not beyond the fork, and advancing the end of the first tube along the first route to the imaging site includes advancing the end of the first tube beyond the fork, and via the first branch to the imaging site.

For some applications, advancing the end of the second tube along the second route to the tool site includes advancing the end of the second tube beyond the fork, and via the second branch to the tool site.

For some applications, the imaging site is situated, along the first route, at a different bronchus-generational depth than is the tool site, along the second route.

For some applications, the imaging site is situated, along the first route, at a same bronchus-generational depth as is the tool site, along the second route.

For some applications, advancing the end of at least one tube selected from the group consisting of: the first tube and the second tube, along its respective route, includes advancing the end of the at least one selected tube along its respective route guided by a respective camera disposed at the end of the at least one selected tube.

For some applications, advancing the distal part of the sheath into the bronchus includes advancing the distal part of the sheath into the bronchus guided by the respective camera disposed at the end of the at least one selected tube.

For some applications:

advancing the end of the first tube along the first route includes advancing the end of the first tube along the first route, guided by a first camera disposed at the end of the first tube, advancing the end of the second tube along the second route includes advancing the end of the second tube along the second route, guided by a second camera disposed at the end of the second tube, and advancing the distal part of the sheath into the bronchus includes advancing the distal part of the sheath into the bronchus guided by binocular vision provided by the first camera and the second camera.

For some applications, the method further includes, subsequently to advancing the end of the at least one selected tube, withdrawing the respective camera from the selected tube and out of the subject.

For some applications, performing the procedure on the tissue using the tool extended from the end of the second tube, includes performing the procedure on the tissue using the tool extended from the end of the second tube without withdrawing the respective camera from the selected tube.

For some applications, the respective camera includes a light source.

For some applications, subsequently to (i) advancing the end of the first tube to the imaging site, and (ii) advancing the end of the second tube to the tool site, determining a presence of the tissue and the tool in a field of view of the imaging device.

For some applications, the method further includes, subsequently to determining the presence of the tissue and the tool in the field of view, repositioning the tool with respect to the imaging device and the tissue while retaining the tool in the field of view.

For some applications, the method further includes, subsequently to determining the presence of the tissue and the tool in the field of view, repositioning the imaging device with respect to the tool and the tissue while retaining the tool in the field of view.

There is further provided, in accordance with an application of the present invention, a method for use with a lung of a subject, the method including, via a trachea of the subject, advancing a distal part of a sheath into a bronchus of the lung.

The method may further include, while the distal part of the sheath remains disposed within the bronchus, using imaging derived from an ultrasound transceiver disposed at the distal part of the sheath:

guiding a distal part of a first tube out of the distal part of the sheath and along a first route to an imaging site within the lung; and/or guiding a distal part of a second tube out of the distal part of the sheath and along a second route to a tool site within the lung.

The method may further include, while the first tube remains extended along the first route and the second tube remains extended along the second route, guided by imaging derived from an imaging device disposed at the distal part of the first tube, performing a procedure on tissue of the lung using a tool at the distal part of the second tube.

For some applications:

at a fork, the bronchus forks distally into a first branch and a second branch, the first route includes the first branch, the second route includes the second branch, and/or advancing the distal part of the sheath into the bronchus includes advancing the distal part of the sheath into the bronchus not beyond than the fork.

For some applications, the ultrasound transceiver is coupled to the distal part of the sheath, and advancing the distal part of the sheath into the bronchus of the lung includes advancing the distal part of the sheath while the ultrasound transceiver is coupled to the distal part.

For some applications, the ultrasound transceiver has a longer-distance field of view than the imaging device.

For some applications, the imaging device has an effective imaging range, and guiding the distal part of the first tube out of the distal part of the sheath and along the first route to the imaging site within the lung includes:

guiding the distal part of the first tube to the imaging site such that the first tube is within the effective imaging range of a target within the lung; and/or guiding the distal part of the second tube to the tool site such that the second tube is within the effective imaging range of the imaging device.

For some applications, further including a third tube, the ultrasound transceiver being disposed at a distal section of the third tube, and the method further includes advancing the third tube to the bronchus of the lung, within the sheath.

For some applications, the method further includes advancing the third tube out of the distal part of the sheath.

For some applications, the ultrasound transceiver is a first ultrasound transceiver, and the imaging device is a second ultrasound transceiver.

For some applications, the first ultrasound transceiver is a lower-frequency transceiver than is the second ultrasound transceiver.

There is further provided, in accordance with an application of the present invention, a method for pre-procedurally planning routes through airways of a lung of a subject toward a target site within the lung.

For some applications, building the map that includes a pair of routes includes building the map such that the imaging route and the tool route converge toward the target.

For some applications, the method further includes building the computer model of the lung.

For some applications, building the computer model of the lung includes: generating the representation of the airways from a 3D image of the lung; and incorporating the target into the model.

For some applications, incorporating the target into the model includes receiving an input indicative of the target location and incorporating the input into the computer model.

For some applications: incorporating the target into the model includes incorporating a user-selected target into the model, and the method further includes, prior to incorporating the target into the model: identifying, from the 3D image, one or more potential targets, prompting a user to select the user-selected target from the one or more potential targets, and receiving a user input indicative of the user-selected target.

For some applications: the method further includes receiving an exit-point input indicative of a preferred exit point, within the computer model, for the tool to exit an airway of the lung toward the target, and building the map includes building the map responsively to the exit-point input.

For some applications, the exit-point input is inputted by a user, and receiving the exit-point input includes receiving the user-inputted exit-point input.

For some applications: the exit-point input includes an exit-point coordinate on the computer model, and building the map includes building the map responsively to the exit-point coordinate.

For some applications: the exit-point input includes an exit direction with respect to the airway, and building the map includes building the map responsively to the exit direction.

For some applications: the method further includes receiving, within the computer model, an exclusion-zone input indicative of an exclusion zone within the lung, and building the map includes building the map such that the tool route and the imaging route avoid the exclusion zone.

For some applications, the exclusion-zone input is computer generated, and receiving the exclusion-zone input includes receiving the computer-generated exclusion-zone input.

For some applications: the exclusion-zone input is indicative of a blood vessel within the lung, and building the map includes building the map such that the tool route and the imaging route avoid the blood vessel.

For some applications: the exclusion-zone input is indicative of a nerve plexus within the lung, and building the map includes building the map such that the tool route and the imaging route avoid the nerve plexus.

For some applications: the exclusion-zone input is indicative of a pleural lining within the lung, and building the map includes building the map such that the tool route and the imaging route avoid the pleural lining.

For some applications: the method further includes receiving a preference input indicative of an operator preference, and building the map includes building the map at least in part responsively to the preference input.

For some applications: the preference input is indicative of a preferred viewing angle for the imaging device, and building the map includes building the map responsively to the preference input indicative of the preferred viewing angle for the imaging device.

For some applications: the preference input is indicative of an upper limit for the length of the tool route, and building the map includes building the map responsively to the preference input indicative of the upper limit.

For some applications: the preference input is indicative of an upper limit for a number of airway bifurcations within the tool route, and building the map includes building the map responsively to the preference input indicative of the upper limit.

For some applications: the preference input is indicative of an upper limit for a sharpness of any turn within the tool route, and building the map includes building the map responsively to the preference input indicative of the upper limit.

For some applications: the preference input is indicative of a preferred intracorporeal proximity of the image device to the tool, and building the map includes building the map responsively to the preference input indicative of the preferred intracorporeal proximity of the image device to the tool.

For some applications: the preference input is indicative of a user weighting between a first factor and a second factor, and building the map includes building the map responsively to the preference input indicative of the user weighting.

For some applications: the first factor is a viewing angle for the imaging device, the second factor is an angle-of-attack for the tool, the user weighting is a weighting between optimizing the viewing angle versus optimizing the angle-of-attack, and building the map includes building the map responsively to the preference input indicative of the user weighting between optimizing the viewing angle versus optimizing the angle-of-attack.

For some applications, the method further includes receiving a hardware input indicative of a hardware parameter, and building the map includes building the map at least in part responsively to the hardware input.

For some applications, the hardware parameter is a model of the imaging device, and building the map includes building the map responsively to the hardware input that is indicative of the model of the imaging device.

For some applications, the tool route is for advancement of the tool to the tool site via a tube, and for advancement of the tube to the tool site, the hardware parameter is a parameter of the tube, and building the map includes building the map responsively to the hardware input that is indicative of the parameter of the tube.

For some applications, the hardware parameter is a model of an extracorporeal controller for controlling advancement of the tube, and building the map includes building the map responsively to the hardware input that is indicative of the model of the extracorporeal controller.

For some applications, the parameter of the tube is a diameter of the tube, and building the map includes building the map responsively to the hardware input that is indicative of the diameter of the tube.

For some applications, the parameter of the tube is a bendability parameter of the tube, and building the map includes building the map responsively to the hardware input that is indicative of the bendability parameter of the tube.

For some applications, the hardware parameter is a parameter of the tool, and building the map includes building the map responsively to the hardware input that is indicative of the parameter of the tool.

For some applications, the parameter of the tool is a flexibility of the tool, and building the map includes building the map responsively to the hardware input that is indicative of the flexibility of the tool.

For some applications, the parameter of the tool is a type of the tool, and building the map includes building the map responsively to the hardware input that is indicative of the type of the tool.

For some applications, the parameter of the tool is a dimension of the tool, and building the map includes building the map responsively to the hardware input that is indicative of the dimension of the tool.

For some applications, the dimension of the tool is a width of the tool, and building the map includes building the map responsively to the hardware input that is indicative of the width of the tool.

The method may further include receiving a computer model of the lung, the model including a target within the lung and a representation of the airways.

The method may further include, using the computer model, building a map that includes: a tool route to a tool site within the computer model of the lung, for advancement of a tool for use at the target, and an imaging route to an imaging site within the computer model of the lung, for advancement of an imaging device, at least a distal portion of the imaging route being distinct from a distal portion of the tool route.

For some applications: the computer model includes a designated preferable angle of approach with respect to the target, generated responsively to receipt of a user input that designates the preferable angle of approach with respect to the target, and building the map includes building the map at least in part responsively to the designated preferable angle of approach with respect to the target.

For some applications: the computer model is derived from pre-procedural imaging of the lung; and receiving the computer model includes receiving the computer model that is derived from the pre-procedural imaging of the lung.

For some applications: the pre-procedural imaging is generated using electromagnetic radiation; and receiving the computer model that is derived from the pre-procedural imaging includes receiving the computer model that is derived from the pre-procedural imaging generated using electromagnetic radiation.

For some applications: the pre-procedural imaging is generated magnetically; and receiving the computer model that is derived from the pre-procedural imaging includes receiving the computer model that is derived from the pre-procedural imaging generated magnetically.

For some applications: the computer model is a schematic representation of airways of the lung; and receiving the computer model includes receiving the computer model that is a schematic representation of airways of the lung.

For some applications: the computer model is an image of the lung; and receiving the computer model includes receiving the computer model that is an image of the lung.

For some applications: the computer model includes a schematic representation of the airways, generated by computer processing of the pre-procedural imaging, and receiving the computer model includes receiving the computer model that includes the schematic representation of the airways.

For some applications, the method further includes generating the schematic representation of the airways by computer processing of the pre-procedural imaging.

For some applications, the computer model includes a schematic representation of the target, and/or receiving the computer model includes receiving the computer model that includes the schematic representation of the target.

For some applications, the method further includes generating the schematic representation of the target by computer processing of the pre-procedural imaging.

For some applications, the method further includes generating the schematic representation of the target responsively to receipt of a user input that designates the target.

For some applications, the computer model includes a designated preferable angle of approach with respect to the target, generated responsively to receipt of a user input that designates the preferable angle of approach with respect to the target, and/or receiving the computer model includes receiving the computer model that includes the designated preferable angle of approach with respect to the target.

For some applications, building the map includes designating at least one site selected from the group consisting of: the imaging site and the tool site, responsively to one or more characteristics of the imaging device.

For some applications, building the map includes designating the selected site responsively to an effective imaging range of the imaging device.

For some applications, building the map includes designating the selected site responsively to a manipulability of the imaging device.

For some applications, building the map includes designating at least one site selected from the group consisting of: the imaging site and the tool site, responsively to one or more characteristics of the tool.

For some applications, building the map includes designating the selected site responsively to an effective operating range of the tool.

For some applications, building the map includes designating the selected site responsively to a manipulability of the tool.

For some applications: the map further includes: a sheath-termination site in a bronchus of the lung, and a sheath route, for advancement of a distal end of a sheath to the sheath-termination site, and building the map includes designating the sheath-termination site within the map.

For some applications, the sheath route is common to both the tool route and the imaging route, and building the map includes designating the sheath route that is common to both the tool route and the imaging route.

For some applications, building the map includes designating, within the map, at least one site selected from the group consisting of: the imaging site and the tool site, by determining a predicted presence of the tool at the tool site, within a predicted field of view of the imaging device at the imaging site.

For some applications, building the map includes designating the selected site responsively to an anticipated field of view of the imaging device at the imaging site.

For some applications, building the map includes designating the selected site responsively to at least one parameter of the group consisting of: (i) a proximity of the imaging site to the tool site, and (ii) a proximity of the tool site to the target.

For some applications, building the map includes designating the selected site responsively to on a presence of structures between the imaging site and the tool site.

For some applications, designating the tool site and the imaging site includes designating the tool site and the imaging site manually.

For some applications, building the map includes designating at least one site selected from the group consisting of: the imaging site and the tool site, responsively to at least one parameter of the group consisting of: (i) ease of access to the imaging site and (ii) ease of access to the tool site.

For some applications, building the map includes designating the selected site responsively to at least one parameter of the group consisting of: (i) ease of navigation of a first tube to the imaging site, for advancement of the imaging device, and (ii) ease of navigation of a second tube to the tool site, for advancement of the tool.

For some applications, designating the tool site includes designating the tool site responsively to a predicted accessibility of the tool to the target from the tool site.

For some applications, the method further includes assessing a potential route selected from the group consisting of: the tool route and the imaging route, by simulating the respective tube being advanced to its respective site, via the respective route.

For some applications, assessing a potential route includes providing the simulating of the respective tube being advanced to its respective site as a virtual tour to a human operator.

For some applications, building the map includes designating at least one site selected from the group consisting of: the imaging site and the tool site, responsively to at least one parameter of the group consisting of: (i) a predicted orientation of the imaging device upon arrival at the imaging site and (ii) a predicted orientation of the medical tool upon arrival at a potential tool site.

For some applications, building the map includes designating the selected site responsively to at least one parameter of the group consisting of: (i) a predicted ability to reorient the imaging device at the imaging site, and (ii) a predicted ability to reorient the tool at the tool site.

For some applications, the step of building the map is performed by a computer processor processing an algorithm.

For some applications, the method further includes procuring a plurality of potential pairs, each pair including (i) a potential imaging site and (ii) a potential tool site, and building the map includes assigning a suitability score to each potential pair of the plurality.

For some applications, for each of the pairs of the plurality, procuring the pair includes selecting the tool site of the pair, and subsequently procuring a plurality of potential imaging sites for the selected tool site of the pair.

For some applications, for each of the pairs of the plurality, procuring the pair includes selecting the imaging site of the pair, and subsequently procuring a plurality of potential tool sites for the selected imaging site of the pair.

For some applications, building the map includes assigning the suitability score using artificial intelligence to calculate the suitability score.

There is further provided, in accordance with an application of the present invention, a method for use with a lung of a subject, the method including, via a trachea of the subject, advancing a distal part of a sheath into a bronchus of the lung, the lung having a first branch downstream of the bronchus and a second branch downstream of the bronchus.

The method may further include, while the distal part of the sheath remains disposed within the bronchus: guiding a distal part of a first tube out of the distal part of the sheath and along the first branch to an imaging site within the lung; and guiding a distal part of a second tube out of the distal part of the sheath and along the second branch to a tool site within the lung.

The method may further include, while the first tube remains extended along the first branch and the second tube remains extended along the second branch, guided by imaging derived from an imaging device disposed at the distal part of the first tube, performing a procedure on tissue of the lung using a tool at the distal part of the second tube.

There is further provided, in accordance with some applications, a data-processing apparatus including means for carrying out the steps of the method.

There is further provided, in accordance with some applications, a computer program including instructions which, when the program is executed by a computer, cause the computer to carry out the method.

There is further provided, in accordance with some applications, a computer-readable medium having stored thereon the computer program.

There is further provided, in accordance with some applications, a method for use with a lung of a subject, the method including: via a trachea of the subject, guiding a distal part of a first tube along a first airway route distal to the trachea to an imaging site within the lung; and guiding a distal part of a second tube along a second airway route distal to the trachea to a target within the lung; and while the first tube remains extended along the first airway route and the second tube remains extended along the second airway route, guided by images derived from an imaging device disposed at the distal part of the first tube, performing a procedure on the target using a tool extending from the distal part of the second tube to the target.

For some applications, the imaging device is an ultrasound transceiver, and performing the procedure includes performing the procedure guided by images acquired by the ultrasound transceiver.

For some applications, the images acquired by the ultrasound transceiver are planar, and performing the procedure includes performing the procedure guided by a 3D representation of the target derived from stacking the planar images.

There is further provided, in accordance with an application of the present invention, a system, for use with a lung of a subject, the system including: an imaging device, transbronchially advanceable to an imaging site within a first airway of the lung; a tool, transbronchially advanceable to a second airway of the lung; and a data processing device, placeable in electronic communication with the imaging device and the tool, and including means for carrying out a method including: using the imaging device at the imaging site, imaging a target within the lung; and responsively to the imaging, providing a visual output that facilitates guidance of the tool, from the second airway, to the target.

For some applications: the system further includes: a first transbronchially-advanceable tube having, at a distal part thereof, a first-tube steerable region; a second transbronchially-advanceable tube having, at a distal part thereof, a second-tube steerable region; and the method further includes: guiding advancement of the first tube along a first airway route to the imaging site; and guiding advancement of the second tube along a second airway route to a tool site within the second airway.

For some applications: imaging the target within the lung includes imaging the target while the imaging device is at a distal end of the first tube within the first airway, and providing the visual output includes providing the visual output while (i) the imaging device remains at the distal end of the first tube within the first airway, and (ii) the tool extends from the second tube while the second tube remains within the second airway.

There is further provided, in accordance with some applications, a data-processing system including means for carrying out the steps of the method.

There is further provided, in accordance with some applications, a computer program including instructions which, when the program is executed by a computer, cause the computer to carry out the steps of the method.

There is further provided, in accordance with some applications, a computer-readable storage medium including instructions which, when executed by a computer, cause the computer to carry out the steps of the method.

There is further provided, in accordance with some applications, a computer-implemented method for use with a lung of a subject, the method including using a robotic manipulator to advance an end of a first tube along a first airway route to an imaging site within the lung; and/or via the trachea of the subject, using the robotic manipulator to advance an end of a second tube along a second airway route to a tool site within the lung.

For some applications, the computer-implemented method further includes, while the first tube remains extended along the first route and the second tube remains extended along the second route: (i) using an imaging device extended by the robotic manipulator from the end of the first tube, imaging a target within the lung; and/or (ii) guided by the imaging of the target, performing a procedure on the target facilitated by the robotic manipulator using a tool extended from the end of the second tube.

There is further provided, in accordance with some applications, a data-processing system including means for instructing a robotic manipulator to carry out the steps of the method.

There is further provided, in accordance with some applications, a computer program including instructions which, when the program is executed by a computer, cause the computer to instruct the robotic manipulator to carry out the method.

There is further provided, in accordance with some applications, a computer-readable medium having stored thereon the computer program.

There is further provided, in accordance with an application of the present invention, a computer-implemented method for use with a tool at a target tissue, including:
  receiving shape data indicative of a three-dimensional shape of the tool;
  obtaining an ordered stack of ultrasound images, each of the ultrasound images of the stack including a respective slice of the tool and a respective slice of the target tissue; and/or
  referencing the shape data, producing an aligned ordered stack of the ultrasound images by aligning the respective slices of the tool to match, to at least a threshold degree, the three-dimensional shape indicated by the shape data.

For some applications, producing the aligned ordered stack includes producing the aligned ordered stack without reordering the ultrasound images in the stack.

For some applications, steps (b) and (c) are performed iteratively, and the method further includes outputting a video stream derived from the iteratively-produced aligned ordered stack.

For some applications, the ultrasound images are two-dimensional images, and obtaining the stack of ultrasound images includes obtaining a stack of two-dimensional images.

For some applications, aligning the respective slices of the tool is configured to predict a trajectory of the tool within the target tissue.

For some applications, at least a portion of a target appears in the respective slice of the target tissue, and aligning the respective slices of the tool is configured to predict a trajectory of the tool toward the target.

There is further provided, in accordance with an application of the present invention, a computer-implemented method for use with a needle at a target tissue, including receiving a three-dimensional (3D) image including a stack of two-dimensional (2D) images.

For some applications, at least part of the target tissue appears in the 3D image, and/or at least part of the needle appears in the 3D image, such that at least one of the 2D images includes a cross-sectional elliptical slice of the needle.

The method may further include determining an eccentricity of the cross-sectional elliptical slice. The method may further include determining an orientation of the cross-sectional elliptical slice within the 2D image.

The method may further include responsively to the eccentricity and the orientation, determining a vector of the needle within the 3D image and with respect to the target tissue.

For some applications, the method further includes displaying the 3D image, including the target tissue and the vector of the needle.

For some applications, the method further includes: responsively to determining: the eccentricity of the elliptical slice, and the orientation of the elliptical slice, adjusting the vector of the needle with respect to a target within the target tissue.

For some applications:
the at least one of the 2D images includes a first 2D image and a second 2D image,
the first 2D image includes a first cross-sectional elliptical slice of the needle, the first elliptical slice having a first eccentricity, a first orientation within the 2D image, and a first position within the 2D image, and/or
the second 2D image includes a second cross-sectional elliptical slice of the needle, the second elliptical slice having a second eccentricity, a second orientation within the 2D image, and a second position within the 2D image.

For some applications, determining the eccentricity of the elliptical slice includes determining the first eccentricity, determining the orientation of the elliptical slice within the 2D image includes determining the first orientation, and the method further includes, responsively to the first eccentricity and the first orientation, adjusting the 3D image by adjusting an alignment between the first slice and the second slice.

For some applications, adjusting the 3D image includes adjusting the 3D image responsively to the first eccentricity, the first orientation, the second eccentricity, and the second orientation.

For some applications, adjusting the 3D image includes adjusting the 3D image responsively to the first position and the second position.

There is further provided, in accordance with some applications, a data-processing apparatus including means for carrying out the steps of the method.

There is further provided, in accordance with some applications, a computer program including instructions which, when the program is executed by a computer, cause the computer to carry out the method.

There is further provided, in accordance with some applications, a computer-readable medium having stored thereon the computer program.

There is further provided, in accordance with some applications, a method, including:
advancing a tool into a subject, toward a tissue of the subject;
driving an electromagnetic signal through the tool;
advancing an ultrasound transceiver into the subject; and/or
sensing the electromagnetic signal via the ultrasound transceiver.

For some applications, the method further includes reducing a distance between the ultrasound transceiver and the tool guided by a strength of the signal increasing with reduction of the distance.

For some applications, reducing the distance includes moving the ultrasound transceiver toward the tool.

For some applications, reducing the distance includes moving the tool toward the ultrasound transceiver.

For some applications, sensing the electromagnetic signal includes sensing the electromagnetic signal while imaging the tissue with the ultrasound transceiver.

For some applications, sensing the electromagnetic signal includes sensing the electromagnetic signal as interference in an image derived from the ultrasound transceiver.

For some applications, sensing the electromagnetic signal includes sensing the electromagnetic signal intermittently.

For some applications, reducing the distance guided by the strength of the signal includes observing a computer-generated estimate of the distance, the computer-generated estimate being generated responsively to the intensity of the signal.

For some applications, the tool is formed from a metal.

For some applications, the method further includes, subsequently to reducing the distance, performing a procedure on the tissue using the tool.

For some applications, performing the procedure includes performing the procedure while the tool is in a field of view of the ultrasound transceiver.

For some applications, reducing the distance includes reducing the distance at least until the tool appears in the field of view of the ultrasound transceiver.

For some applications, sensing the electromagnetic signal includes sensing the electromagnetic signal while the tool is not in the field of view of the ultrasound transceiver.

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

BRIEF DESCRIPTION OF THE DRAWINGS

FIGS. 1, and 2A-2F are schematic illustrations of an exemplary system for performing a bronchoscopic procedure on a lung of a subject, in accordance with some applications;

DETAILED DESCRIPTION

Figure 1:
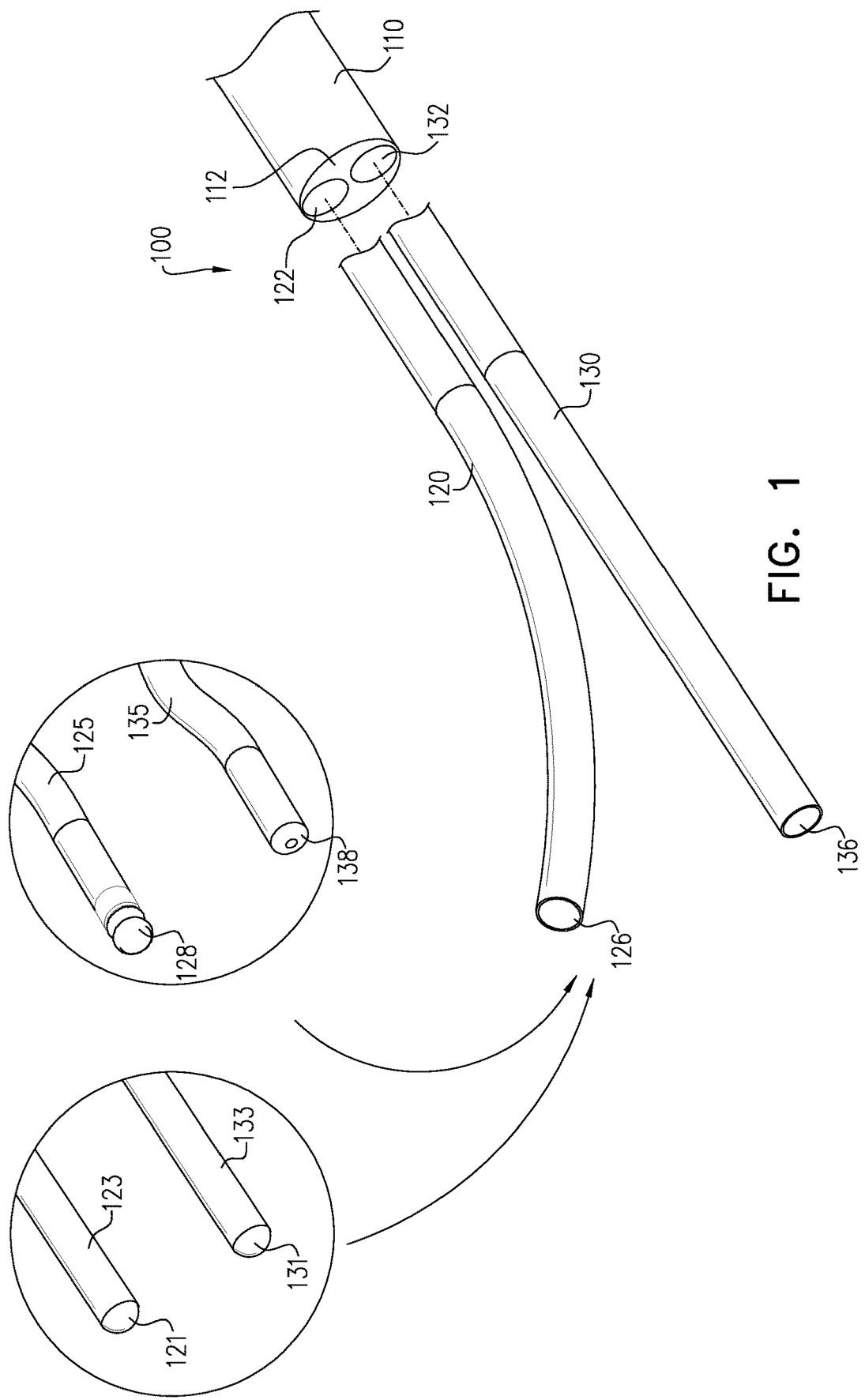

Reference is now made to FIGS. 1, 2A-2F, and 5-12, which are schematic illustrations of an exemplary system 100, and techniques for use therewith, for performing a bronchoscopic procedure on a lung 55 of a subject, in accordance with some applications. Typically, prior to the procedure, a target site to be operated on-hereinbelow referred to as target 40—and/or one or more routes to the target are predetermined. For example, this predetermination may be based on and/or facilitated by pre-procedure imaging such as, but not limited to, CT or MRI. However, the procedure may alternatively be performed as part of an exploratory bronchoscopy procedure—e.g. with the routes and/or target 40 being determined intraoperatively. Examples of targets include tumors, lesions, or foreign objects trapped in the lung. The procedure may involve, for example, performing a biopsy on target 40, ablating the target, cauterizing tissue of the target, performing localized chemotherapy on the target, performing localized radiotherapy on the target (such as performing brachytherapy and/or conformal stereotactic radiation therapy), performing cryotherapy to the target, performing an ethanol injection at the target, performing argon plasma coagulation at the target, performing photodynamic therapy at the target, or removing the target.

System 100 includes a first tube 120 and a second tube 130, and typically also includes a sheath 110 (e.g. a catheter or a tube) through which tubes 120 and 130 may extend. First and second tubes 120 and 130 are typically flexible and steerable through the airways of the subject. It is to be noted that the term "steerable" means actively steerable, e.g. in a manner that is controllable from outside of the subject, as opposed to being merely sufficiently flexible to passively bend in response to advancement through the airways.

Sheath 110 is typically also flexible, and may also be steerable. However, for some applications the sheath may be less flexible and/or less steerable than the tubes (e.g. the sheath may not be steerable and/or may be rigid). Furthermore, for some applications, system 100 does not comprise sheath 110.

Sheath 110 defines a first lumen 122 and a second lumen 132, through which first tube 120 and second tube 130, respectively, may extend. Alternatively, sheath 110 may define a single lumen, through which first tube 120 and second tube 130 are advanced. For some applications, system 100 is provided with tubes 120 and 130 separate from sheath 110, and the tubes are adapted to be advanced through the lumen(s). For some applications, system 100 is provided with tubes 120 and 130 already disposed within the lumen(s).

System 100 may further include an imaging device, such as an ultrasound transceiver 128. It should be noted that other imaging devices could also be used, such as, but not limited to, a LIDAR device, a camera, or a device for performing optical coherence tomography. Ultrasound transceiver 128 may be at a distal end of a first flexible rod 125 via which one or more wires may pass in order to provide electronic communication between the ultrasound transceiver and an extracorporeal controller 180. As described in more detail hereinbelow, during use of the ultrasound transceiver, rod 125 typically extends through first tube 120, such that the ultrasound transceiver is disposed at a distal end 126 of the first tube.

For some applications, ultrasound transceiver 128 may comprise a Radial Endobronchial Ultrasound (R-EBUS) transceiver. The transceiver may be composed of a single transceiver element that can produce a planar image (e.g. a radial and/or disc-like) image, by rotating about its own axis. In some applications, the transceiver element is additionally moved axially in order to acquire a plurality of such disc-like images. It is hypothesized that this plurality of images may provide the user with volumetric information of the lung (e.g. to provide 3D imaging).

For some applications, in order to generate these 3D images from the plurality of planar images taken by the transceiver element, controller 180 (e.g. an imaging processor thereof) may be supplied with the shape and/or size of tool 138, such that the imaging processor can use the known dimensions of the tool as a reference for stacking the two-dimensional images into a 3D image, as further described with reference to FIGS. 13A-B.

System 100 may further include a medical tool 138, such as a biopsy tool or a treatment tool. For example, tool 138 may comprise a tool element such as a needle, a blade, scissors, a suction device, jaws, a grasper, an ablation device (such as a radiofrequency ablation device), an energy applicator, a laser device (e.g. an ND-YAG laser), a cautery device (such as a device capable of performing electrocauterization, e.g. using a monopolar or bipolar technique), a brachytherapy device, a chemotherapy/radiotherapy/cryotherapy delivery device, a biopsy brush or any other suitable tool element known in the art. Medical tool 138 may be at a distal end of a second flexible rod 135 via which one or more wires may pass in order to provide electronic communication and/or mechanical communication between the medical tool and extracorporeal controller 180. As described in more detail hereinbelow, during use of the medical tool, rod 135 typically extends through second tube 130, such that the medical tool is disposed at a distal end 136 of the second tube.

For some applications, system 100 also comprises a first camera 121 and/or a second camera 131. Cameras 121 and 131 may each be disposed at a distal end of a respective elongated member 123 or 133 (e.g. a flexible rod) which, as described in more detail hereinbelow, allows such that the cameras may be positioned at distal ends of tubes 120 and 130, respectively, during advancement of the tubes through the airways of the lung. Each of cameras 121 and 131 may include a light source to facilitate imaging. For some applications, cameras 121 and 131 are in (or are placeable in) electronic or optical communication with extracorporeal controller 180, e.g. via one or more wires or optical fibers that may extend through elongated member 123 or 133, and/or through tube 120 or 130.

For some applications, rather than using tubes 120 and 130, the features and functions described for these tubes may be conferred onto rods 125 and 135, which may extend directly through the lumen(s) of sheath 110. This may be particularly feasible for applications in which cameras 121 and 131 are not used. In some such applications, a camera may be disposed through sheath 110 in parallel with, but distinct from, tubes 120 and/or 130.

Figure 5:
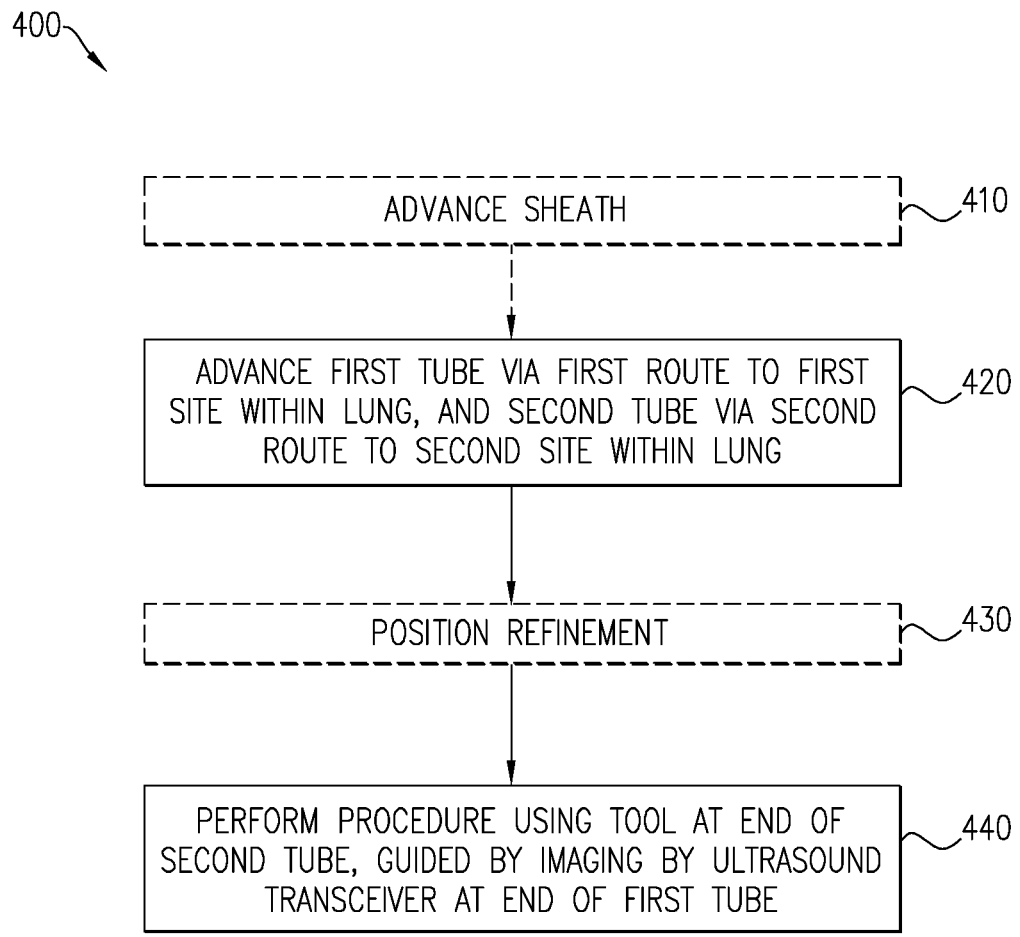
FIGS. 5-7 are flowcharts showing at least some steps of exemplary techniques for facilitating a bronchoscopic procedure on a lung of a subject, in accordance with some applications.
Figure 6:
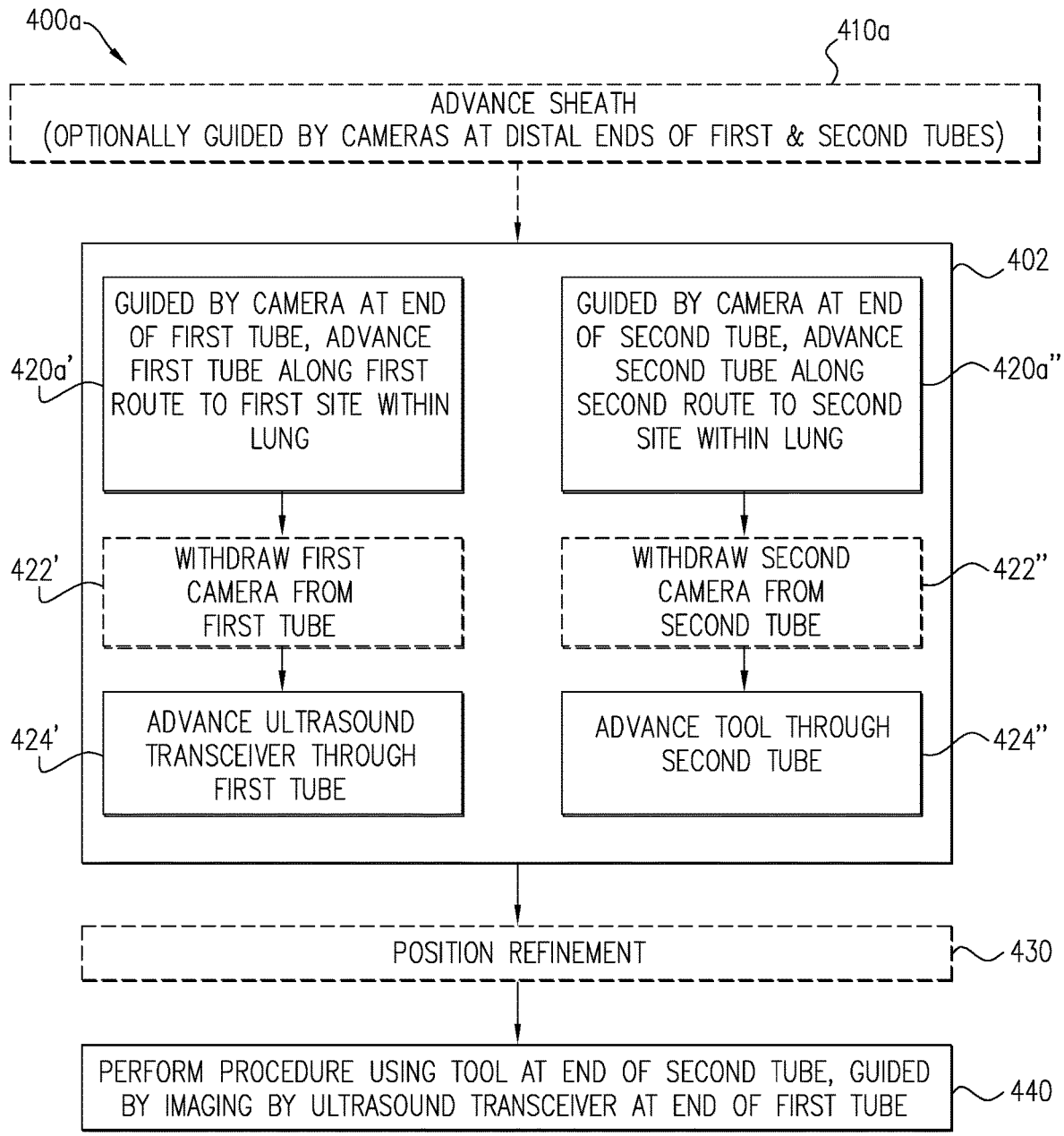
Figure 7:
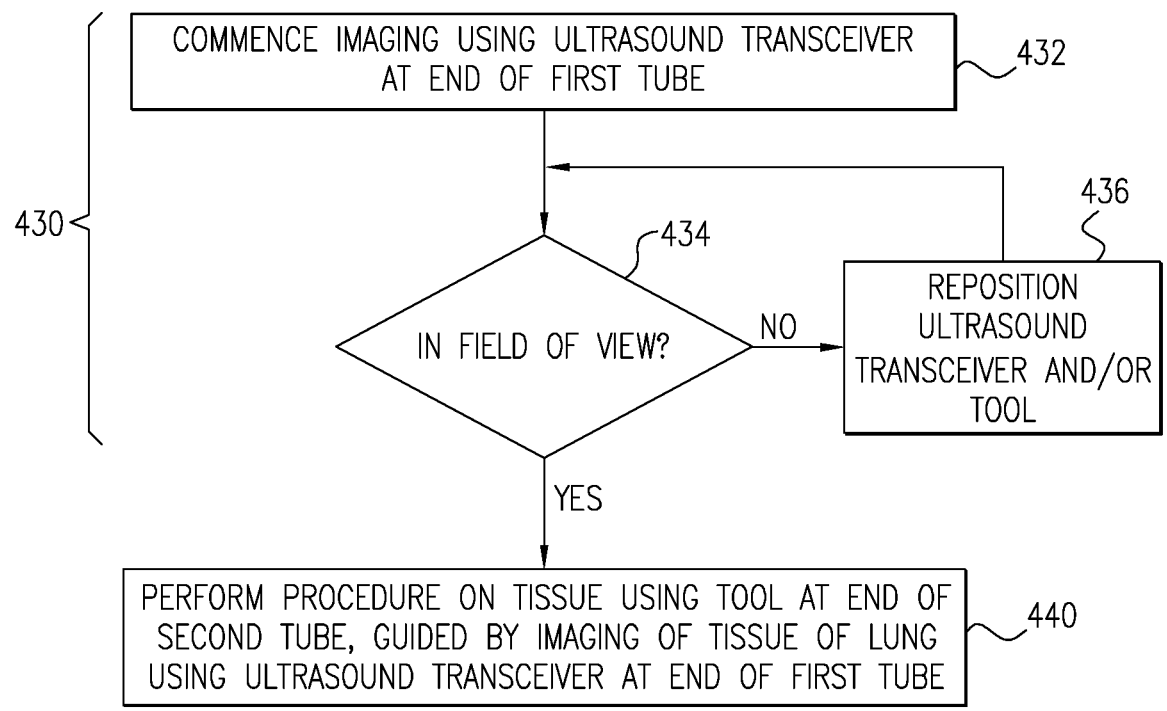

FIGS. 2A-2F, and 5-7 illustrate at least some steps of a technique for using system 100. FIG. 5 is a flowchart of at least some steps of a technique 400, which is such a technique. FIG. 6 is a flowchart detailing further steps of a technique 400a, which may be considered to be a variant of technique 400, and/or may be considered to merely expand on certain details of the technique. FIG. 7 is a flowchart expanding on certain details of a step 430 of technique 400a, for refining positions of the tool and/or the ultrasound transceiver once the first and second tubes have been positioned.

Figure 2A:
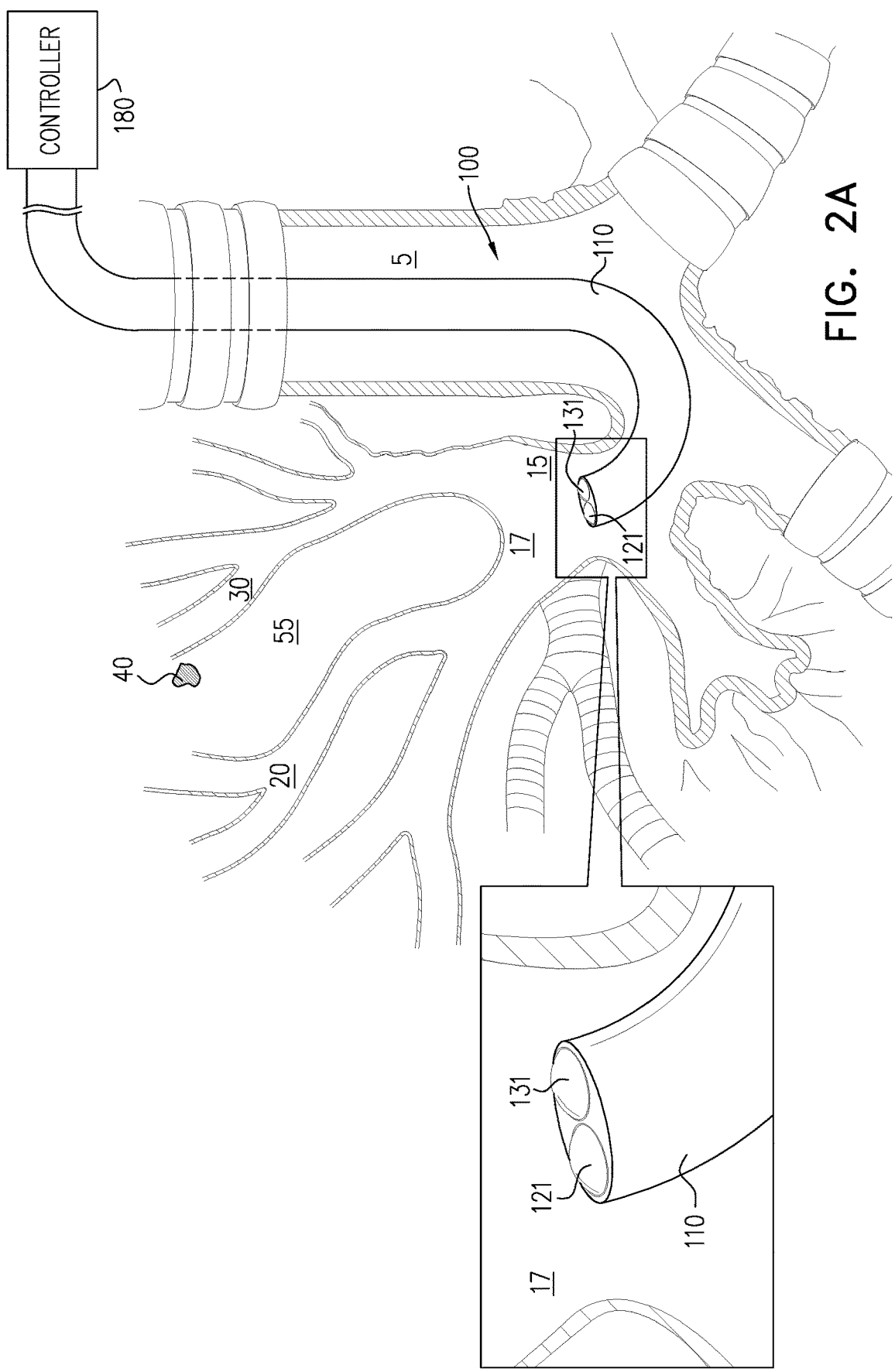

Sheath 110 may be advanced through a trachea 5 of a subject, and into a bronchus of lung 55, in the direction of target 40 (FIG. 2A, step 410 of FIG. 5, and step 410a of FIG. 6). As is shown in FIG. 2A, target 40 may be located distal (i.e. deeper into the airways, namely, at a further generational-depth with the lung) to the primary and/or secondary bronchi of the lung, for example, it may be at a fourth, fifth, sixth, or higher generation of the bronchi, or in the bronchioles of the lung. The target may even be situated outside of the bronchi or bronchioles, e.g. in the parenchyma. Typically, advancement of sheath 110 is terminated prior to the sheath reaching target 40, such that distal end 112 of the sheath is proximal (i.e. less deep into the airways) from the target itself. For example, sheath 110 may be advanced only as far as trachea 5, or may be advanced into lung 55 to, e.g., the third generation of bronchi, whereas the target may be situated at or adjacent to, e.g., a sixth-generation bronchus.

In some applications, sheath 110 is a relatively inflexible component of the catheter system, e.g., is less flexible than tubes 120 and 130. For some applications, the sheath is advanced only as far as the trachea (i.e. not into a bronchus), and/or may serve as primarily as a guide for the initial advancement of tubes 120 and 130.

It is to be noted that the use of sheath 110 is optional—e.g. represented by steps 410 and 410a having a broken outline.

Figure 2B:
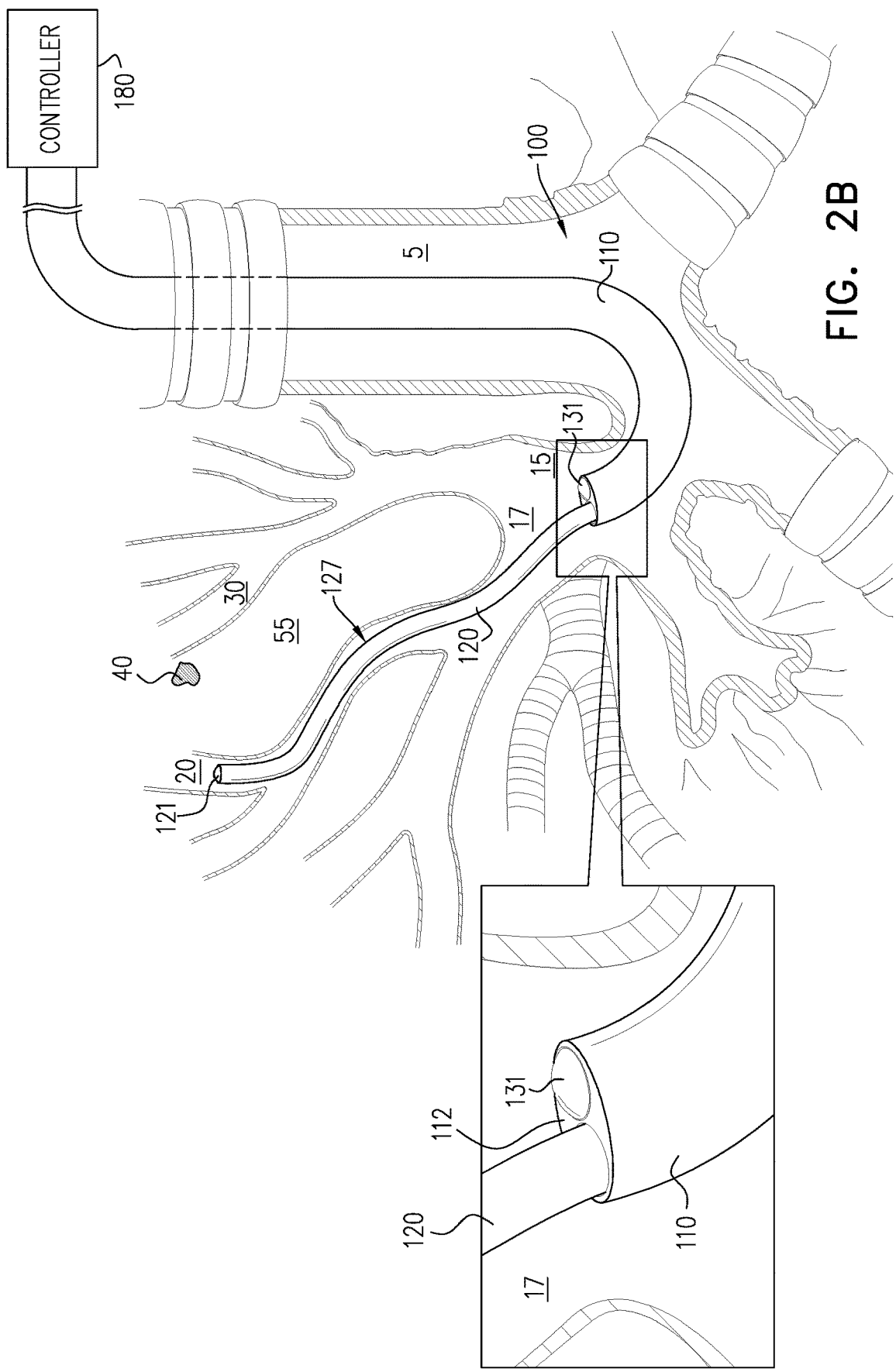
Figure 2C:
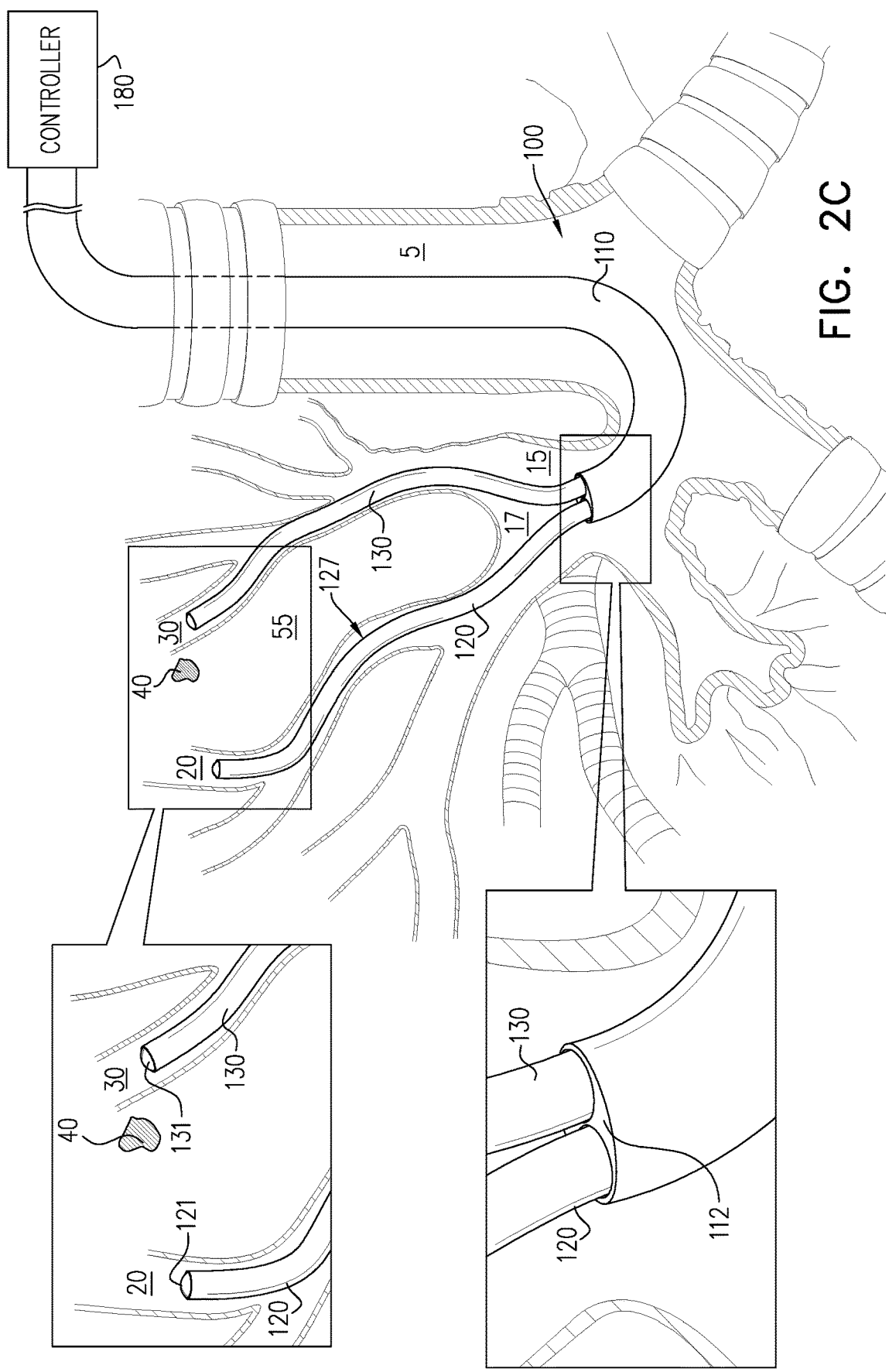

As is shown in FIGS. 2B and 2C, first tube 120 and second tube 130 are then advanced (e.g. independently of each other) through the airways to the first site and the second site, respectively—e.g. are advanced out of sheath 110. In FIG. 5, this is represented by step 420. First tube 120 and second tube 130 are advanced along separate routes 127 and 137—e.g. bifurcating from sheath 110 and/or branching away from each other as they progress deeper into lung 55, e.g., into higher-generation, smaller airways, such that distal end 126 of first tube 120 become disposed at a first site 20 and second tube becomes disposed at a different, second site 30. First site 20 may thus be referred to as an imaging site, and second site 30 may be referred to as a tool site. The two sites are typically situated in different bronchi or bronchioles with respect to each other. It is possible that first site 20 and second site 30 are located in airways that converge toward target 40. It is to be noted that, although imaging site 20 may be defined as the site at which advancement of first tube 120 ceases (i.e. the end of route 127), ultrasound transceiver 128 may be extended through (e.g. beyond) the imaging site—e.g. further distally along the first airway. Similarly, although tool site 30 may be defined as the site at which advancement of second tube 130 ceases (i.e. the end of route 137), tool 138 may be extended through (e.g. beyond) the tool site—e.g. further distally along the second airway and/or into the surrounding tissue toward target 40.

Tubes 120 and 130 may be advanced simultaneously, or in any order (including a stepwise alternating sequence), towards their respective sites 20 and 30. For example, the end of the first tube may become disposed in a first sixth-generation bronchus, and the end of the second tube may become disposed in a different sixth-generation bronchus. That is, the imaging site may be situated, along the first route, at the same bronchus-generational depth (e.g., seventh generation) as is the tool site, along the second route. Alternatively, the first tube may be advanced to a different generation-depth than the second tube, for example the first tube may be advanced only to a fourth-generation bronchus, with the second tube advanced to a seventh-generation bronchus. That is, the imaging site may be situated, along the first route, at a different bronchus-generational depth than is the tool site, along the second route.

Advancement of the sheath may be terminated at a location in the airways that has been predetermined to be appropriate for advancement of both the first and second tubes—e.g. a location that is common to the first and second routes. (Such determination is described in more detail hereinbelow.) For example, advancement of the sheath may be terminated at or just before a fork 17 at which routes 127 and 137 diverge, or within a bronchus 15 that is common to both of the routes. The predetermined extent of sheath 110 advancement may also be determined by limitations specific to each subject, such as a diameter of a bronchus capable of receiving the sheath, which necessarily has a diameter greater than tubes 120, 130.

It is to be noted that, although routes 127 and 137 typically diverge from each other at some point (e.g. at some fork) within the airways, they may subsequently converge as they approach the target. That is, a distal part of first route 127 may converge with a distal part of second route 137.

In some applications, and as shown (e.g., in FIGS. 2B-C), first tube 120 and second tube 130 are guided towards their respective sites using cameras 121 and 131 disposed at their respective distal ends 126 and 136, to provide an operator with a view of the airways. This is represented by steps 420a' and 420a" of FIG. 6, which may be considered variants of step 420 of FIG. 5. In some such applications, these cameras 121 and 131 are additionally used to guide the passage of sheath 110 down the trachea 5 and into the bronchus 15, e.g. with the tubes 120 and 130 disposed within the sheath and the cameras disposed at the distal ends 126 and 136 of the tubes. This is shown in FIG. 2A, and is represented by optional step 410a of FIG. 6, which may be considered to be a variant of optional step 410 of FIG. 5. It is hypothesized that such an approach may advantageously provide stereoscopic vision and its associated advantages, such as redundancy and/or depth information (e.g. by generating disparity maps from the images provided by the two cameras), during advancement of sheath 110.

Figure 2D:
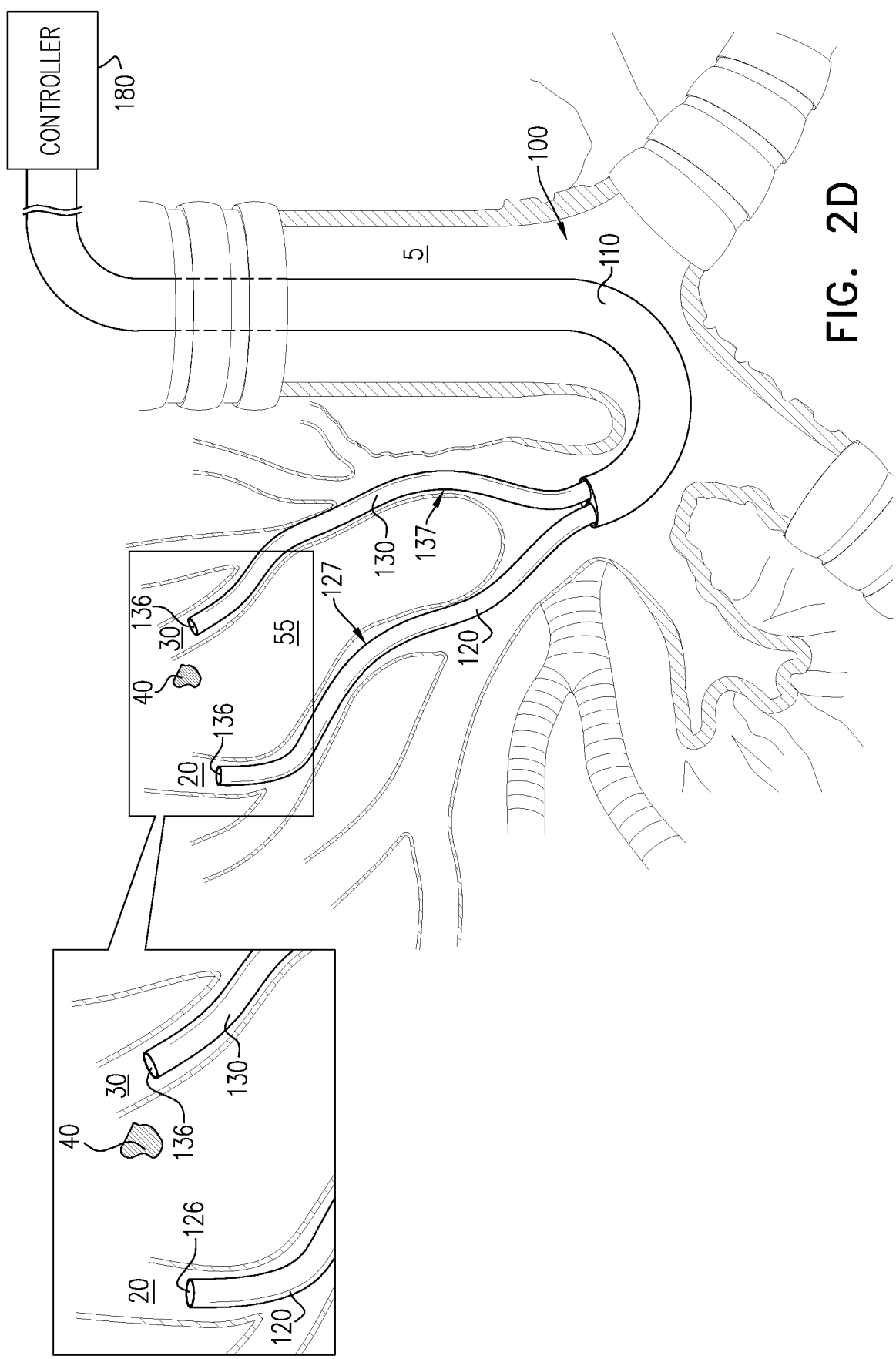

In an application in which cameras 121 and 131 are used to direct tubes 120 and 130 towards their respective sites 20 and 30, once the tubes are positioned at their respective sites, the cameras may be withdrawn through the tubes and out of the subject (FIG. 2D, and steps 422', 422" of FIG. 6). In some applications, and as shown in FIG. 2E, at this point ultrasound transceiver 128 is passed through the first tube and out of the first tube's distal end 126 (step 424' of FIG. 6), and medical tool 138 is passed through the second tube, and out of the second tube's distal end 136 (step 424" of FIG. 6). It should be noted, as indicated by box 402 in FIG. 6, that any/all of steps 420a', 422', and 424' can be performed in parallel, prior to, or subsequently to any/all of steps 420a", 422", and 424". This is represented in FIG. 6 by steps 420a', 420a", 422', 422", 424', and 424" being bordered by a box 402, which may be considered to be a process by which the tubes, the imaging device, and the tool are positioned appropriately to begin the procedure—the procedure itself being represented by step 440.

Alternatively, one or both cameras may remain at the distal end of the tubes, and an ultrasound transceiver may be delivered through a working channel (not shown) of the first tube and out of its distal end, and/or a medical tool may similarly be delivered through a working channel (not shown) of the second tube and out of its distal end.

In some applications, the first tube is advanced to the imaging site 20 with ultrasound transceiver 128 already disposed at its distal end, and the second tube is advanced to the tool site 30 with medical tool 138 already at its distal end. In some such applications, tubes 120 and 130 may be elongate members that do not have an open lumen.

For some applications, once tubes 120 and 130 are positioned at their respective sites (FIG. 2E), the position of the imaging device beyond distal end 126 of tube 120, and/or the position of the tool beyond distal end 136 of tube 130, may require adjustment, as represented by optional step 430 in FIGS. 5 and 6—e.g. without further advancement, retraction and/or steering of the tubes. FIG. 7 is a flowchart expanding on certain details of optional position refinement step 430, in accordance with some applications, and as further described in FIGS. 14A-E.

The operator may use real-time imaging provided by ultrasound transceiver 128 to facilitate this reposition refinement. For example, once ultrasound transceiver 128 is at imaging site 20 and/or at distal end 126 of tube 120, imaging using the ultrasound transceiver may be commenced—e.g. the ultrasound transceiver may be activated (step 432). Imaging may be commenced prior to arrival of tool 138 at tool site 30 and/or at distal end 136 of tube 130, or may be commenced only once the tool has arrived.

Once imaging has commenced, the operator may determine whether target 40 and/or medical tool 138 are satisfactorily in the field of view of the ultrasound transceiver (decision 434). If target 40 and/or medical tool 138 are not adequately positioned in the field of view of ultrasound transceiver 128, the position of the ultrasound transceiver and/or the medical tool may be adjusted by manipulating the appropriate tube and/or rod (step 436). As shown, this may be an iterative process.

In some applications, an electromagnetic signal may be driven through tool 138 in order to assist this process—e.g. to indicate to the operator an appropriate direction in which to move the ultrasound transceiver and/or the tool in order to bring the tool into the field of view. Such electromagnetic assistance is described in more detail with respect to FIG. 14A-E.

Once it has been determined that the target and/or the tool are within the field of view, the operator may proceed to perform the procedure, facilitated by continued imaging (step 440).

Figure 2F:
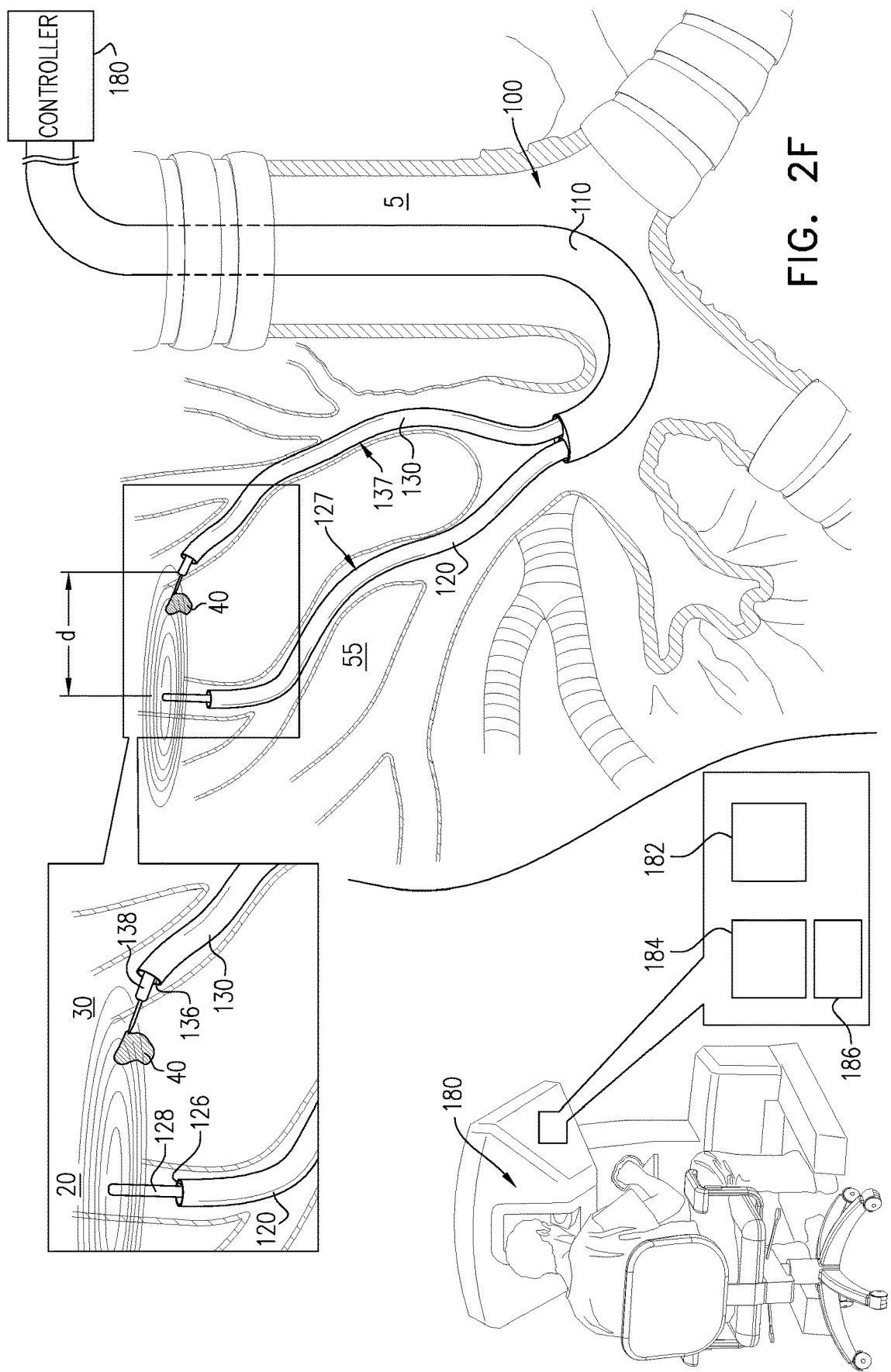

As shown in FIG. 2F, once the operator determines that medical tool 138 is positioned satisfactorily with respect to ultrasound transceiver 128 and target 40, the procedure is carried out, guided by the imaging that is provided by the ultrasound transceiver viewing the tool interacting with the target (step 440 of FIGS. 5-7). Imaging and tool sites 20 and 30 and/or routes 127 and 137 thereto are typically pre-procedurally designated so that, during the procedure, target 40 and medical tool 138 are in the field of view of ultrasound transceiver 128 (e.g. to view the tool interacting with the target). For example, imaging site 20 and tool site 30 may be chosen such that target 40 becomes disposed between ultrasound transceiver 128 and medical tool 138—e.g. with the ultrasound transceiver "looking back" or "looking over" at the target and the medical tool. Alternatively, the medical tool may be closer than the target to the ultrasound transceiver—e.g. with the target behind the medical tool, from the perspective of the ultrasound transceiver.

In some applications, subsequently to positioning the ultrasound transceiver 128 and medical tool 138 at their respective sites 20 and 30 (e.g. subsequently to performing at least some of the procedure with the medical tool at site 30), the positions of the ultrasound transceiver and the medical tool are switched. This is typically achieved by the ultrasound transceiver and the medical tool being withdrawn from their respective tubes 120 and 130, and one or both of the ultrasound transceiver and the medical tool being advanced through the other tube—e.g. such that medical tool 138 becomes positioned at site 20 and/or ultrasound transceiver 128 becomes positioned at site 30. It is hypothesized that this may advantageously provide ultrasound transceiver 128 and/or medical tool 138 with access to target 40 from a different/additional angle of approach. For example, such a technique may be utilized when performing a biopsy on a target to collect a more representative sample of the target. Similarly, such a technique may be used in other procedures, e.g., to release a far side of the target when removing the target from the lung, or to ablate the far side of the target tissue.

Figure 4:
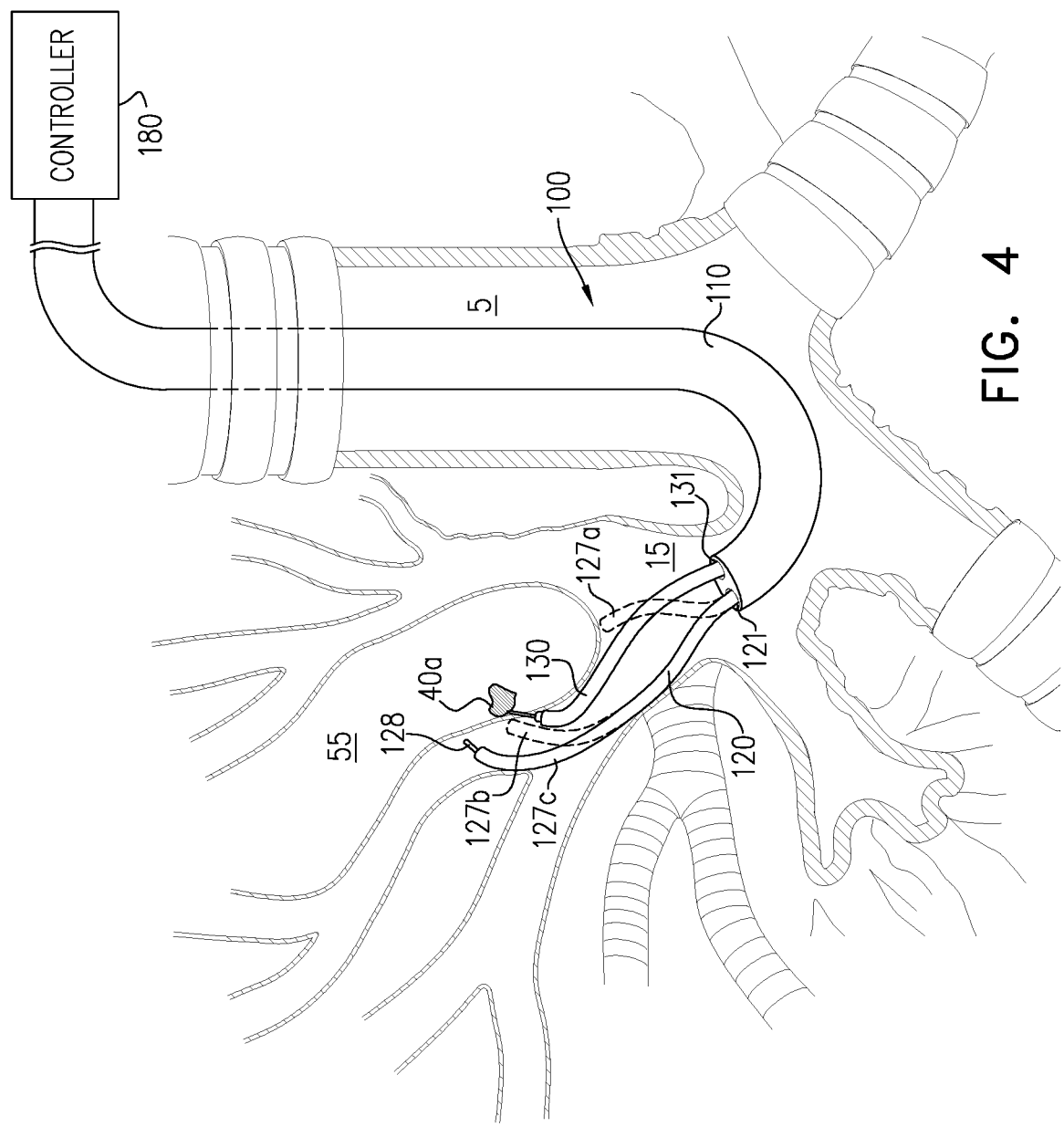
FIG. 4 is a schematic illustration of an alternative technique for use with the system of FIGS. 1 and 2A-F, in accordance with some applications.

Reference is additionally made to FIG. 4. For some applications, in order to image the target from more than a single position during the procedure (e.g. from more than just imaging site 20), a series of imaging sites may be planned for the ultrasound transceiver. In some such applications, e.g., as shown in FIG. 4, building the map may comprise designating multiple imaging sites and/or imaging routes for ultrasound transceiver 128.

For example, routes 127a, 127b, and 127c of FIG. 4 show the ultrasound transceiver acquiring different perspectives of the target during the procedure. For some such applications, a single imaging route may be designated that includes a series of imaging sites that the transceiver will visit sequentially. In some such applications, each imaging site of the series may be designated by assessing its suitability (including its compatibility with the tool site)—e.g. by assigning a suitability score to that imaging site/tool site pair. Multiple tool sites (e.g. a series of tool sites) may similarly be planned for medical tool 138.

FIG. 4 also illustrates that both the imaging site and the tool site may be situated in the same airway (e.g. in the same bronchus, or both within the trachea), such that the first route and the second route both terminate within the same bronchus or within the trachea. In the illustrated example, the target is assigned reference numeral 40a. It is noted that, while FIG. 4 shows multiple imaging sites and a tool site in the same airway, having multiple imaging sites is independent of having both imaging site and tool site in the same airway. System 100 allows an operator to reposition ultrasound transceiver 128 with respect to target 40a and tool 138 in order to attain a satisfactory field of view of tool 138 interacting with the target—e.g. responsively to the imaging that has been acquired. FIG. 4 shows first tube 120 having been first positioned along a route 127a, then along a route 127b, before finally being positioned along route 127c that the operator has determined results in a satisfactory positioning of ultrasound transceiver 128.

Reference is additionally made to FIGS. 8-12, which show exemplary processes, algorithms, and data-processing systems which may be used in some applications of the present disclosure to carry out various steps of methods described and illustrated in FIGS. 1-4 and diagrammed in FIGS. 5-7.

The pre-procedure designation of sites 20 and 30 and/or target 40 and/or routes 127 and 137 may be performed manually—e.g. by a physician or operator. However, the designation (e.g. route planning) is typically facilitated and/or processed at least in part by a computer (e.g. by a data-processing system running a computer program that includes appropriate instructions), as further illustrated and described hereinbelow.

Figure 8:
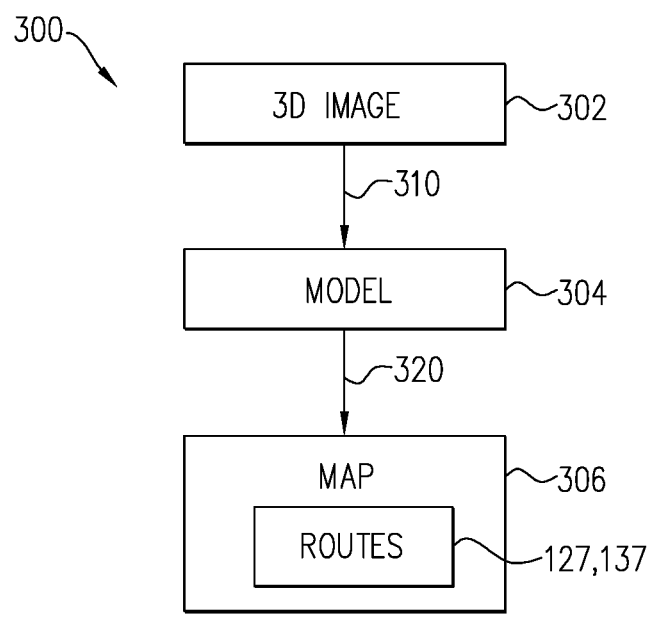
FIGS. 8-12 are schematics of exemplary techniques, modules, and data-processing systems for facilitating a bronchoscopic procedure on a lung of a subject, in accordance with some applications.

In accordance with some applications, FIG. 8 illustrates a computer-implemented technique 300 (e.g. a program, or a collection of programs) for pre-procedural designation of sites 20 and 30 and/or target 40 and/or routes 127 and 137. Technique 300 comprises: (a) a step 310 in which a computer model 304 of the airways of a lung of a subject is generated from a 3D image 302 (e.g. a preoperative image set arranged into a 3D representation) of the lung; and (b) a step 320 in which model 304 is utilized in building a map 306. Map 306 may include imaging route 127, tool route 137, and/or the target. The planning of the routes may be part of step 320. Examples of planning of the routes are described hereinbelow with respect to FIGS. 10-12.

Image 302 may comprise x-ray (e.g. CT) data, MRI data, ultrasound data, and/or data from any other imaging modus. For example, image 302 may be a 3D CT image, a 3D MRI image, etc. Image 302 may be composed of a set of two-dimensional images. In addition to pre-operative imaging data, other inputs may be used for generating the computer model, as further described hereinbelow.

Although steps 310 and 320 are described as being components of the same computer-implemented technique (i.e. technique 300), it is to be noted that step 310 may be performed separately from step 320—e.g. at a different time (e.g. days, weeks, or months in advance of step 320), by a different data-processing system (e.g. on a different computer), and/or in a different location. For some applications, the computer-implemented designation of the sites and/or the routes is performed by activating/running a module 182. Module 182 may be, or may be run by, a data processing system (or a part thereof). In FIGS. 2E-F, module 182 is schematically shown as being a component of and/or controlled by controller 180 (e.g. by a data-processing system thereof). However, it is to be understood that module 182 may be separate from controller 180. For example, module 182 may be provided as a computer program and/or may be run on a computer that is distinct from controller 180—e.g. in a separate location. The designation of sites 20, 30 and routes 127, 137 may be facilitated by computer model 304.

As described above, computer model 304 may comprise a representation of the airways and may also comprise an indication or representation of the location of a target, the target being the lesion, tissue, or site toward which the planned bronchoscopic procedure is directed. The representation of the airways may be generated from the 3D image. The representation of the airways is typically incorporated into computer model 304 (or the computer model is composed based upon the representation of the airways) by computer processing of the initial imaging data.

Figure 10:
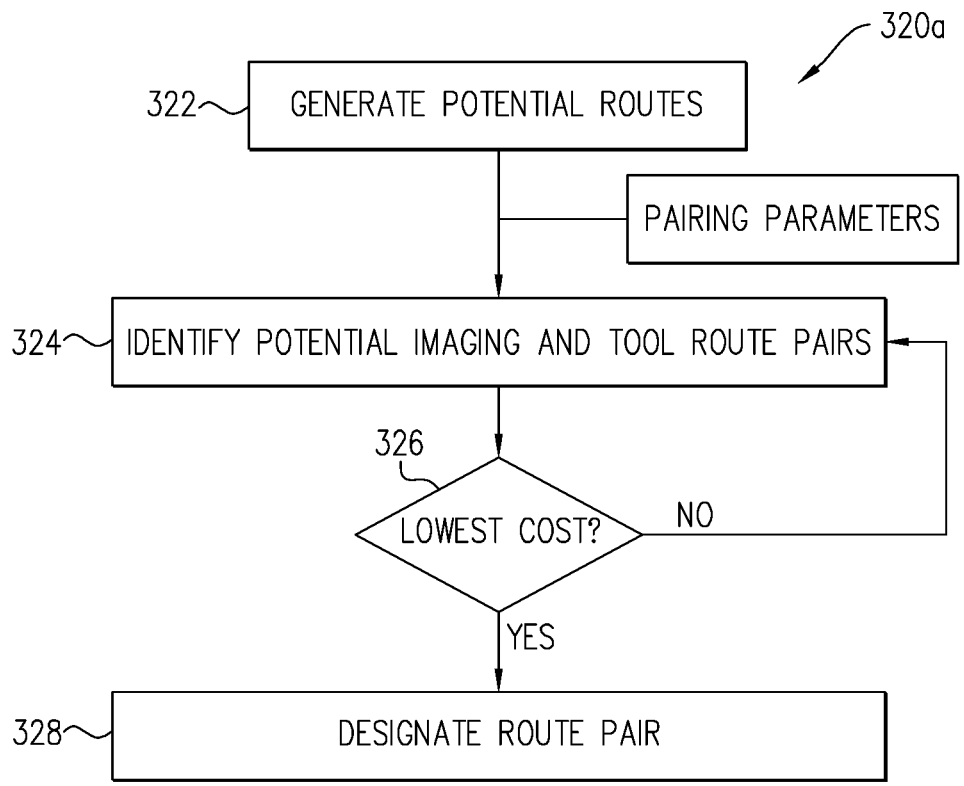
Figure 11:
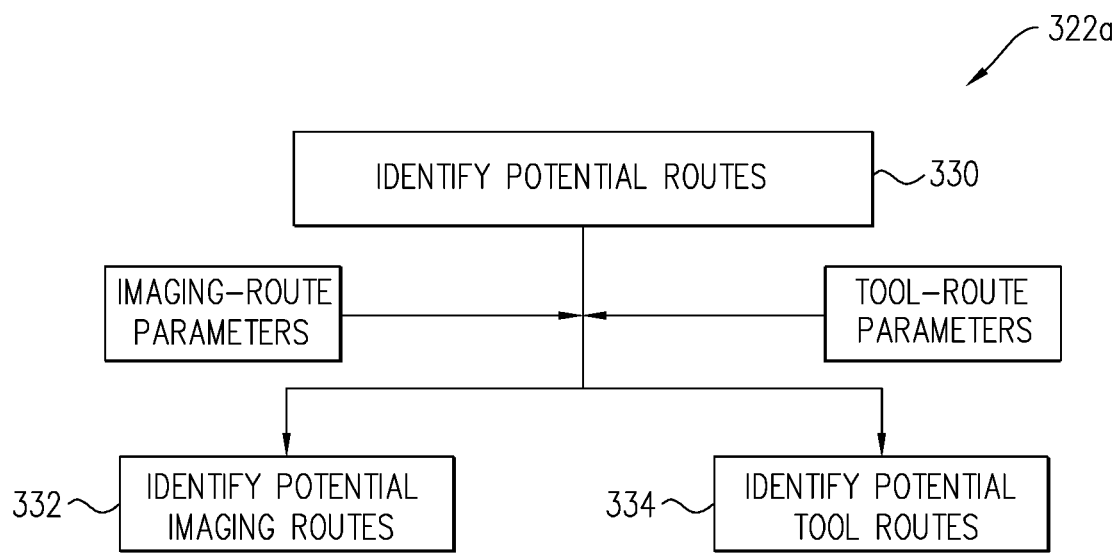
Figure 12:
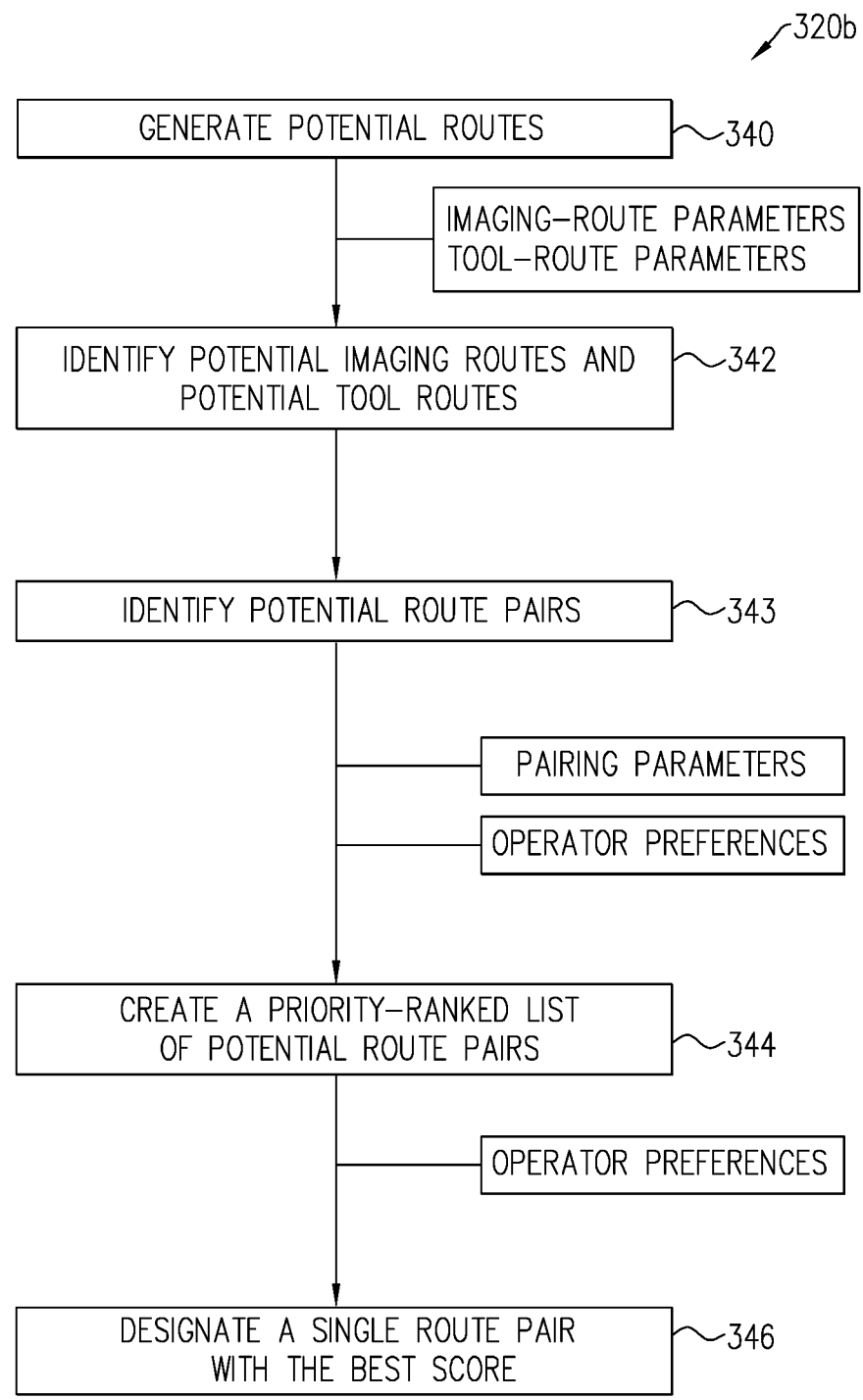

In some applications, map 306 comprises a vector representation of the airways, which may then be used to generate imaging route 127 and tool route 137—e.g. as further described in FIGS. 10-12. In some applications model-generating step (or program) 320 generates the routes directly from model 304—e.g. without utilizing a vector representation of the airways as an intermediary.

In some applications, as described above, imaging site 20 and tool site 30 may be designated on the airway representation (e.g., on the computer model or on the map) prior to generating imaging route 127 and tool route 137. That is, imaging site 20 and tool site 30 may be used as inputs for generating the routes. In some applications, imaging and tool sites 20, 30 are generated as part of the route planning process.

For some applications, the representation of target 40 is incorporated into the computer model by computer processing of the 3D image. For example, the computer processing of the 3D image may recognize target 40 and responsively (e.g. automatically) define the representation of the target within the model. For some application, the representation of the target site may be incorporated into the computer model by a user (e.g., a physician or an operator) identifying the target site—e.g., as described in more detail hereinbelow. In some such applications, the user may demarcate the boundaries of the target within the computer model, such as by defining the boundaries of the target, or marking a surface area of the target. For some applications, the representation of target 40 is refined by the user after the computer processing has provided a preliminary identification of the target—e.g. the user may select the representation of the target from a selection of proposed potential targets, and/or may refine the boundaries of a target.

Figure 9:
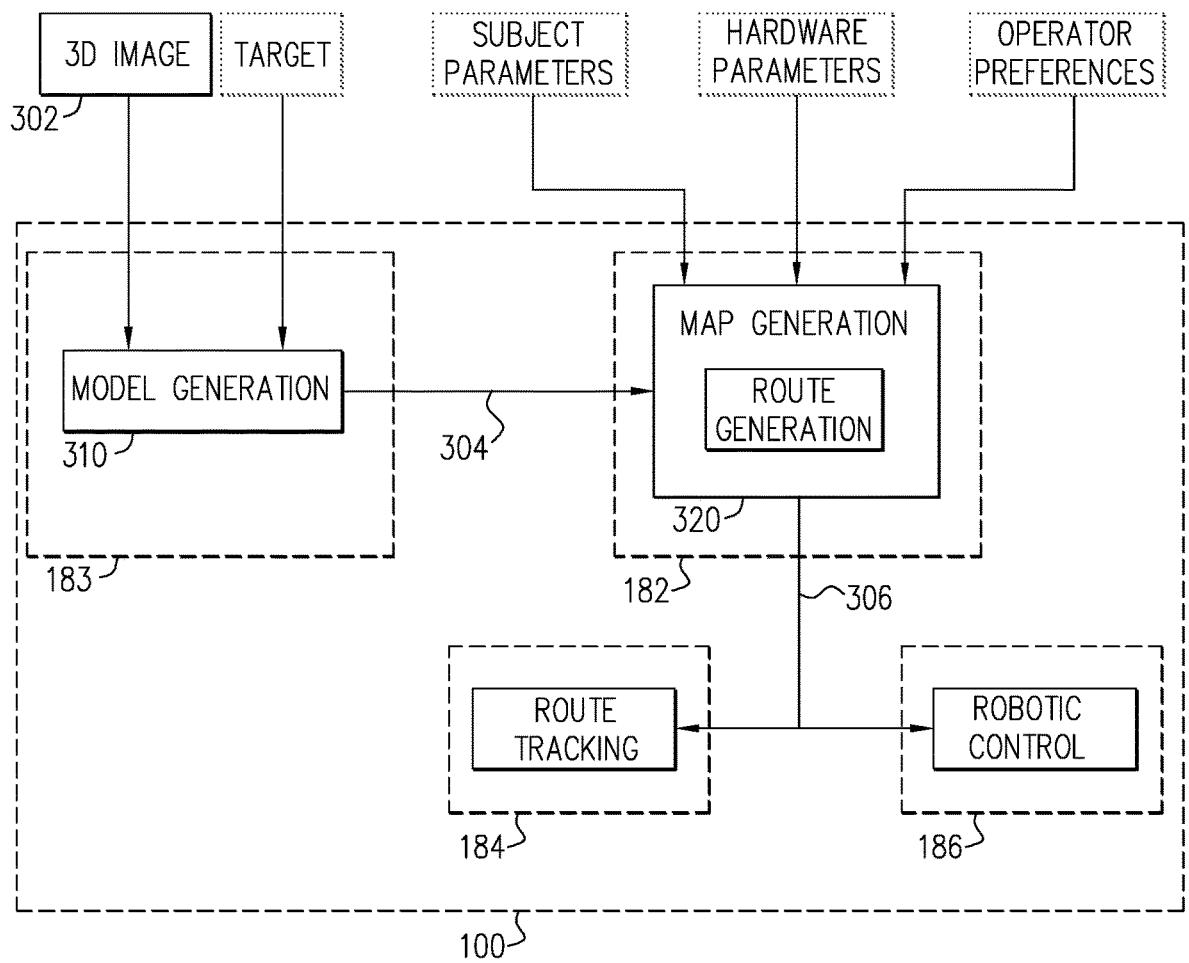

FIG. 9 is a schematic representation of an implementation in which system 100 is configured to perform, inter alia, steps of technique 300, in accordance with some applications.

As described hereinabove, a model-generation step (or program) 310 generates model 304. Step 310 may be performed by a module 183—e.g. a model-generation module. Model-generation step 310 utilizes inputs specific to a particular subject and/or a particular procedure. As described hereinabove, one such input is 3D image 302. As described elsewhere herein, other such inputs may include data indicative of the target—e.g. inputted by a physician. In some applications, the target data may be a direct input of map generation step (or program) 320 (e.g. the data may be inputted into module 182 rather than into module 183).

As noted hereinabove, computer model 304 includes a representation of the airways, and typically also includes the target mapped onto the airway representation.

A map-generation step (or program) 320 generates map 306, and includes a route-generation step (or program) that generates routes 127 and 137—e.g. as further described with reference to FIGS. 10-12. Step 320 may be performed by module 182, described elsewhere herein. Map-generation step 320 utilizes model 304 as an input. For example, step 310 (e.g. module 183 performing step 310) may feed model 304 to step 320 (e.g. to module 182), and/or step 320 (e.g. module 182) may obtain or reference model 304 from step 310 (e.g. from module 183). Thus, model 304 is illustrated in FIG. 9 as an arrow from model-generation step 310 to map-generation step 320. As detailed elsewhere hereinbelow, other inputs to map-generation step 320 (e.g. to module 182) may be provided. Some non-limiting examples of such inputs shown in FIG. 9 are "subject parameters", "hardware parameters", and "operator preferences".

System 100 may comprise a route-tracking module 184 (also shown in FIGS. 2E-F) configured to determine, and/or provide to the operator an indication of, whether route(s) 127/137 are being followed as planned, whether site(s) 20/30 have been reached, and/or whether adjustments are required. Module 184 is described in more detail hereinbelow.

System 100 may comprise a robotic-control module 186 (also shown in FIGS. 2E-F), which may be a component of a robotic controller. Robotic-control module 186 is used to advance sheath 110 and/or tubes 120 and 130 towards their respective sites, and/or to manipulate (e.g. steer) the tubes at their respective sites. This may be achieved by the robotic controller (e.g. robotic-control module 186) controlling a robotic manipulator to which it is electronically and/or mechanically connected. Module 186 is described in more detail hereinbelow.

As shown in FIG. 9, map 306 (typically including a pair of imaging and tool routes), is utilized by modules 184 and 186—e.g. to facilitate performance of steps 420*a*' and 420*a*" of FIG. 6. For example, step 320 (e.g. module 182 performing step 320) may feed map 306 (e.g. the routes therein) to modules 184 and 186; and/or one or both of modules 184 and 186 may obtain or reference map 306 from step 320 (e.g. from module 182).

Modules 184 and 186 may run simultaneously with each other, and/or may communicate with each other in real-time or near-real-time in order to achieve guided advancement of tubes 120 and 130. For example, and as shown in FIGS. 2E-F, modules 184 and 186 may be components of controller 180.

Each (e.g. any, or all) of modules 182, 183, 184, and 186 may be a component of system 100. For each of modules 182, 183, 184, and 186 that is a component of system 100, the module may or may not be a component of controller 180.

In some applications, model generation step 310 may be performed by a component of system 100 other than controller 180. That is, module 183 may not be a component of controller 180. Instead, an independent data-processing system or program may be utilized. In some applications, module 183 may be used separately (e.g. at a separate time and/or in a different location) from controller 180. For example, model-generation step 310 may be performed pre-procedurally—e.g. in advance of the subject being admitted to the medical facility for the procedure, either as part of system 100 or as an independent module for use with system 100.

In some applications, route generation step 320 may be performed by a component of system 100 other than controller 180. That is, module 182 may not be a component of controller 180. Instead, an independent data-processing system or program may be utilized. In some applications, module 182 may be used separately (e.g. at a separate time and/or in a different location) from controller 180 and/or from module 183. For example, route-generation step 320 may be performed pre-procedurally—e.g. in advance of the subject being admitted to the medical facility for the procedure, either as part of system 100 or as an independent module for use with system 100.

In some applications, modules 184 and 186 are components of controller 180. In some applications, module 186 is a separate unit that may be configured to be operated by controller 180 and/or system 100.

For some applications, system 100 may provide for the user to input a preferable angle of approach with respect to the target—for the first tube and/or for the second tube. For example, a physician may determine that a particular angle of approach for ultrasound transceiver will be advantageous for imaging, and/or that a particular angle of approach for tool 138 will be advantageous for sampling and/or treating target 40 and/or a particular portion thereof. Furthermore, the operator may select a tolerance—e.g., such that a range of angles of approach, within the tolerance, is acceptable. These, and/or other factors or parameters such as those detailed in the following paragraphs, may be utilized by module 182 as inputs for generating map 306 (e.g. for determining routes 127 and 137).

A non-exhaustive list of such parameters, which may be manually inputted, or may be derived from and/or calculated using the computer model, comprises:

(i) An anticipated field of view of transceiver 128 (e.g. whether target 40 and/or medical tool 138 is anticipated to appear in the field of view).
(ii) A proximity of a potential imaging site to a potential tool site.
(iii) A proximity of a potential tool site to target 40.
(iv) The presence of structures in the lung (e.g. large blood vessels), between a potential imaging site and a potential tool site, that may obstruct the field of view of transceiver 128.
(v) Ease of access to a potential imaging site (i.e. ease of navigation of first tube 120 to the potential imaging site), such as airway geometry (e.g. diameters and branching angles).
(vi) Ease of access to a potential tool site (i.e. ease of navigation of second tube 130 to the tool site) such as airway geometry (e.g. diameters and branching angles).
(vii) A predicted orientation of the ultrasound transceiver at a potential imaging site—e.g. a predicted "natural" orientation of the ultrasound transceiver upon arrival at the potential imaging site, and/or a predicted ability to, at the potential imaging site, reorient the transceiver to obtain a desired field of view.
(viii) A predicted orientation of the medical tool at a potential tool site—e.g. a predicted "natural" orientation of the tool upon arrival at the potential tool site, and/or a predicted ability to, at the potential tool site, reorient the tool to obtain a desired position with respect to target 40.
(ix) Accessibility of the medical tool to the target from a potential tool site.
(x) A distance between (1) a potential sheath-termination site and (2) (a) a potential imaging site and/or (b) a potential tool site. Typically, this is a distance between a distal-most airway that is common to both a potential first route and a potential second route. For example, with reference to the example shown in FIG. 2C, this may be the distance between (1) bronchus 15 and (2) (a) site 20 and/or (b) site 30. For some applications, this "distance" may be a straightforward distance along the airway(s). Alternatively or additionally, this "distance" may be a generational-distance, meaning a difference between (1) the generational depth of the potential sheath-termination site, and (2) (a) the generational depth of the potential imaging site and/or (b) the generational depth of the potential tool site. For example, the generational-distance between bronchus 15 and site 20 may be 3 (i.e. tube 120 passes 3 forks on its route from bronchus 15 to site 20).
(xi) A predicted angle of approach to target 40 from a potential imaging site 20 or tool site 30—e.g. its correspondence to a user-inputted preferable angle of approach. For example, a potential site may be assessed by determining possible angles of approach to the target.
(xii) The dimensions of the target, e.g., as defined in the medical imaging set, or as determined by a medical professional. In some applications, more than one target may be designated.
(xiii) Individual characteristics of the subject: e.g., body-mass index, smoking history, height, weight, gender, age, and past medical history including comorbidities.
(xiv) Size, shape, model, and/or bendability (e.g. dependent on factors such as flexibility, radius of curvature, material composition, diameter and thickness) of the tubes.

(xv) Size, shape, model, viewing frustum, and other details of the imaging devices (cameras, ultrasound).
(xvi) Tool parameters: material composition; specific dimensions, e.g., width; flexibility; and type of tool.
(xvii) Maximal allowable route length, route tortuousness, and/or route branches.

For some applications, the designation of the sites and/or routes, and/or the derivation and/or calculation of the above parameters may take into account one or more characteristics of system 100—e.g. of ultrasound transceiver 128 and/or medical tool 138. Nonlimiting examples of such characteristics include the field of view of ultrasound transceiver 128, the effective operating range of the medical tool from the end of second tube 130, the effective imaging range of the ultrasound transceiver (marked as "d" in FIGS. 2E and 2F), the manipulability (e.g. deflectability and/or rotatability) of each of the ultrasound transceiver and the tool at the end of its respective tube (e.g. via respective rod 125 and 135).

To facilitate building the computer model, a map of the airways, and/or potential routes, the input data may be divided into non-exclusive and potentially overlapping groups of parameters, e.g., as shown in FIGS. 10-12:
 a) pairing parameters—(ii), (iv), (x), (xii), (xiv), (xvii);
 b) imaging-route parameters—(i), (v), (vii), (xi), (xv); and
 c) tool-route parameters—(iii), (vi), (viii), (ix), (xi), (xvi).

In some applications, the parameters may also or alternatively be divided into other potentially overlapping groups, e.g., as shown in FIGS. 9, e.g., those relating to:
 a) the preoperative imaging set, e.g., CT/MRI, of the lung of the subject—(iv), (v), (vi), (x);
 b) the target within the lung—(ii), (iii), (v), (vi), (ix), (xii)
 c) subject parameters related to the individual undergoing the procedure—(xiii);
 d) hardware parameters relating to, e.g., the controller, the ultrasound, and the tool—(i), (v), (vii), (viii), (ix), (xiv), (xv), (xvi);
 e) operator preferences—(i), (v), (vi), (x), (xi), (xvii).

FIG. 10 is a schematic diagram of an exemplary route-planning program 320a, which may be considered to be a variant of step/program 320, in accordance with some applications. In step 322, potential routes along the airways to the target are generated by program 320a. This may be performed by referencing model 304 directly, or by first generating map 306 (e.g. a vector-based map) and then referencing the map. In step 324, pairing parameters (described elsewhere herein) are used to identify, from the potential routes generated in step 322, potential pairs of routes for the imaging device (e.g. ultrasound transceiver 128) and the tool (e.g. tool 138). Some of the potential routes may fit the criteria for both imaging routes and tool routes e.g. such that one potential pair may include a given potential route as an imaging route while another potential pair may include the same potential route as a tool route.

In decision 326, the potential pairs are analyzed (e.g. using a cost function) to determine the cost of each potential route pair. Because there may exist a trade-off between optimizing the position of ultrasound transceiver 128 and optimizing the position of medical tool 138, analysis may be used to determine an optimal route pair from a selection of satisfactory pairs. For example, the cost function in this program may take into account total route length, number of turns, angles of turning, maneuverability, and proximity of one route to the other through adjacent airways.

In step 328, an optimal route pair (e.g. the route pair with the lowest cost) is designated. It is to be understood that optimizing the tool route may necessitate a less-optimal imaging route, or vice versa. Preferentially favoring optimization of the imaging route over optimization of the tool route, or vice versa, may be made by the operator on a case-by-case basis (e.g. by module 182 providing an adjustable preference weighting), or may be made by the program considering, e.g., subject parameters. Program 320a may be performed by module 182 or a variant thereof.

In some applications, module 182 may use algorithms and/or computer processing to provide a human operator with a selection of potential pairs, from which the operator can select a desired pair. In some applications, module 182 may provide a human operator (e.g. a physician) with the possibility of adjusting the weighting of certain of the parameters, such that the operator can give more weight to one parameter over another parameter. For some such applications, this may be considered biasing of the site/route determination algorithm. For example, the operator may be provided with the possibility to adjust a trade-off between visibility and accessibility—e.g., to allow the algorithm to select a less-optimal tool route in exchange for more-optimal imaging. For example, such a trade-off-adjustment feature may be provided e.g., as a slider on a user interface-, to emphasize the nature of this adjustment as a trade-off.

FIG. 11 is a schematic diagram of an exemplary route-generation program 322a, which may be considered to be a variant or subroutine of step 322 of step/program 320a, in accordance with some applications. In step 330, potential routes (e.g. all potential routes) to the target are identified. In step 332, from the potential routes, potential imaging routes are identified (e.g. a list of potential imaging routes is generated) by applying imaging-route parameters (described hereinabove) to all potential routes. In step 334, from the potential routes, potential imaging routes are identified (e.g. a list of potential tool routes is generated) by applying tool-route parameters (described hereinabove) to all potential routes. While the parameters to be considered for each route may be similar, the acceptable values and/or weightings for the imaging route vs. the tool route may differ. It is possible that one potential route may be identified as both a potential imaging route and as a potential tool route. Program 322a may be performed by module 182 or a variant thereof.

FIG. 12 is a schematic diagram of an exemplary route-planning program 320b, which may be considered to be a variant of step/program 320, in accordance with some applications. The sequence of steps shown may be used in combination with those described with reference to FIGS. 10 and/or 11, and/or with the hardware/modules/programs described with reference to FIG. 9, and/or as an alternate implementation of the disclosed methods. In some applications, the steps may be re-ordered, some steps may be omitted, or other steps added. A list of potential routes is generated (step 340). Utilizing the imaging-route parameters and tool-route parameters, potential imaging routes and potential tool routes are identified (step 342). From the potential imaging routes and potential tool routes, potential route pairs (i.e. compatible pairs of imaging routes and tool routes) are identified (step 343). The pairs of routes are then analyzed to create a priority-ranked list of route pairs. The priority-ranked list may be based on, for example the pairing parameters listed above, and/or inputted operator preferences e.g. regarding prioritization and/or weighting of particular parameters over others (step 344). The final output of program 320b is the designation of a single route pair having the best score (step 346). Designation of this route pair may be responsive to further inputting of operator preferences. For example, one or more potential route pairs (e.g. in the form of the priority-ranked list) may be displayed, along with an interface that prompts for and/or facilitates inputting and/or adjustment of parameters or preferences. For example, a weighting interface may allow the operator to input and/or adjust the weighting of a given factor, and/or prioritization of one factor over another. Examples of such prioritization include prioritization: between route length and angle of approach; between imaging parameters and tool parameters, and between optimization of imaging route and optimization of tool route. Program 320*b* may be performed by module 182 or a variant thereof.

It is noted that the steps and components illustrated in FIGS. 8-12 show exemplary applications of the disclosed methods; other applications of the described methods may include additional or alternate specific steps.

In the present disclosure, the term data-processing system may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, group) that executes code; memory (shared, dedicated, or group) that stores code executed by a processor; other suitable hardware components, such as optical, magnetic, or solid state drives, that provide the described functionality; or a combination of some or all of the above, such as in a system-on-chip. The term code, as used above, may include software, firmware, and/or microcode, and may refer to programs, routines, algorithms, functions, classes, and/or objects. The term shared processor encompasses a single processor that executes some or all code from multiple modules. The term group processor encompasses a processor that, in combination with additional circuitry (e.g. processors), executes some or all code from one or more modules. The term shared memory encompasses a single memory that stores some or all code from multiple modules. The term group memory encompasses a memory that, in combination with additional memories, stores some or all code from one or more modules. The term memory may be subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

In some applications, a potential pair comprising a potential imaging site 20 and a potential tool site 30 is proposed by module 182, which then assesses this potential pair in light of the above-described parameters in order to determine a suitability of this potential pair (e.g. the compatibility of the potential imaging site of the pair with the potential tool site of the pair). For example, a potential pair may only be considered suitable if (i) the target and the tool site of the pair are within the effective imaging range of the imaging site, and (ii) both the imaging site and the tool site are accessible by their respective tubes.

In some applications, and as shown in FIGS. 10-12, the above-described determination of suitability is performed by assigning a suitability score to each potential pair. That is, the above-described determination of suitability includes calculating the suitability score. The different parameters may be differentially weighted, such that certain parameters contribute more to the suitability score than others. Once the overall score has been calculated, using the above-mentioned parameters, module 182 may select (and optionally present) at least one pair of sites with a satisfactory score—e.g. with a suitability score that exceeds a predetermined threshold score. For some applications, the data-processing system may select and/or present a single, optimal pair—e.g. the pair that has the highest threshold score of all of the potential pairs that were scored. Artificial intelligence and/or machine learning may be used to determine the optimal pair of sites, by analyzing the different factors, typically using big data to determine the ideal pair.

It is hypothesized that, at least for some applications, for a given potential pair, it may be advantageous to select the potential imaging site based on a previously-selected tool site (as opposed to selecting the potential tool site based on a previously-selected imaging site), e.g. because there may be fewer suitable tool sites than imaging sites within the lung. Therefore, in some applications, the controller first selects a potential tool site 30 for medical tool 138, typically by assessing the compatibility of the potential site for medical tool 138, (e.g. with respect to one or more of the above-mentioned parameters). Once a potential tool site has been selected, the computer model is used to procure a plurality of potential imaging sites for the selected potential tool site, and, using the scoring system described above, to select an appropriate potential imaging site for the selected potential tool site.

In contrast to the above, it is hypothesized that, at least for some applications, for a given potential pair, it may be advantageous to select the potential tool site based on a previously-selected imaging site (as opposed to selecting the potential imaging site based on a previously-selected tool site), e.g. because there may be fewer suitable imaging sites than tool sites within the lung. Therefore, in some applications, the controller first selects a potential imaging site 20 for ultrasound transceiver 128, typically by assessing the compatibility of the potential site for ultrasound transceiver 128, (e.g. with respect to one or more of the above-mentioned parameters). Once a potential imaging site has been selected, the computer model is used to procure a plurality of potential tool sites for the selected potential imaging site, and, using the scoring system described above, to select an appropriate potential tool site for the selected potential imaging site.

In some applications, once a pair of sites 20 and 30 have been proposed, a virtual representation of ultrasound transceiver 128 and/or medical tool 138 at their respective potential sites 20 and 30 may be used to assess the potential pair. For example, when assessing the parameters of a potential imaging site 20, a representation of ultrasound transceiver 128 at a potential imaging site 20 may be provided, in order to give a physician or a computer processor the ability to pre-procedurally determine any of (a) which views of the anatomy (e.g. target 40) are obtainable by the transceiver at the potential imaging site, (b) how the transceiver will be dimensioned with respect to the narrow airways at the potential imaging site, and (c) whether the transceiver will be repositionable at the potential imaging site. A similar virtual representation may be simulated for medical tool 138 at a potential tool site 30.

In some applications, one or more of the parameters described hereinabove (e.g. the accessibility of a potential first route 127 or a potential second route 137) is assessed by using the computer model to pre-procedurally simulate one or both of first tube 120 and second tube 130 being advanced to sites 20 and/or 30 respectively, via the potential route(s). This simulation-facilitated assessment may be performed by the data-processing system—e.g. without human input. Alternatively, the simulation may be presented (e.g. by the data-processing system) as a virtual tour, and the simulation-facilitated assessment is performed by a human operator (e.g. a physician), facilitated by the virtual tour.

For some applications, the above-described techniques may be described as using a computer model of a lung to build a map that includes (i) first route 127 to imaging site 120 within the computer model of the lung, for advancement of ultrasound transceiver 128, and (ii) second route 137 to tool site 30 within the computer model of the lung, for advancement of medical tool 138. Typically, at least one of (i) the imaging site and (ii) the tool site is designated based on an expected field of view of the ultrasound transceiver with respect to the medical tool (e.g. a predicted presence, within the field of view, of the medical tool at the tool site).

In some applications, and as noted hereinabove, extracorporeal controller 180 includes a robotic-control module (e.g. of a robotic controller) 186, used to advance sheath 110 and/or tubes 120 and 130 towards their respective sites, and/or to manipulate (e.g. steer) the tubes at their respective sites. A user may be able to use robotic-control module 186 (e.g. the robotic controller to which the robotic-control module belongs) to control (e.g. actuate) a robotic manipulator, for example using a joystick—e.g. controller 180 may comprise or be connected to a joystick. Alternatively, the robotic manipulator may be at least partly automatically controlled (e.g. actuated) by controller 180, such that at least part of the procedure is executed automatically by controller 180.

For some applications, the above-described computer model 304 of lung 55 may be used by controller 180 to determine the position of tube(s) 120 and 130 within the airways, e.g. by mapping, onto the computer model, real-time positioning data. Such positioning data may include, for example, imaging data generated from ultrasound transceiver(s) 128 and/or camera(s) 121/131 at the end of the tubes, and/or data (e.g. electromechanical data) from sensors on the tubes and/or the robotic manipulator. For example, controller 180 may comprise control circuitry such as a route-tracking module 184 (e.g. a data-processing module and/or a computer program), that, using the positioning data, can identify whether route(s) 127/137 are being followed as planned, whether site(s) 20/30 have been reached, and/or whether adjustments are required. In some such applications, an electromagnetic navigation system may provide this data, by detecting a locator guide(s) on the tube(s), to determine the(ir) position(s) within lung 55.

For some applications in which robotic-control module 186 is used to advance tubes 120 and 130 towards their respective sites 20 and 30, intraprocedural imaging (distinct from that provided by transceiver 128 and/or cameras 121/131) may be utilized, in order to determine or verify the position of the tubes (e.g. the ends of the tubes 126, 136) within lung 55. Such intraprocedural imaging is typically performed using an extracorporeal imaging system, such as a CT system (e.g. cone beam CT) or an MRI system.

For some applications in which such intraprocedural imaging is performed, tubes 120 and 130 may be sufficiently long such that extracorporeal controller 180 can be sufficiently spatially separated from the imaging system. This is hypothesized to be advantageous, for example, for applications in which such intraprocedural imaging is performed using MRI, as it may allow MRI-incompatible components of system 100 (e.g. controller 180 and/or robotic-control module 186) to be situated outside of the vicinity of the imaging—e.g. in a separate room. It is hypothesized that this is particularly advantageous and feasible for applications in which tubes 120 and 130 are robotically controlled.

A further hypothesized advantage provided by robotic control is the potential to allow the operator to temporarily move away during imaging, e.g. to advantageously reduce exposure of the operator to ionizing radiation. For example, the robotic control may allow the operator to temporarily "freeze" a position of the tubes within the lung during the procedure, and then return to the subject while the tubes remain stationary.

Reference is again made to FIGS. 3A-C, which are schematic illustrations of an exemplary system 200, for guiding the advancement of first and second tubes 120 and 130 towards their respective sites 20 and 30, in accordance with some applications. System 200 typically includes all, or at least some of, the elements described with reference to FIGS. 2A-F and 5-12. In some applications, system 200 may include an additional imaging device 250, which may be, e.g., a camera or an ultrasound transceiver (i.e. in addition to ultrasound transceiver 128 or cameras 121 and 131 described hereinabove). Imaging device 250 may be used to guide the advancement of first tube 120 and second tube 130 into lung 55. In some applications, imaging device (ultrasound transceiver) 250 has a longer range than transceiver 128. Thus, transceiver 250 may be referred to as a "longer-range transceiver," while transceiver 128 may be referred to as a "shorter-range transceiver". The longer range of transceiver 250 may be achieved by it using lower frequency ultrasound than shorter-range transceiver 128. In such applications, shorter-range transceiver 128 may generate finer images than longer-range transceiver 250.

Figure 3A:
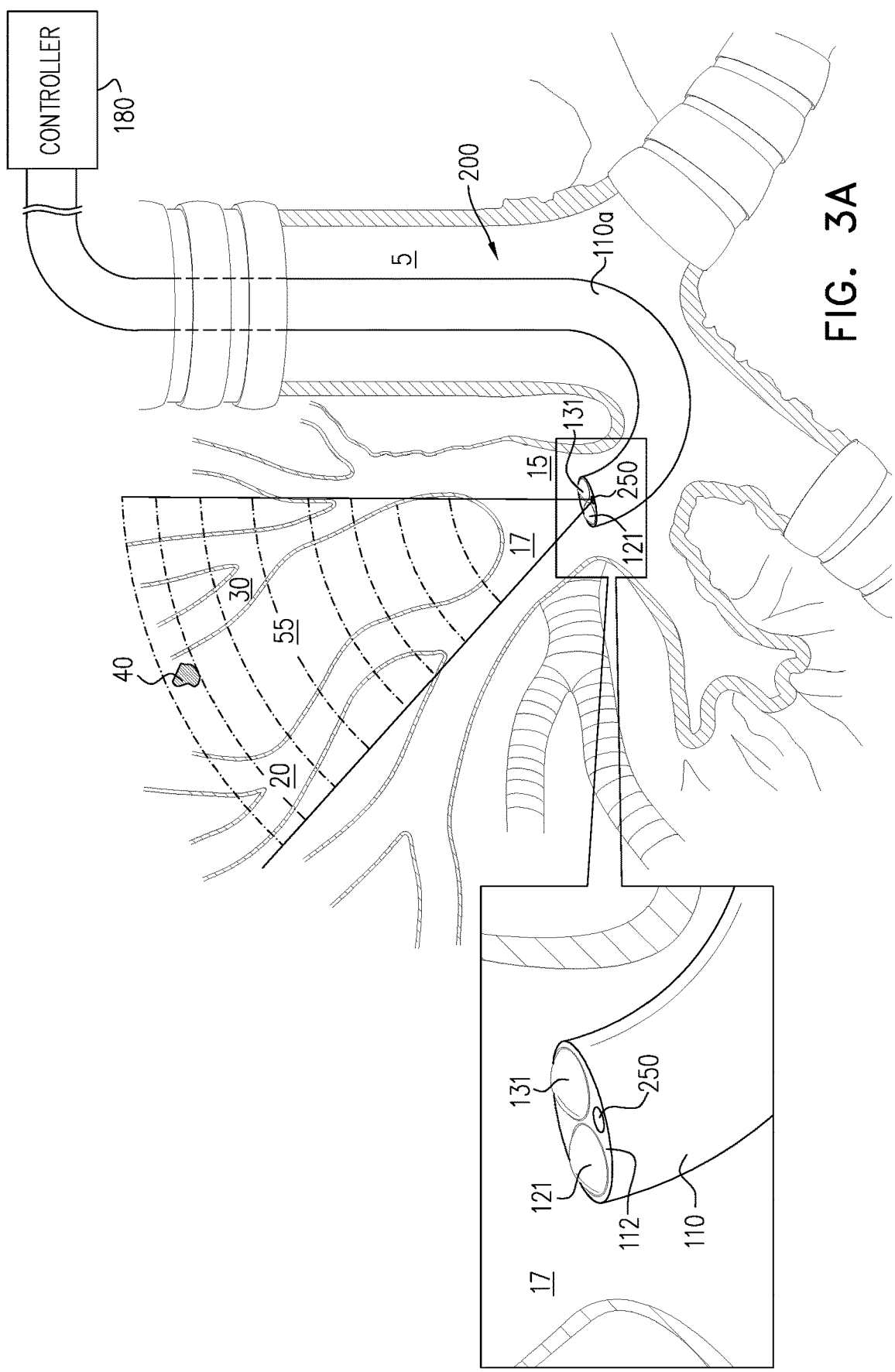
FIGS. 3A-3C are schematic illustrations of an exemplary system for guiding the advancement of a first tube and a second tube into the lung, in accordance with some applications.
Figure 3B:
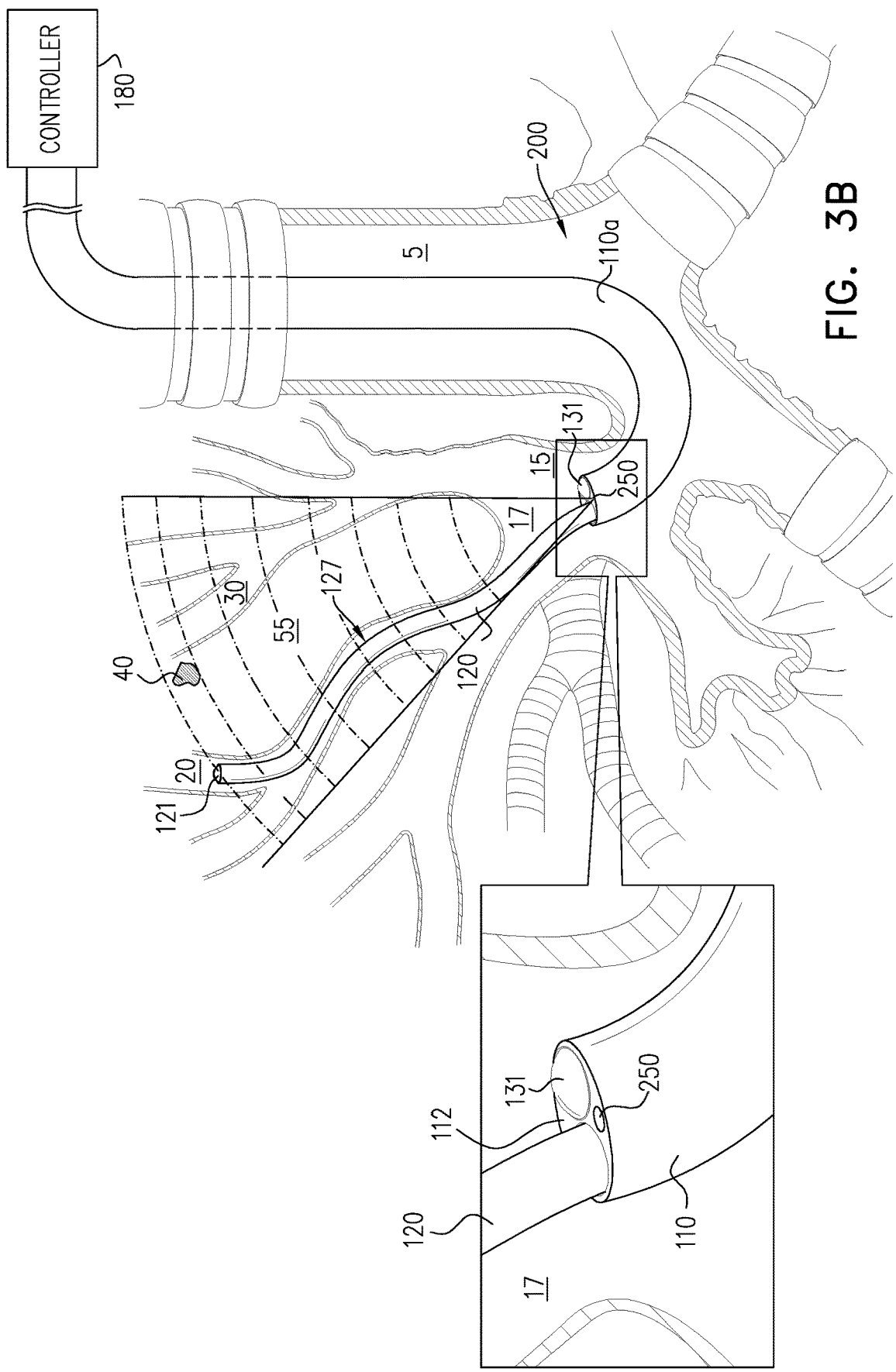

In order to obtain a view of tubes 120 and 130 advancing to their respective sites within lung 55, longer-range transceiver 250 may be disposed at the distal end of a sheath 110*a* (FIG. 3A). For example, longer-range transceiver 250 may be attached to the distal end of sheath 110*a*. Alternatively or additionally, longer-range transceiver 250 may be positioned at the end of a third tube (not shown) that is advanced through sheath 110*a*. In some such applications, sheath 110*a* may define an additional lumen for the third tube. Sheath 110*a* may be otherwise structurally and/or functionally identical to sheath 110. In some applications, longer-range transceiver 250 is not advanced through sheath 110*a*, but is advanced into lung 55 (or at least trachea 5) outside of the sheath.

Figure 3C:
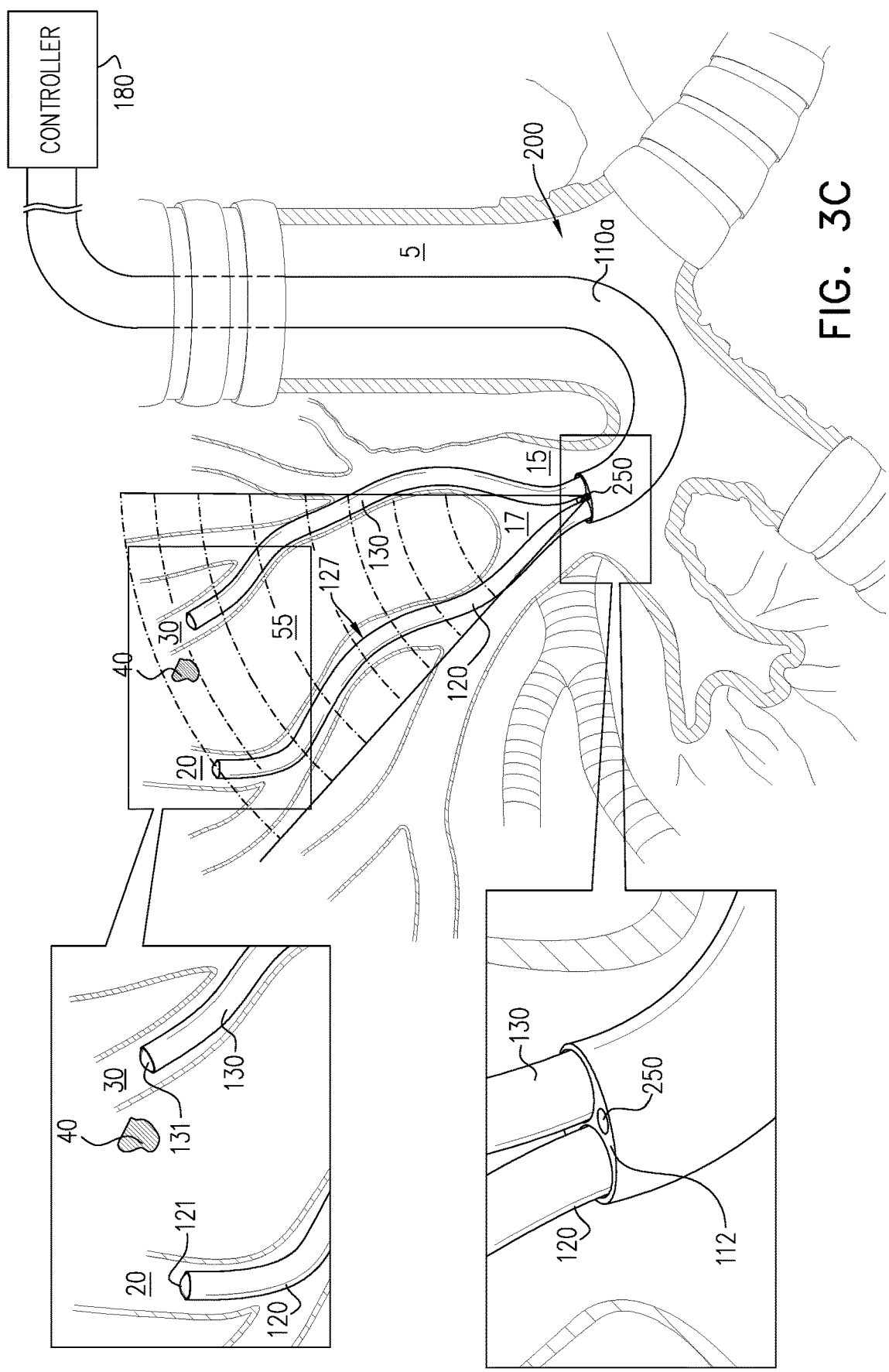

Ultrasound transceiver 250 is typically used to facilitate guidance of first tube 120 along first route 127 to imaging site 20 (FIG. 3B), and/or guidance of second tube 130 along second route 137 to tool site (FIG. 3C). Ultrasound transceiver 250 thereby serves as a "third-party" that is used to guide medical tool 138 into lung 55 such that it enters the effective imaging range of ultrasound transceiver 128 (or vice versa). Using ultrasound transceiver 250, once the operator is satisfied that first tube 120 is adequately positioned with respect to second tube 130 and target 40, ultrasound transceiver 128 can "take over" the imaging, providing the operator with a closer, more detailed view of the target and the medical tool.

It is hypothesized that utilizing a longer-range transceiver to oversee the delivery of tubes 120 and 130 to imaging and tool sites 20 and 30 may provide the operator with a larger field of view of the lung, and, in contrast, using a shorter-range transceiver to image the target may advantageously provide the operator with better imaging of the vasculature and other small structures of the lung during the procedure itself.

In some applications, transceivers 128 and 250 have similar imaging ranges, but the position of transceiver 250 nonetheless provides the operator with the additional advantageous view that the transceiver 128 alone cannot provide.

Reference is again made to FIGS. 1-7. It is hypothesized that the techniques disclosed herein advantageously allow ultrasound transceiver 128 to be positioned optimally for viewing the operation of the medical tool 138 at target 40—i.e. allowing both the ultrasound transceiver and the medical tool to obtain independent vantages of the target, facilitated by the ability to independently reposition the first tube and the second tube with respect to each other and with respect to the tissue. It is further hypothesized that these techniques advantageously allow for repositioning of ultrasound transceiver 128 (e.g. mid-procedure) without undesirably also repositioning tool 138. It is similarly hypothesized that these techniques advantageously allow for repositioning of tool 138 (e.g. mid-procedure) without undesirably also repositioning ultrasound transceiver 128.

Existing bronchoscopes that allow for simultaneous use of an ultrasound device and a tool typically have a diameter, along the entire length of the bronchoscope, that is wide enough to accommodate both the ultrasound device and the tool (e.g. side by side) along the entire length of the bronchoscope. This may restrict the depth to which the bronchoscope may be advanced into the lung, due to progressive narrowing of the airways at increased depth. It is hypothesized that the current invention facilitates deeper access into the lung due to the independence of tubes 120 and 130 from each other. For example, assigning ultrasound transceiver 128 its own, independently-steerable tube 120 allows second tube 130 to be narrower. This may allow (i) each of the tubes to be advanced deeper into the airways (e.g. into narrower bronchi) than would be possible for a bronchoscope that accommodates both an ultrasound device and a tool along its entire length, and (ii) the ultrasound device and the tool to be advanced and positioned independently of each other-thereby facilitating access to targets that are particularly deep within the lung.

Figure 13A:
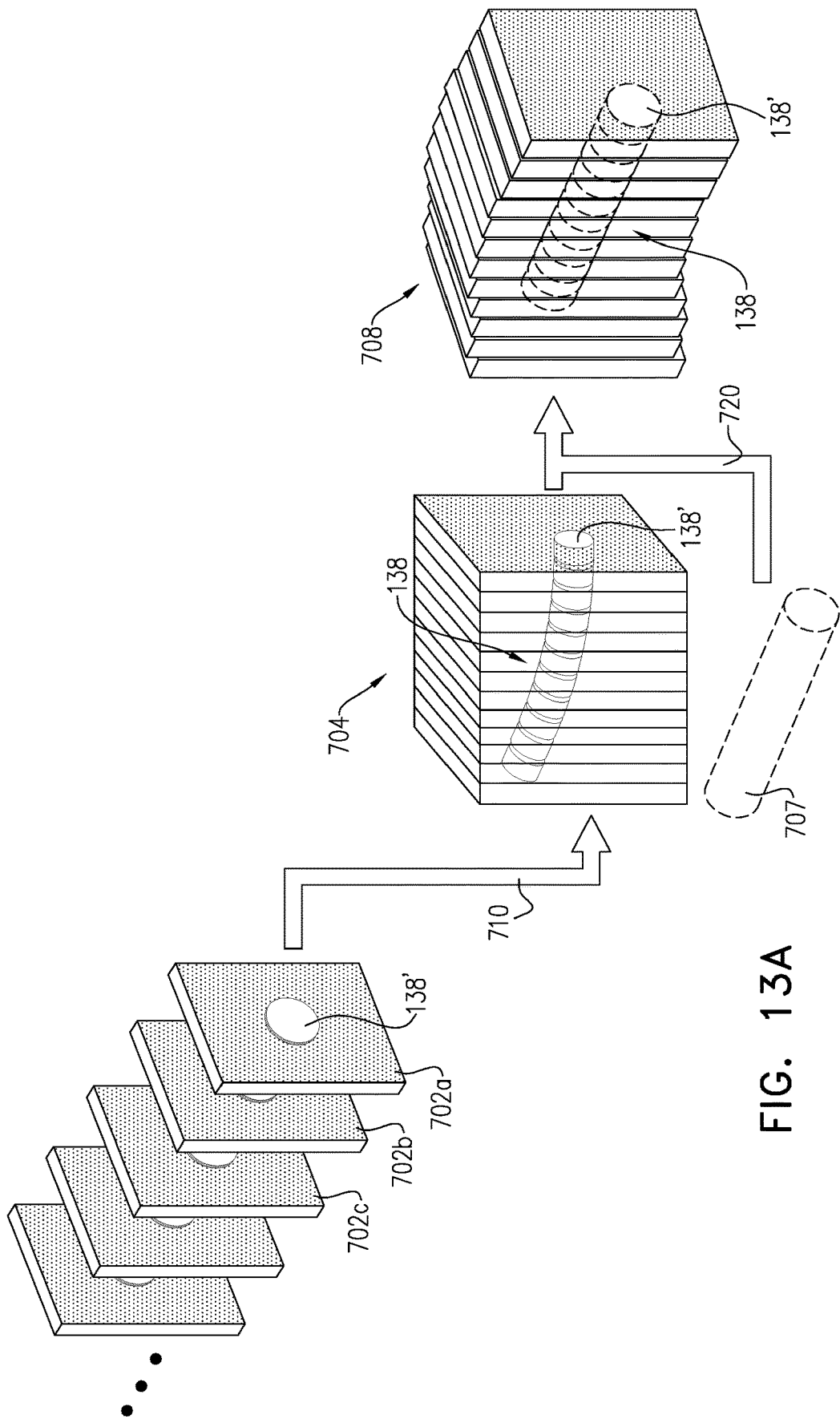
FIGS. 13A-B are schematic illustrations of techniques for use with a three-dimensional image in which a tool appears, in accordance with some applications.
Figure 13B:
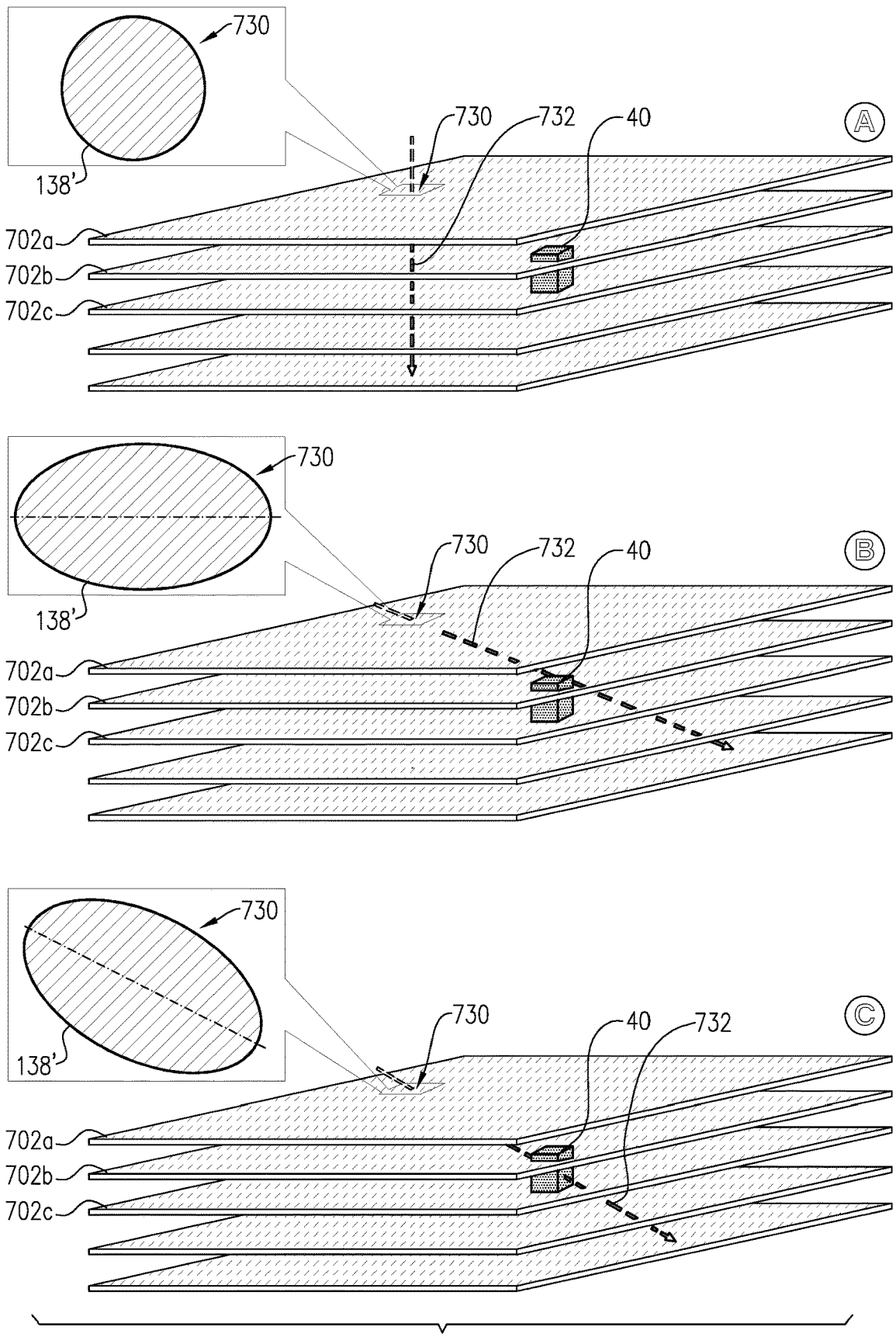

Reference is now made to FIGS. 13A-B, which are schematic illustrations of techniques for use with a 3D image in which a tool appears, in accordance with some applications.

FIG. 13A schematically illustrates techniques for adjusting alignment of a set of planar ultrasound images of, e.g., a target tissue, into a 3D image, in accordance with some applications. The alignment adjustment may serve to more accurately orient a tool, e.g., a biopsy needle, toward a target within the 3D composite image. As described hereinabove, ultrasound transceiver 128 may output a plurality of planar images that can be stacked (e.g. by controller 180) into a 3D image—i.e. a composite image. FIG. 13A shows an example in which such a plurality of planar images 702 (e.g., 702a, 702b, 702c) are received, and are then initially stacked into an ordered stack 704, which may be and/or represent a 3D ultrasound image—e.g. by which the operator is guided when performing procedure 440 (step 710). As described hereinabove, tool 138 is typically present within the 3D ultrasound image while procedure 440 is performed. For some applications, a step 720 may be performed in which the ultrasound image is refined (e.g. may be made more accurate and/or representative of the real world) by utilizing a known shape 707 (e.g. an outline) of medical tool 138, a slice 138' of which appears in each of planar images 702. In step 720, the alignment of planar images 702 with respect to each other is adjusted (e.g. in-plane) to produce an aligned ordered stack 708 in which slices 138' collectively assume (to at least a threshold degree) known shape 707 within the resulting 3D ultrasound image. By virtue of this alignment adjustment, the tissue that appears within the 3D ultrasound image may advantageously also be more accurately represented. The improved alignment may, for example, advantageously facilitate advancement of tool 138 to a small target within the tissue.

The adjustment of the alignment of planar images 702 is typically performed while maintaining the order of the planar images within the stack. The adjustment of the alignment may include in-plane translation (e.g. "sliding") of one image with respect to an adjacent image—e.g. as shown in FIG. 13A. For some applications, the adjustment of the alignment may include in-plane rotation of one image with respect to an adjacent image. For some applications, the adjustment of the alignment may be performed while maintaining the angular disposition between adjacent images (e.g. while maintaining the images parallel with each other). For some applications, the adjustment of the alignment may include adjusting the angular disposition between adjacent images (e.g. deflecting the plane of one image with respect to the plane of an adjacent image). For some applications, the adjustment of the alignment may be performed without adjusting spacing between adjacent images. For some applications, the adjustment of the alignment may include adjusting (e.g. increasing or decreasing) spacing between adjacent images.

There is therefore provided, in accordance with some applications of the present invention, a computer-implemented method for use with a tool (e.g. tool 138) at a target tissue. The method includes: (a) receiving shape data indicative of a shape (e.g. 3D shape) of the tool; (b) obtaining an ordered stack of ultrasound images, each of the ultrasound images of the stack including a respective slice of the tool and a respective slice of the target tissue; and (c) referencing the shape data, producing an aligned ordered stack of the ultrasound images by aligning the respective slices of the tool to match, to at least a threshold degree, the shape indicated by the shape data.

FIG. 13B schematically illustrates techniques for determining and/or adjusting a trajectory of a needle (e.g. tool 138) within a 3D composite image, such as that which may be generated by ultrasound transceiver 128, in accordance with some applications. FIG. 13B shows a stack of planar images 702 (e.g. images 702a, 702b, 702c, etc.)—i.e. a 3D composite image comprising planar images 702. As noted above, this may be the 3D ultrasound image, obtained by ultrasound transceiver 128, that is used to facilitate performance of the procedure on the target—e.g. by assisting the physician in guiding tool 138. Target 40 is schematically shown as appearing within the 3D image. At least part of the needle appears in the 3D image, such that at least one of 2D images 702 includes a cross-sectional slice 138' of the needle. In the particular example of FIG. 13B, it is 2D image 702a that includes slice 138'—e.g. at an entry point 730 at which the needle (i.e. a representation thereof) enters the 3D image.

The needle has a known cross-sectional shape. The described example relates to the cross-sectional shape being circular, and thereby slice 138' being elliptical. However, it is to be understood that, at least for some applications, the scope of the technique described is applicable, mutatis mutandis, to needles (or tools more generally) that have other cross-sectional shapes, and their correspondingly shaped slices within 2D images.

FIG. 13B shows three states (A, B, and C). In each state, slice 138' appears in image 702a, and is elliptical. However, the eccentricity and orientation of the elliptical slice is dependent on the angle and orientation of the needle with respect to image 702*a*, and thereby with respect to the 3D image. (It is to be noted that this, in turn, may be dependent on the orientation, within the lung, of ultrasound transceiver 128 with respect to tool 138.) In state A, elliptical slice 138' is circular, in state B it has a greater eccentricity than in state A (e.g. is a non-circular ellipse), and in state C it has a similar (e.g. identical) eccentricity as, but a different orientation than, state B. It is to be understood that these three states have been chosen purely for illustrative purposes.

A data-processing system (which may be a component of system 100, such as a component or module of controller 180) is configured to determine (e.g. calculate) the eccentricity of slice 138' and its orientation within its 2D image, and to responsively determine (e.g. calculate) a vector 732 of the needle (i.e. its representation) within the 3D image, and thereby with respect to the target tissue that appears in the 3D image. For example, in state A, responsively to determining the circularity (i.e. eccentricity=0) of slice 138', the data-processing system would determine that vector 732 of the needle is transverse with respect to image 702*a*. Similarly, in state B, responsively to determining the eccentricity (i.e. greater eccentricity) of slice 138', the data-processing system would determine that vector 732 is at a particular shallower angle with respect to image 702*a*. In state C, responsively to determining that slice 138' has the same eccentricity as state B, but a different orientation with respect to image 702*a* (i.e. a different rotational orientation within the plane of image 702*a*), the data-processing system would determine that vector 732 is at the same angle, but different orientation, with respect to image 702*a*, as in state B.

Vector 732 may be considered to be a trajectory of needle 138—e.g. through the 3D image and/or through the tissue. For some applications, this trajectory may be a predicted trajectory. For example, should the needle appear only in a subset of images 702 (e.g. in only image 702*a*), vector 732 may represent the predicted trajectory of the needle through the 3D image (and thereby through the tissue)—e.g. should the needle be advanced axially in its current position and orientation. The data-processing system (e.g. controller 180) may superimpose the predicted trajectory onto the ultrasound image so as to aid the physician to advance the needle in the desired manner—e.g. to target 40. For some such applications, FIG. 13B may therefore be considered to represent such superimpositions—e.g. augmented ultrasound images—for states A, B, and C. Furthermore, for such applications, states A, B, and C may illustrate progressive reorientation of the needle in order to orient the needle appropriately to reach target 40. State A may represent an initial state, state B may represent reorientation of the needle to a (shallower) angle that is appropriate for an eventual trajectory to target 40, and state C may represent subsequent reorientation of the needle in a sweeping manner that finally orients the trajectory such to pass through target 40. It is to be understood that even when states A, B, and C are considered to illustrate such reorientation, they are intended to illustrate how such reorientation is possible, rather than to represent discrete and/or necessary steps in such reorientation. The data-processing system (e.g. controller 180) may alternatively or additionally provide a discrete (e.g. quantitative) indication of reorientation required in order to achieve the desired trajectory.

For some applications, the eccentricity and/or orientation of slice 138' (as well as optionally its planar position within its 2D image) may be utilized by the data-processing system (e.g. controller 180) in order to refine the 3D ultrasound image. For example, these characteristics may be determined (e.g. calculated) for multiple slices 138' (in respective 2D images), and may be compared in order to determine whether the 2D images in the stack are correctly aligned. For example, from the vector determined from the characteristics of a first slice 138', the characteristics of a second slice (e.g. that of the next image in the stack) may be predicted—e.g. for a straight needle, the eccentricity and orientation of the second slice may be predicted to be identical to those of the first slice, while the planar position of the second slice may be predicted to be offset from that of the first slice according to the vector determined from the first slice. Should the characteristics of the second slice not match the predicted characteristics, the data-processing system may adjust the alignment between the first and second slices in order to cause the characteristics to match the prediction, and thereby to refine the 3D image. For some applications, this may therefore be considered to be a variant of the technique described with reference to FIG. 13A.

In some applications, the systems and techniques described with reference to FIGS. 13A-B may be performed by system 100, e.g., controller 180 thereof, or a separate data-processing system.

Reference is now made to FIGS. 14A-E and 15, which are schematic illustrations and a flowchart showing at least some steps of a technique by which an electromagnetic signal is used to facilitate positioning of tool 138 within a field of view of ultrasound transceiver 128, in accordance with some applications.

Tool 138 may comprise an electrically-conductive material such as, but not limited to, a metal. Nonlimiting examples of such materials include stainless steel, carbon steel, titanium, tantalum, tungsten, platinum, and palladium. For such applications, an electromagnetic signal 800 may be driven through the tool—e.g. by connecting a signal generator to a proximal end of tool 138. This connection may be achieved using a general-purpose electrical clip (e.g. a crocodile clip), and/or tool 138 may be provided with a dedicated electrical terminal (e.g. at a proximal end of the tool) via which the signal generator may be mechanically and electrically connected.

It has been determined by the inventors that such an electromagnetic signal, appropriately configured, is detectable by ultrasound transceiver 128. For example, the electromagnetic signal may cause electrical interference in ultrasound imaging. In some situations such interference may be undesirable—e.g. due to it resulting in "noise" (e.g. "snow") in the image output by the ultrasound transceiver, thereby degrading the image and reducing its utility. In contrast, the present disclosure includes a technique in which such electromagnetic interference can be advantageously utilized for guidance of the tool and/or the ultrasound transceiver—e.g. by providing information on the proximity of the tool to the ultrasound transducer.

The detection of electromagnetic signal 800 by ultrasound transceiver 128 may occur via interaction with electronic components of the ultrasound transceiver and/or the ultrasound tool of which the ultrasound transceiver is a component (e.g. its wiring). For example, the ultrasound tool (e.g. wires that extend proximally from the transceiver component—e.g. the piezoelectric crystal) may electrically conduct the electromagnetic signal from the imaging site to an extracorporeal unit (e.g. an ultrasound processor unit) of the ultrasound tool that is configured to receive and/or display the ultrasound signal). This extracorporeal unit may be controller 180, may be a component of controller 180, may be connectable to controller 180, or may be independent of controller 180. Irrespectively, this extracorporeal unit may be a component of system 100.

In the example shown in FIGS. 14A-E, this electromagnetically-facilitated guidance is performed once ultrasound transceiver 128 and tool 138 have arrived at sites 20 and 30*a*, respectively (e.g. as described with reference to FIG. 2E, mutatis mutandis). However, it is to be noted that this guidance may be used at other points in the procedure, and for other procedures, with or without tubes 120 and 130. In some applications, the position refinement may be achieved by moving tube 120 in addition to or alternatively to advancing ultrasound transceiver 128 out of tube 120.

Figure 14A:
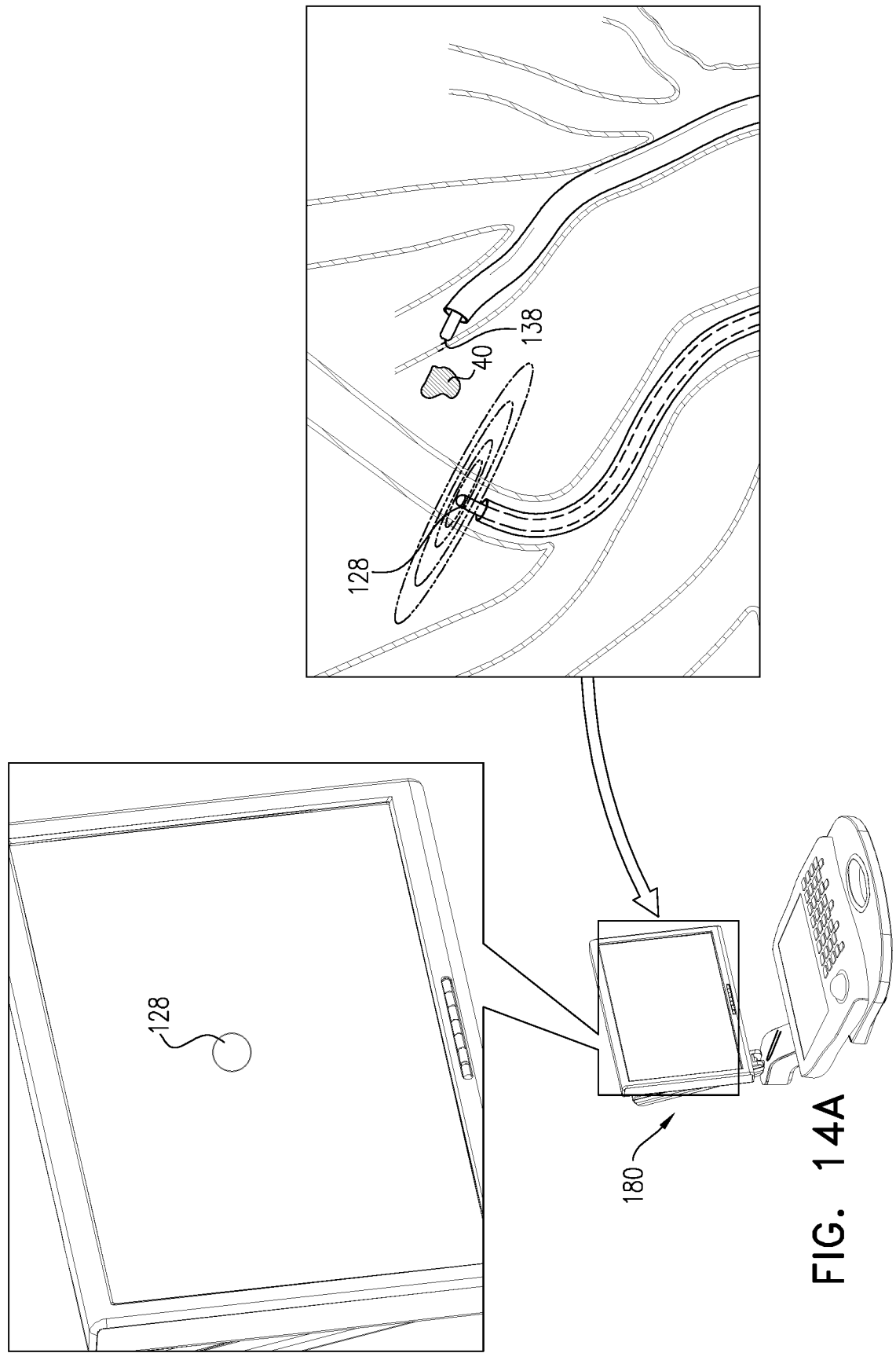
FIGS. 14A-14E and 15 are schematic illustrations of systems and methods for use with an ultrasound transceiver and a tool, in accordance with some applications.
Figure 14B:
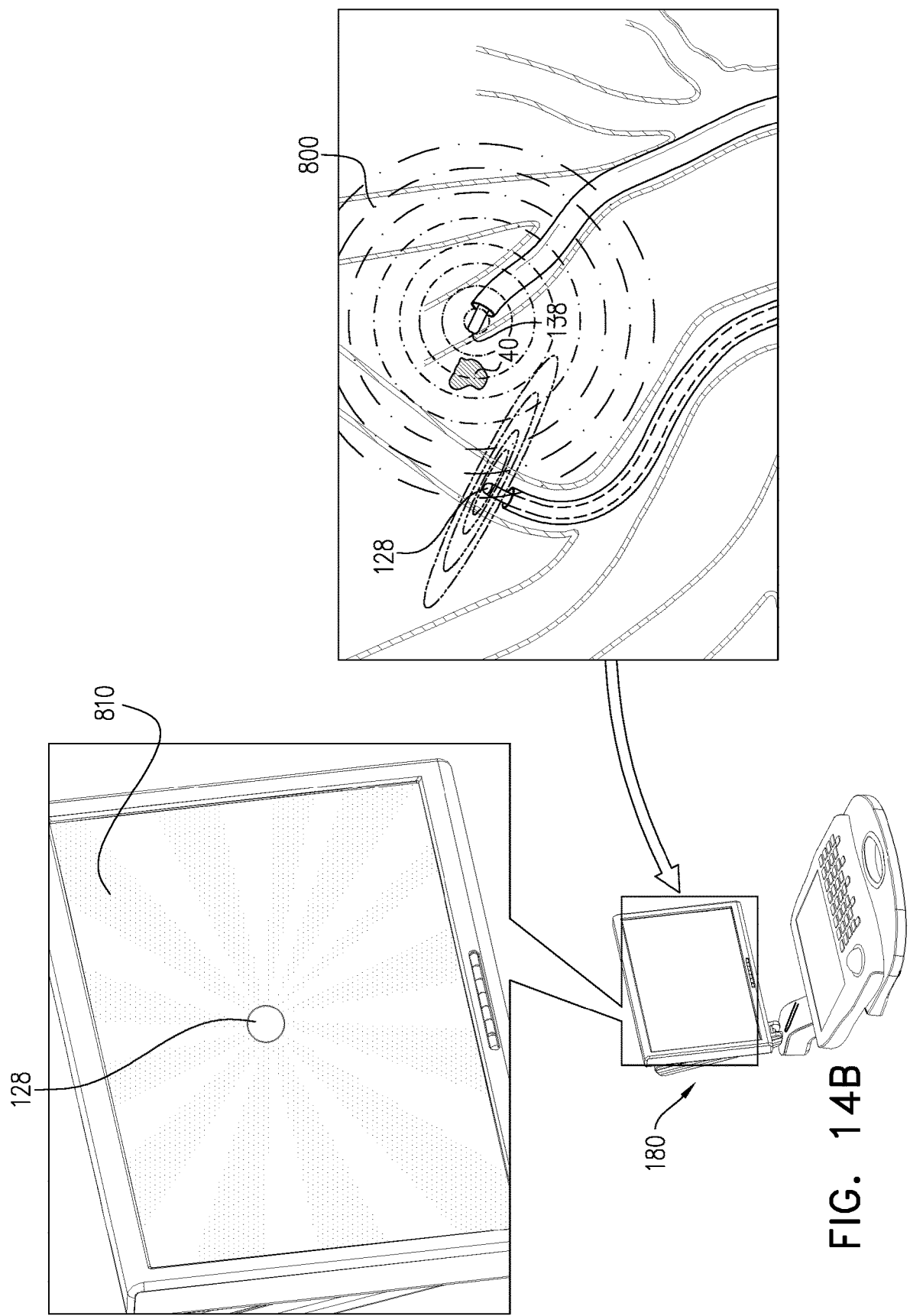
Figure 14C:
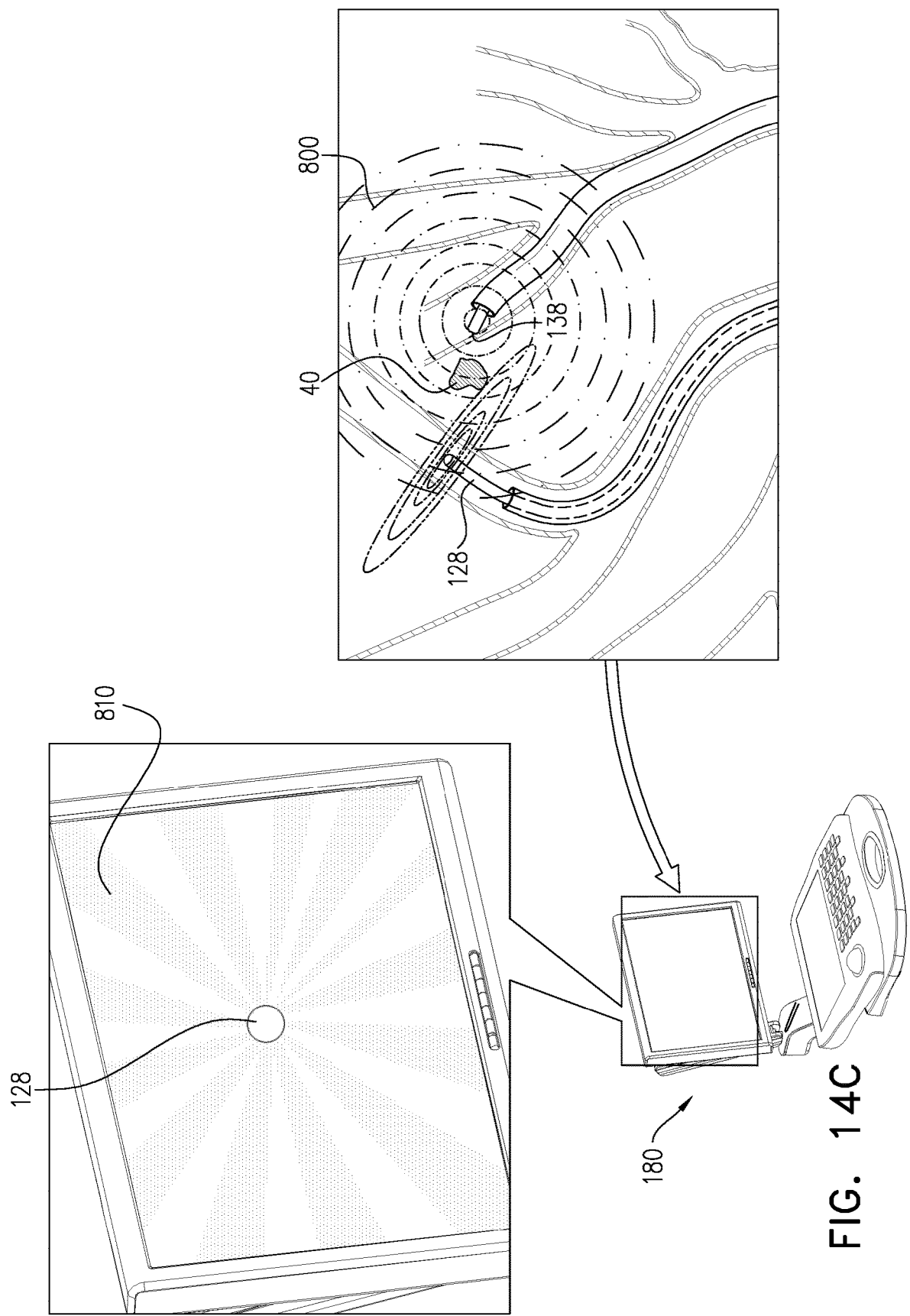
Figure 14D:
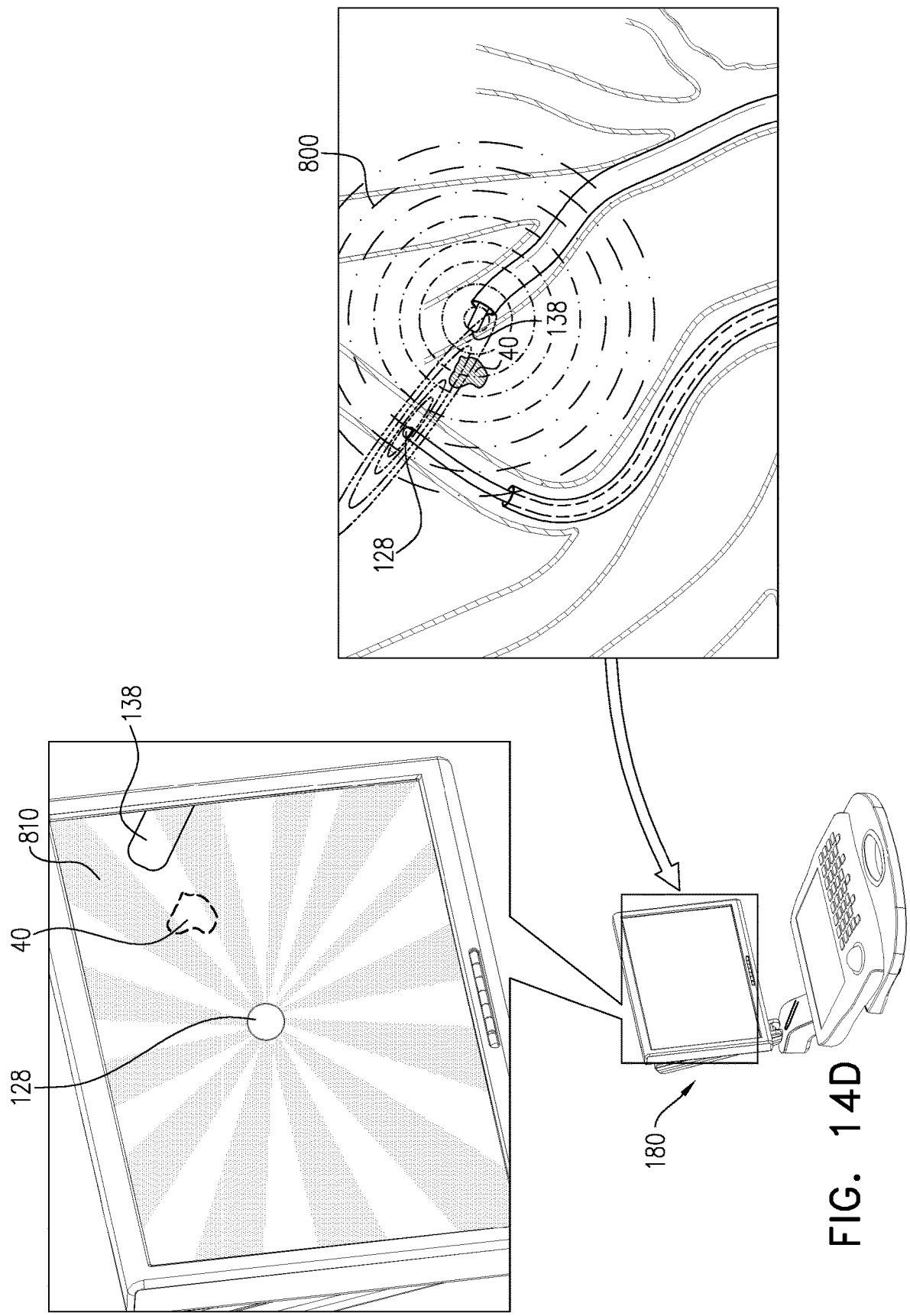
Figure 14E:
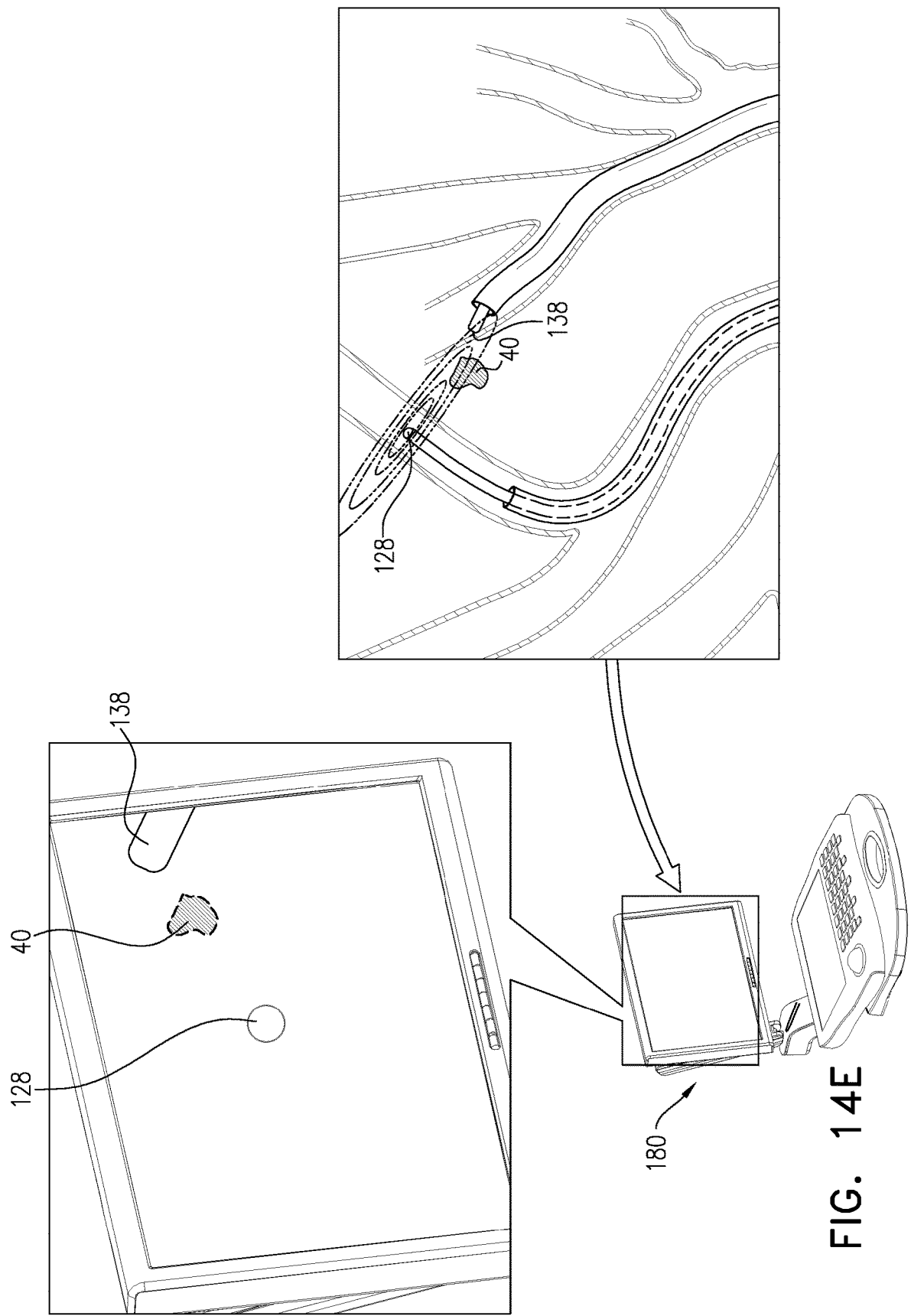
Figure 15:
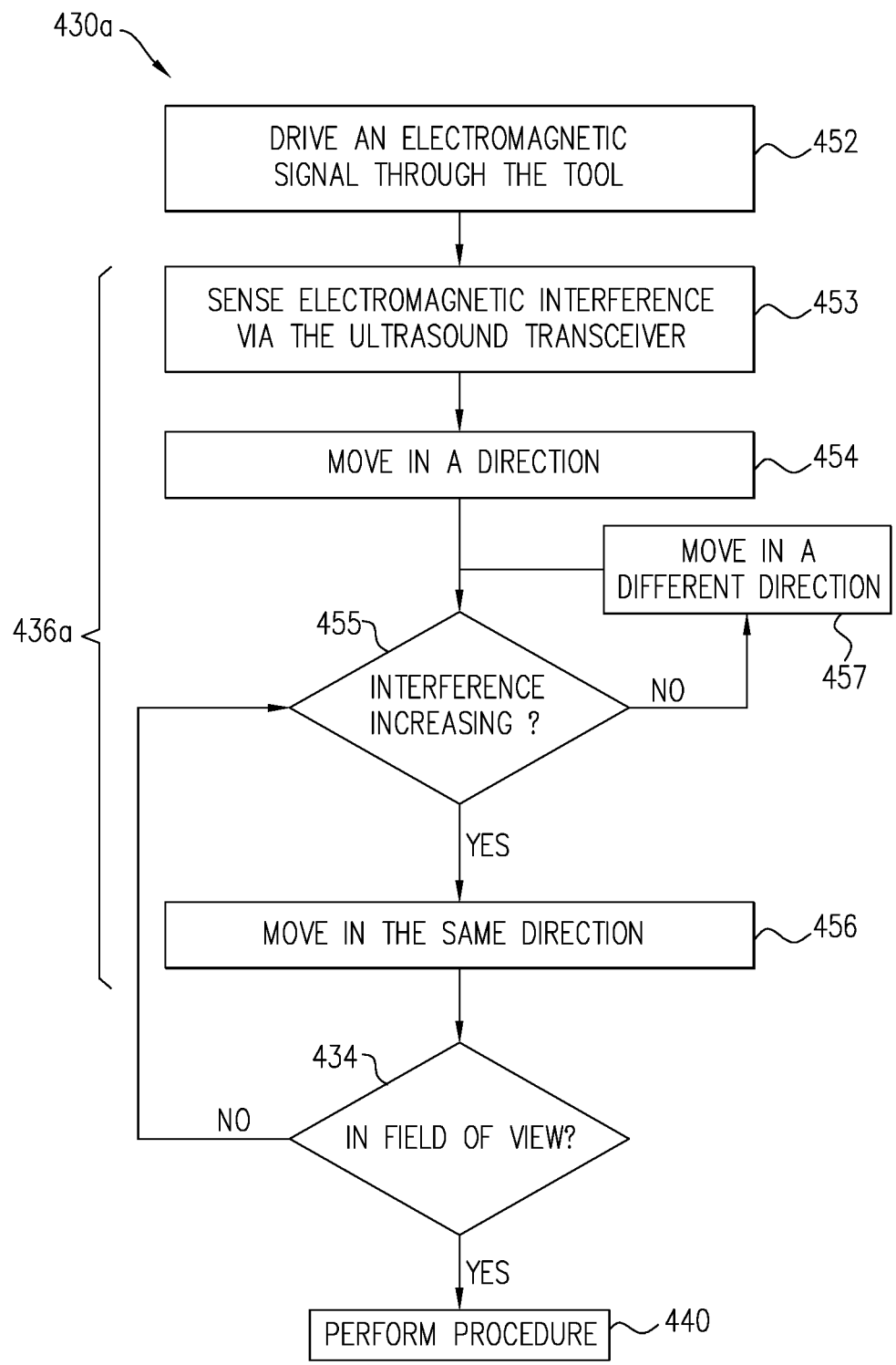

FIG. 15 is a flowchart of at least some steps in a technique 430*a* for refinement of the position of ultrasound transceiver 128 and/or tool 138. Technique 430*a* may generally correspond to the technique described with reference to FIGS. 14A-E, and moreover may be considered to be a variant of step 430 (FIGS. 5-7). Similarly, a subsection 436*a* of technique 430*a* may be considered to be a variant of repositioning step 436 described with reference to FIG. 7.

FIG. 14A shows a state similar to that shown in FIG. 2E except that the position of ultrasound transceiver 128 at tool site 20 and/or of tool 138 at tool site 30 require refinement in order to acquire visualization of the tool within the field of view of the ultrasound transceiver, represented by the concentric circles surrounding ultrasound transceiver 128. An electromagnetic signal 800 is driven through tool 138 (FIG. 14B; FIG. 15 step 452). The signal causes interference 810 in the output of ultrasound transceiver 128 (e.g. is sensed by the ultrasound transceiver as interference; FIG. 15 step 453).

It has been determined by the inventors that the magnitude of interference 810 diminishes with increased distance from ultrasound transceiver 128, and that it is therefore possible to identify that the distance between the ultrasound transceiver and the tool (i.e. the "transceiver-to-tool distance") is decreasing by identifying that the magnitude of the signal is increasing.

Thus, positioning of the tool can be facilitated and/or guided by monitoring the magnitude of the interference. For example, if the magnitude of the interference increases as tool 138 is moved, it may be determined that the direction of movement is toward the ultrasound transceiver. Similarly, if the magnitude of the interference increases as ultrasound transceiver is moved, it may be determined that the direction of movement is toward the tool. This technique may therefore be used to bring tool 138 into the field of view of ultrasound transceiver 128.

FIG. 14C shows ultrasound transceiver 128 having been moved in a direction (FIG. 15 step 454). As shown in FIG. 14C, as a result of this movement, the detected interference 810 has increased. As described hereinabove, this may be indicative of a reduction in the transceiver-to-tool distance—e.g. that the direction of movement was appropriate for reducing the transceiver-to-tool distance. Therefore, responsively to identifying that the interference increased (FIG. 15 decision 455), transceiver 128 is moved further in the same direction (FIG. 14D; FIG. 15 step 456). (Should the interference not have increased, the ultrasound transceiver may be moved in a different direction; FIG. 15 step 457). This process may be repeated iteratively until tool 138 appears in the field of view of the ultrasound transceiver (decision 434), at which point the procedure may be performed (e.g. step 440 of FIGS. 5-7, and 15). Electromagnetic signal 800 may be turned off prior to performing the procedure (FIG. 14E)—e.g. in order to eliminate the interference during performance of the procedure.

Although FIGS. 14A-E show movement of ultrasound transceiver 128 toward tool 138, as indicated in FIG. 15, the tool could alternatively or additionally be moved toward the ultrasound transceiver.

There is therefore provided, in accordance with an application of the present invention, a method comprising advancing a tool into a subject, toward a tissue of the subject; driving an electromagnetic signal through the tool; advancing an ultrasound transceiver into the subject; and sensing the electromagnetic signal via the ultrasound transceiver. The method may further comprise subsequently reducing the transceiver-to-tool distance, guided by a strength of the signal increasing with reduction of the transceiver-to-tool distance. Reducing the transceiver-to-tool distance may comprise moving the ultrasound transceiver toward the tool, and/or moving the tool toward the ultrasound transceiver. The reduction of the transceiver-to-tool distance may be performed by observing a computer-generated estimate of the transceiver-to-tool distance, the computer-generated estimate being generated responsively to the intensity of the signal.

In some applications, some steps of FIGS. 14A-E and 15 may be fully or partially automated, e.g., performed by robotic-control module 186, and/or implemented with assistance of a data-processing system. In some applications, advancement/retraction of either the ultrasound transceiver and/or the tool may be guided by the robotic-control module in response to input from the electromagnetic interference. In some applications, the strength of interference 810 may be detected and converted to a numerical value, e.g., transceiver-to-tool distance, by a program run by a data-processing system. The computer program may be used to identify an increase or decrease in the transceiver-to-tool distance by identifying that the magnitude of the signal is increasing. Thus, positioning of the tool can be facilitated and/or guided by a control system monitoring the magnitude of the interference.

The frequency of electromagnetic signal 800 is typically within the range of radio waves, and may be set to optimize its detection (as interference) by ultrasound transceiver 128. For example, the frequency of electromagnetic signal 800 may be approximately the same as the frequency of the ultrasound waves that ultrasound transceiver is configured to detect (and typically also at which the ultrasound transceiver is configured to emit). For example, the frequency of electromagnetic signal 800 may be at least 1 MHZ (e.g. at least 5 MHZ, e.g. at least 10 MHZ, such as at least 15 MHZ) and/or no more than 50 MHZ (e.g. no more than 30 MHZ, e.g. no more than 25 MHz, such as no more than 22 MHZ). For some applications the frequency of electromagnetic signal 800 may be between 18 and 22 MHz, such as approximately 20 MHZ.

In the example shown, interference 810 appears (e.g. is outputted) as visual interference in the image derived from the ultrasound transceiver. However, the scope of the disclosure includes interference of other kinds, such as auditory interference (e.g. an audible output).

For some applications, controller 180 may be configured to expressly recognize detection of signal 800 (e.g. detection of interference 810')—e.g. as distinct from the "true" ultrasound signal. For example, the electromagnetic signal may be configured (e.g. modulated) in a manner that is recognizable by controller 180.

Electromagnetic signal 800 may be applied and/or detected intermittently. For example, the electromagnetic signal may be turned on or off by the operator as needed, e.g. to permit viewing the ultrasound image without interference

810. However, the operator may choose to use the electromagnetic signal while imaging the tissue and/or performing the procedure.

Intermittent application and/or detection of signal 800 may also be used to determine the component of the ultrasound output (e.g. the magnitude of that component) that is attributable specifically to interference 810—e.g. as opposed to the component of the ultrasound output that is attributable to true detection of ultrasound. For example, for applications in which the ultrasound output is displayed as an image, a brightness of the image (e.g. the average pixel brightness, or the total image brightness) obtained while electromagnetic signal 800 is off is subtracted from the brightness of the image obtained while the electromagnetic signal is on. Thus, interference 810 may be quantified by making reference to a comparable ultrasound image in which interference 810 is known to be absent.

In some applications, more than merely identifying that the transceiver-to-tool distance is decreasing, controller 180 may be configured to calculate the actual transceiver-to-tool distance. For example, the transceiver-to-tool distance may be calculated based on quantification of interference 810. Alternatively or additionally, the transceiver-to-tool distance may be calculated responsively to the changes in the magnitude of the interference as the tool and/or the ultrasound transceiver is moved by a known distance. For example, the transceiver-to-tool distance may be calculated at least in part by utilizing the inverse square law. Thus, the magnitude of signal 800 and/or interference 810 detected may be outputted as a computer-generated estimate of the transceiver-to-tool distance. Such ability to calculate the transceiver-to-tool distance may advantageously facilitate refinement of the position of the tool with respect to the ultrasound transceiver. It is noted that a variety of transceivers and tools may provide the required electromagnetic properties; thus, the signal detection is possible without a discrete or dedicated electromagnetic transmitter or a discrete or dedicated electromagnetic receiver.

For some applications in which the actual transceiver-to-tool distance is calculated (e.g. based on quantification of interference 810), the vector along which ultrasound transceiver 128 is being moved may be determined—e.g. by calculating and comparing the transceiver-to-tool distance at several points along the vector.

The apparatuses and methods described in this disclosure (e.g., generation of the computer model, image processing, generation of the map and/or the airway representations therein, designation of the sites and/or routes, and/or other processing) may be partially or fully implemented by one or more computer programs executed by one or more processors. The computer programs include processor-executable instructions that are stored on at least one non-transitory tangible computer readable medium. The computer programs may also include and/or rely on stored data.

Each of the various systems, devices, apparatuses, etc. in this disclosure can be sterilized (e.g., with heat, radiation, ethylene oxide, hydrogen peroxide, etc.) to ensure they are safe for use with patients, and the methods herein can comprise sterilization of the associated system, device, apparatus, etc. (e.g., with heat, radiation, ethylene oxide, hydrogen peroxide, etc.). Furthermore, the scope of the present disclosure includes, for some applications, sterilizing any of the various systems, devices, apparatuses, etc. in this disclosure.

The present invention is not limited to the examples that have been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Further, the treatment techniques, methods, steps, etc. described or suggested herein or references incorporated herein can be performed on a living animal or on a non-living simulation, such as on a cadaver, cadaver heart, anthropomorphic ghost, simulator (e.g., with the body parts, tissue, etc. being simulated), etc.

The invention claimed is:

1. A method for use with a lung of a subject, the method comprising:
   advancing a first tube through a trachea of the subject;
   guided by a first camera disposed at an end of the first tube, advancing the end of the first tube along a first airway route to an imaging site within the lung;
   advancing a second tube through the trachea independently of advancing the first tube through the trachea;
   guided by a second camera disposed at an end of the second tube, and while the end of the first tube remains at the imaging site, advancing the end of the second tube along a second airway route to a tool site within the lung;
   subsequently, withdrawing the first camera from the first tube and the second camera from the second tube;
   subsequently, advancing:
      an imaging device through the first tube to the end of the first tube, and
      a tool through the second tube to the end of the second tube; and
   subsequently, performing a procedure on a target within the lung using the tool while guiding the procedure by using the imaging device to observe positioning of the tool with respect to the target.

2. The method according to claim 1, wherein performing the procedure on the target comprises performing the procedure while the target is disposed between the imaging device and the tool.

3. The method according to claim 1, wherein advancing the end of the first tube comprises actively steering the first tube using an extracorporeal first-tube controller.

4. The method according to claim 1, wherein the imaging device comprises an ultrasound transceiver, and wherein using the imaging device to observe the positioning of the tool with respect to the target comprises imaging the tool and the target using the ultrasound transceiver.

5. The method according to claim 1, wherein the imaging device is a LIDAR device, and wherein using the imaging device to observe the positioning of the tool with respect to the target comprises imaging the tool and the target using the LIDAR device.

6. The method according to claim 1, wherein the target is located within a target bronchus of the lung, and wherein advancing the end of the second tube along the second airway route to the tool site comprises advancing the end of the second tube intrabronchially along the second airway route to the target bronchus.

7. The method according to claim 1, wherein:
   the tool includes a tool element selected from the group consisting of: a needle, a blade, scissors, a suction device, jaws, a grasper, an ablation device, and an energy applicator; and
   performing the procedure on the target using the tool comprises performing the procedure on the target using the tool that includes the selected tool element.

8. The method according to claim 1, wherein performing the procedure comprises ablating the target.

9. The method according to claim 1, wherein performing the procedure comprises excising a foreign body from the lung.

10. The method according to claim 1, wherein:
the target is situated outside of an airway of the lung,
the tool site is within the airway,
advancing the end of the second tube along the second airway route to the tool site comprises advancing the end of the second tube along the second airway route to the tool site that is within the airway, and
performing the procedure on the target using the tool extended from the end of the second tube comprises extending the tool through a wall of the airway and into the target.

11. The method according to claim 1, wherein:
the method further comprises advancing a sheath via the trachea toward the lung;
advancing the end of the first tube comprises extending the first tube out of the sheath; and
advancing the end of the second tube comprises extending the second tube out of the sheath independently of extending the first tube out of the sheath.

12. The method according to claim 11, wherein:
the lung defines a fork, the at which a bronchus of the lung forks distally into a first branch and a second branch,
advancing the sheath comprises advancing a distal part of the sheath via the trachea into the bronchus, not beyond the fork, and
advancing the end of the first tube along the first airway route to the imaging site comprises advancing the end of the first tube beyond the fork, and via the first branch to the imaging site.

13. The method according to claim 12, wherein advancing the end of the second tube along the second airway route to the tool site comprises advancing the end of the second tube beyond the fork, and via the second branch to the tool site.

14. The method according to claim 13, wherein the imaging site is situated, along the first airway route, at a different bronchus-generational depth than is the tool site, along the second airway route.

15. The method according to claim 11, wherein advancing comprises advancing a distal part of the sheath into a bronchus of the lung guided by binocular vision provided by the first camera and the second camera.

16. The method according to claim 1, wherein:
performing the procedure on the target using the tool extended from the end of the second tube comprises performing a first part of the procedure on the target using the tool extended from the end of the second tube, and
the method further comprises, subsequently to performing the first part of the procedure, and while the end of the first tube remains at the imaging site:
withdrawing the imaging device from the first tube;
withdrawing the tool from the second tube;
subsequently, advancing the tool through the first tube; and
subsequently, performing a second part of the procedure on the target using the tool extended from the end of the first tube.

17. The method according to claim 16, wherein:
the method further comprises, subsequently to withdrawing the imaging device from the first tube and the tool from the second tube, and while the end of the second tube remains at the tool site, advancing the imaging device through the second tube, and
performing the second part of the procedure comprises performing the second part of the procedure, guided by imaging of the target by the imaging device at the end of the second tube.

18. The method according to claim 1, wherein, for each of the first camera and the second camera, the respective camera includes a light source, and advancing the end of the respective tube guided by the camera comprises advancing the end of the respective tube while the respective airway route is illuminated by the light source.

19. The method according to claim 1, wherein using the imaging device to observe the positioning of the tool with respect to the target comprises determining a presence of the target and the tool in a field of view of the imaging device.

20. The method according to claim 19, wherein the method further comprises, subsequently to determining the presence of the target and the tool in the field of view, repositioning the tool with respect to the imaging device and the target while retaining the tool in the field of view.

21. The method according to claim 19, wherein the method further comprises, subsequently to determining the presence of the target and the tool in the field of view, repositioning the imaging device with respect to the tool and the target while retaining the tool in the field of view.

\* \* \* \* \*